US009187761B2

(12) United States Patent
Schmülling et al.

(10) Patent No.: US 9,187,761 B2
(45) Date of Patent: Nov. 17, 2015

(54) TRANSCRIPTIONAL REPRESSORS OF CYTOKININ SIGNALING AND THEIR USE

(75) Inventors: Thomas Schmülling, Berling (DE); Alexander Heyl, Berlin (DE); Eswar Ramireddy, Berlin (DE)

(73) Assignees: Thomas Schmulling, Berlin (DE); Alexander Heyl, Berlin (DE); Eswar Ramireddy, Berlin (DE)

( * ) Notice: Subject to any disclaimer, the term of this patent is extended or adjusted under 35 U.S.C. 154(b) by 1247 days.

(21) Appl. No.: 12/442,662

(22) PCT Filed: Sep. 25, 2007

(86) PCT No.: PCT/EP2007/008331
§ 371 (c)(1),
(2), (4) Date: Nov. 20, 2009

(87) PCT Pub. No.: WO2008/037431
PCT Pub. Date: Apr. 3, 2008

(65) Prior Publication Data
US 2010/0115666 A1 May 6, 2010

Related U.S. Application Data

(60) Provisional application No. 60/846,967, filed on Sep. 25, 2006.

(51) Int. Cl.
| C12N 15/79 | (2006.01) |
| C12N 15/82 | (2006.01) |
| C12N 15/62 | (2006.01) |
| C07K 14/415 | (2006.01) |

(52) U.S. Cl.
CPC .......... *C12N 15/8261* (2013.01); *C07K 14/415* (2013.01); *C12N 15/62* (2013.01); *C12N 15/79* (2013.01); *C12N 15/8201* (2013.01); *C12N 15/8241* (2013.01); *C12N 15/8295* (2013.01); *C07K 2319/80* (2013.01)

(58) Field of Classification Search
None
See application file for complete search history.

(56) References Cited

U.S. PATENT DOCUMENTS

| 4,945,050 A | 7/1990 | Sanford et al. |
| 5,122,466 A | 6/1992 | Stomp et al. |
| 5,405,765 A | 4/1995 | Vasil et al. |
| 5,693,512 A | 12/1997 | Finer et al. |
| 5,736,369 A | 4/1998 | Bowen et al. |
| 5,874,265 A | 2/1999 | Adams et al. |
| 5,955,362 A | 9/1999 | Chang et al. |
| 5,969,213 A | 10/1999 | Adams et al. |
| 5,990,390 A | 11/1999 | Lundquist et al. |
| 2006/0185030 A1* | 8/2006 | Sheen et al. ........ 800/278 |

FOREIGN PATENT DOCUMENTS

| DE | 4309203 | 4/1994 |
| EP | 0604662 | 7/1994 |
| EP | 0687730 | 12/1995 |
| WO | 9318168 | 9/1993 |
| WO | 9400977 | 1/1994 |
| WO | 9413822 | 6/1994 |
| WO | 9506722 | 3/1995 |
| WO | 9712046 | 4/1997 |
| WO | 9748814 | 12/1997 |
| WO | 9817813 | 4/1998 |
| WO | 9854961 | 12/1998 |
| WO | 9901563 | 1/1999 |
| WO | 9904618 | 2/1999 |
| WO | 9922003 | 5/1999 |
| WO | 0015662 | 3/2000 |
| WO | 0017365 | 3/2000 |
| WO | 02099079 | 12/2002 |

OTHER PUBLICATIONS

Hiratsu et al (2003, The Plant Journal 34:733-739).*
Mason et al(2005 The Plant Cell 17:3007-3018).*
Sakai et al (the Plant Journal 24(6):703-711).*
Campbell and Reece (2002, Biology, 6th edition, Benjamin Cummings, San Francisco, p. 793).*
Matsui, K., et al., (2005), Plant Cell Physiol., vol. 46 (1), pp. 147-155.
Heyl, A., et al., (2003), Current Opinion in Plant Biology, vol. 6, pp. 480-488.
Kazan, K., (2006), Trends in Plant Science, vol. 11 (3), pp. 109-112.
Aida, M., et al. (1997) Plant Cell, 9: 841-857.
Brenner, W.G., et al. (2005) Plant J, 44: 314-333.
Chandler, J.W. and Werr, W. (2003) Trends Plant Sci, 8: 279-285.
Clough, S.J. and Bent, A.F. (1998) Plant J., 16: 735-743.
D'Agostino, I.B., et al. (2000) Plant Physiol., 124: 1706-1717.
Dortay, H., et al. (2006). FEBS Journal 273: 4631-4644.
Ehlert, A., et al. (2006). Plant J. 46: 890-900.
Ferreira, F.J. and Kieber, J.J. (2005) Curr. Opin. Plant Biol., 8: 518-525.
Finn, R.D., et al. (2006) Nucleic Acids Res, 34: D247-251.
Grefen, C. and Harter, K. (2004) Planta, 219: 733-742.

(Continued)

*Primary Examiner* — Stuart F Baum
(74) *Attorney, Agent, or Firm* — McDonnell Boehnen Hulbert & Berghoff LLP

(57) ABSTRACT

The invention relates to fusion proteins capable of acting as transcriptional repressors of cytokinin signaling, to polynucleotides encoding these fusion proteins, to vectors and cells comprising these polynucleotides, and to transgenic plants and parts thereof comprising these polynucleotides, vectors, and cells.
The invention further relates to a process for making these transgenic plants and to the use of these transgenic plants for producing seeds of enhanced size, with enhanced seed filling, with reduced seed loss and/or with more rapid germination, and/or for producing a live root system with increased root mass, root length and/or root branching. The invention also relates to a method for enhancing the seed size, for enhancing seed filling, for reducing seed loss, and/or for reducing germination time and/or reproduction time, and/or for enhancing the root mass, root length and/or root branching of a plant and to seeds obtainable by the methods of the present invention.

28 Claims, 11 Drawing Sheets

(56) References Cited

OTHER PUBLICATIONS

Hass, C., et al. (2004) EMBO J., 23: 3290-3302.
Heyl, A., Werner, T. and Schmülling, T., eds. (2006) Cytokinin metabolism and signal transduction. Oxford: Blackwell Publishing Ltd. 6: 480-88.
Higuchi, M., et al. (2004) Proc. Natl. Acad. Sci. USA, 101: 8821-8826.
Hiratsu, K., et al. (2003) Plant J, 34: 733-739.
Horák, J., et al. (2003) Plant Biol., 5: 245-254.
Hosoda, K., et al. (2002) Plant Cell, 14: 2015-2029.
Hwang, I., et al. (2002) Plant Physiol., 129: 500-515.
Hwang, I. and Sakakibara, H. (2006) Planta, 126: 528-538.
Hwang, I. and Sheen, J. (2001) Nature, 413: 383-389.
Imamura, A., et al. (2003) Plant Cell Physiol., 44: 122-131.
Kakimoto, T. (2003) Annu. Rev. Plant Biol., 54: 605-627.
Karimi, M., et al. (2002). Trends Plant Sci. 7: 193-195.
Sakai, H. et al. (2001) Science, 294: 1519-1521.
Kirby, J., and Kavanagh, T.A. (2002) Plant J. 32: 391-400.
Kumar, S., et al. (2004). Brief Bioinform. 5: 150-163.
Larsen, P.B. and Chang, C. (2001) Plant Physiol, 125: 1061-1073.
Lohrmann, J., et al. (2001). Mol. Genet. Genomics, 265: 2-13.
Makino, S., et al. (2000). Plant Cell Physiol. 41: 791-803.
Mason, M.G., et al. (2004) Plant Physiol., 135: 927-937.
Mason, M.G., et al. (2005) Plant Cell, 17: 3007-3018.
Minet, M., et al. (1992) Plant J, 2: 417-422.
Mizuno, T. (2004) Curr. Opin. Plant Biol., 7: 499-505.
Mok, D.W. and Mok, M.C. (2001) Annu. Rev. Plant Physiol. Plant Mol. Biol., 52: 89-118.
Nishimura, C., et al. (2004) Plant Cell, 16: 1365-1377.
Ohta, M., et al. (2001) Plant Cell, 13: 1959-1968.
Porra, R.J., et al. (1989) D. Biochcim Biophys Acta, 975: 384-394.
Rashotte, A.M., et al. (2006) Proc Natl Acad Sci USA, 103: 11081-11085.
Richmond, A.E. and Lang, A. (1957) Science (Washington D C), 125: 650.
Riechmann, J.L., et al. (2000) Science (Washington D C), 290: 2105-2110.
Riefler, M., et al. (2006) Plant Cell, 18: 40-54.
Romanov, G.A., et al. (2002) FEBS Lett., 515: 39-43.
Sakai, H., et al. (2000) Plant J, 24: 703-711.
Smalle, J., et al. (1997) Proc Natl Acad Sci USA, 94: 2756-2761.
Sprenger-Haussels, M., and Weisshaar, B. (2000). Plant J. 22: 1-8.
Sweere, U., et al. (2001) Science, 294: 1108-1111.
Tajima, Y., et al. (2004) Plant Cell Physiol., 45: 28-39.
Takada, S., et al. (2001) Development, 128: 1127-1135.
Thompson, J.D., et al. (1994) Nucleic Acids Res., 22: 4673-4680.
Tiwari, S.B., et al. (2004) Plant Cell, 16: 533-543.
To, J.P., et al. (2004) Plant Cell, 16: 658-671.
Werner, T., et al. (2003) Plant Cell, 15: 2532-2550.
Ellis et al., (1987) EMBO Journal, 6(1): 11-166.
Kadonaga, J.T. & Tjian, R. (1986) Proc. Natl. Acad. Sci. USA, 83, pp. 5889-5893.
Brudno M., (2003) Bioinformatics, 19 Suppl 1:I54-I62.
Raikhel, N. (1992) Nuclear targeting in plants. Plant Phys. 100. 1627-1632.
Wang et el. (1987) Science, 235: 587-591.
Peralta et al. (1986) EMBO Journal, 5(6):1137-1142.
van Haaren et al. (1987) Nucleic Acid Research, 15(21):8983-8997.
Hanson et al. (1999) The Plant Journal, 19 ( ):727-734.
Long, J.A., Ohno, C., Smith, Z.R. and Meyerowitz, E.M. (2006) Science 312, 1520-1523.
He J.X. et al. (2005) Science 307(5715), pp. 1634-1638.
Czarnecka-VernerE. et al. (2004) Plant Mol. Biol. 56(1), pp. 57-75.
Kim et al., (2006) PNAS, 103(3): 814-819.
Siemens et al., Mol. Plant Mic. Interact. 19, 480-494, 2006.
Zimmermann et al., (2004) Plant Physiol. 136, 2621-2632.
Hanahan, D. (1983) J. Mol. Biol. 166, 557-580.
Krens, F.A. et al (1982) Nature 296, 72-74.
Paszkowski J. et al. (1984) EMBO J. 3, 2717-2722.
Armstrong C.L. et al. (1990) Plant Cell Reports 9, 335-339.
Fromm et al., (1985) PNAS, 82(17): 5824-5828.
Crossway A. et al. (1986) Mol. Gen. Genet. 2002, 179-185.
Christou et al. (1988) Plant Physiol. 87, 671-674.
Sanford, (1988) TIBTECH, 6:299-302.
An G. et al. (1985) EMBO J. 4, 277-284.
Dodds, J.H. "Plant genetic engineering" Cambridge University Press, pp. 1-10.
Wang et al., (1997) The Plant Cell, 9: 491-507.
Herrera-Estrella et al., "Chimeric genes as dominant selectable markers in plant cell," EMBO J. 2(6):987-95 (1983).

\* cited by examiner

TRANSCRIPTIONAL REPRESSORS OF CYTOKININ SIGNALING AND THEIR USE

CROSS REFERENCE

This application is a U.S. National Phase Application of PCT/EP2007/008331, filed Sep. 25, 2007, which claims priority to U.S. Provisional Application No. 60/846,967 filed Sep. 25, 2006.

FIELD OF THE INVENTION

The invention relates to fusion proteins capable of acting as transcriptional repressors of cytokinin signaling, to polynucleotides encoding these fusion proteins, to vectors and cells comprising these polynucleotides, and to transgenic plants and parts thereof comprising these polynucleotides, vectors, and cells.

The invention further relates to a process for making these transgenic plants and to the use of these transgenic plants for producing seeds of enhanced size, with enhanced seed filling, with reduced seed loss and/or with more rapid germination, and/or for producing a live root system with increased root mass, root length and/or root branching. The invention also relates to a method for enhancing the seed size, for enhancing seed filling, for reducing seed loss, and/or for reducing germination time and/or reproduction time, and/or for enhancing the root mass, root length and/or root branching of a plant and to seeds obtainable by the methods of the present invention.

BACKGROUND OF THE INVENTION AND STATE OF THE ART

Cytokinin Signaling

The plant hormone cytokinin is involved in many developmental processes and plays a critical role in numerous physiological responses to changes in the environment (Mok and Mok, 2001). In recent years significant progress has been made towards the understanding of how the cytokinin signal is perceived and transduced (Ferreira and Kieber, 2005; Grefen and Harter, 2004; Heyl et al., 2006; Hwang et al., 2002; Hwang and Sakakibara, 2006; Kakimoto, 2003; Mizuno, 2004). In the current model, which has been mainly developed in *Arabidopsis*, the hormone is perceived by membrane-bound hybrid histidine kinase receptors (AHKs), which auto-phosphorylate upon binding of the hormone ligand. After trans-phosphorylation within the receptor, the phosphoryl residue is transferred to a histidine phosphotransfer protein (AHPs), which subsequently locates to the nucleus, where it activates B-type response regulators (ARRs) via phosphorylation. These transcription factors activate the transcription of their target genes, one group of which are the A-type response regulators. A negative feedback on the cytokinin signaling pathway was shown to be mediated by members of this protein class (Hwang and Sheen, 2001; To et al., 2004).

B-type response regulators are characterized by the presence of Myb-class DNA binding domain, called GARP domain, in addition to the response regulator domain. Several experiments have shown that B-type ARRs can bind to DNA and activate the transcription of their target genes in response to cytokinin treatment (Hosoda et al., 2002; Hwang and Sheen, 2001; Imamura et al., 2003; Lohrmann et al., 2001; Sakai et al., 2000). RT-PCR and promoter-GUS fusion experiments have demonstrated that the members of the B-type ARR family have large and overlapping expression domains (Mason et al., 2005; Tajima et al., 2004). The analysis of B-type ARR mutants has revealed their involvement in cytokinin signaling, but also a high level of functional redundancy (Hass et al., 2004; Horák et al., 2003; Mason et al., 2005; Sakai et al., 2001). Mason et al. (2005) studied single, double and triple mutants of ARR1, ARR2, ARR10 and ARR12 in various combinations (Mason et al., 2005). Different cytokinin response assays showed an increasing cytokinin resistance for higher order mutants. Surprisingly, beside a longer primary root in some mutants no strong morphological alterations were detected, which would be expected in case of a strong reduction of the cytokinin responsiveness. This could indicate that the degree of redundancy among B-type ARRs is even higher and/or that other transcription factors compensate for the loss of B-type ARRs. One other family of transcription factors which has recently been shown to be involved in mediating a cytokinin response are the cytokinin response factors (CRF)(Rashotte et al., 2006).

Chimeric Repressor Silencing Technology

The chimeric repressor silencing technology (CRES-T) has been developed to study the consequences of silencing the target genes of transcription factors and has also been used to overcome the experimental limitations caused by functional redundancy of transcription factor families. In 2001 Ohta and colleagues mapped a repression motif of transcriptional repressors of the class II ethylene response factors (ERF) which is both necessary and sufficient for the repression activity of the protein (Ohta et al., 2001). This so-called ERF-associated Amphiphilic Repression (EAR) motif or variations of it are found in numerous plant transcriptional repressors (Kazan, 2006; Ohta et al., 2001; Tiwari et al., 2004). The length and the repression potential of the EAR motif were improved resulting in the so-called SRDX motif (Hiratsu et al., 2003). Fusion of this motif to transcriptional activators converts them into dominant repressors (Hiratsu et al., 2003). Interestingly, these dominant repressors may repress not only the transcription of their own target genes, but also the expression of target genes of other members of their respective gene family. For example, the CUC1 and CUC2 transcription factors are functionally redundant and a loss of function phenotype is seen only in the cuc1 cuc2 double mutant plants, while mutation of both single genes does not cause a phenotype (Aida et al., 1997; Takada et al., 2001). The transgenic expression of a chimeric CUC1-SRDX gene induced the compound phenotype of a cuc1,cuc2 double mutant, demonstrating that its dominant-negative function encompassed CUC1 and CUC2 target genes (Hiratsu et al., 2003). The technology has not yet been used to investigate transcription factor gene families with numerous members.

TECHNICAL PROBLEM OF THE INVENTION

The technical problem underlying the instant invention is to provide a method for making seeds of enhanced size, with more rapid germination, with enhanced yield, with reduced seed loss and/or enhanced seed filling, and for making plants with enhanced root branching, root length, root mass and/or with better timing of reproduction, thereby, however, avoiding disadvantageous phenotype features.

SUMMARY OF THE INVENTION

In a first aspect, the present invention relates to a fusion protein comprising, essentially consisting or consisting of
(a) a DNA binding factor capable of specifically binding to a B-type *Arabidopsis* response regulator (ARR) DNA motif, the DNA motif comprising the sequence 5'-(A/G)GAT(T/C)-3'; and (b) a transcriptional repressor domain.

In a second aspect, the present invention relates to a fusion protein comprising, essentially consisting or consisting:
(a) a DNA binding factor comprising a DNA binding domain of a B-type ARR; and
(b) a transcriptional repressor domain.

In a third aspect, the present invention relates to a polynucleotide comprising a nucleic acid sequence encoding said fusion protein, a vector comprising said polynucleotide, a cell comprising said polynucleotide or said vector, and a transgenic plant comprising said polynucleotide, said vector, or said cell. The invention is further directed to parts, cells, or seeds of said transgenic plant, and to plants or propagating material thereof regenerated from said transgenic plant, parts, cells or seeds.

In a fourth aspect, the present invention is directed to a process for making the above transgenic plant, parts, cells, seeds or propagating material, wherein the above vector is introduced in a gene technological manner into cells of a plant, wherein the cells are transformed.

In a fifth aspect, the present invention relates to the use of the above transgenic plant, parts, cells, seeds or propagating material for producing seeds of enhanced size, with enhanced seed filling, with reduced seed loss and/or with more rapid germination, wherein the transgenic plants are cultured under culturing conditions and the preferably mature seeds are harvested.

In a sixth aspect, the present invention relates to the use of the above transgenic plant, parts, cells, seeds or propagating material for producing a live root system with increased root mass, root length and/or root branching, wherein the transgenic plant is cultured under culturing conditions.

In a seventh aspect, the present invention is directed to the use of a transgenically expressed fusion protein as defined above for enhancing the seed size, the seed filling, the root mass, root length and/or the root branching and/or for reducing seed loss and/or germination time of a plant.

In an eighth aspect, the present invention is directed to the use of a transgenically expressed fusion protein as defined above for modifying the characteristics of wood, for altering shoot architecture, for altering leaf senescence and other senescence processes and/or for altering the timing of reproduction.

In a ninth aspect, the invention relates to a method for enhancing the seed size, seed filling, the root mass, the root length and/or the root branching and/or for reducing seed loss and/or germination time of a plant, comprising the steps of
  introducing by genetic engineering into the plant a nucleic acid; and
  expressing said nucleic acid,
wherein the nucleic acid is the polynucleotide or the vector as defined above.

In a tenth aspect, the present invention relates to a method for making seeds of enhanced size, with enhanced seed filling, with reduced seed loss and/or with more rapid germination, wherein the transgenic plant, parts thereof, or seeds as described above are cultured under culturing conditions and preferably mature seeds being produced thereby are harvested.

In an eleventh aspect, the present invention is directed to seeds obtainable by any of the above methods.

In a twelfth aspect, the present invention relates to a method for making plants with increased root mass, root length and/or root branching and/or for reducing seed loss and or germination time of a plant, wherein the transgenic plant, parts, cells, seeds or propagating material as defined above are cultured under culturing conditions.

DETAILED DESCRIPTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

A "DNA binding factor" is to be understood as a polypeptide which is capable of binding in a sequence specific manner to DNA by virtue of a DNA binding domain. "DNA binding factors" are capable of making various contacts with the nucleotides in the major or minor groove of the DNA. Typically, DNA binding factors recognize sequence elements (DNA motifs) of 4 to 20 nucleotides in length. Many DNA binding factors only specifically recognize their respective DNA motif, if they homo- or heterodimerize. Thus, a "DNA binding factor" within the meaning of the present invention will preferably comprise both a DNA binding domain and a dimerization domain. Examples of such dimerization domains include without limitation so called leucine zippers or helix-loop-helix motifs (HLH). In the latter case the HLH is implicated in both dimerization and DNA recognition. The DNA binding factor preferably is devoid of any additional domain, e.g. activation domains, which are not required for sequence specific DNA binding. The term "DNA binding factor" encompasses isolated DNA-binding domains of DNA-binding proteins and also full length DNA binding proteins comprising further domains, such as the response regulator domain, as well as fragments and derivatives of such DNA binding proteins, provided that these fragments or derivatives are capable of sequence specific binding to DNA.

The expression "specifically binding" is to be understood within the context of the present application in that one polypeptide, e.g. a DNA binding factor, binds selectively to a target sequence within a nucleic acid, e.g. to a B-type ARR DNA motif, but not to other nucleotide sequences. Whether a polypeptide binds specifically or not to a target sequence can be determined by methods well-known to the person skilled in the art, such as band-shift assays, DNA protection assays, DNA footprinting etc.

A "DNA binding domain" is that region of a DNA-binding factor which directly interacts with the DNA and, thereby, mediates sequence specific binding to the DNA. The amino acid sequences of preferred DNA-binding domains of the invention are shown in FIG. 1(a).

A "B-type *Arabidopsis* response regulator (ARR) DNA motif" is that region on a DNA sequence to which the DNA binding factor or the DNA binding domain of the present invention is capable to bind. The DNA motif found optimal for binding of B-type ARRs is 5'-(A/G)GAT(T/C)-3' with the GAT motif in the middle being of special importance (Sakai H. et al. Arabidopsis ARR1 and ARR2 response regulators operate as transcriptional activators. Plant J 2000, 24:703-711; Hosoda K. et al.: Molecular structure of the GARP family of plant Myb-related DNA binding motifs of the Arabidopsis response regulators. Plant Cell 2002, 14:2015-2029). 5'-AGATT-3' was found to be optimal for ARR1, ARR2 and ARR10 (Sakai et al. 2000; Hosoda et al. 2002), whereas 5'-GGATT-3' was found for ARR11 (Imamura A. et al.: In vivo and in vitro characterization of the ARR 11 response regulator implicated in the His-Asp phosphorelay signal transduction in *Arabidopsis thaliana*. Plant Cell Phys 2003, 44:122-131). It is further considered within the present invention that additional DNA sequences close by could be involved in regulation and mediate specificity. Thus, in a preferred embodiment a B-type *Arabidopsis* response regulator comprises 1, 2, 3, 4, 5, or 6 additional nucleotides 5' and/or 3' of the core motif 5'-(A/G)GAT(T/C)-3' which can be derived from the promoter of an ARR regulated gene, i.e. from the sequences naturally flanking the core element 5' and/or 3'. Preferred examples of such promoters and elements are described in Sakai H. et al. (2000) supra and Hosoda K. et al. (2002) supra. The person skilled in the art is well aware of techniques allowing to isolate other proteins binding specifically to the "B-type ARR DNA motif". Methods for the isolation of sequence-specific DNA binding proteins include affinity purification (Kadonaga, J. T. & Tjian, R. 1986) Proc. Natl. Acad. Sci. USA, 83, pp. 5889-5893). It is also considerer within the present invention that some B-type ARRs may not bind to the above-mentioned consensus sequence 5'-(A/G)GAT(T/C)-3' but to other DNA sequences. Also such B-type ARRs binding to DNA sequences other than 5'-(A/G)GAT(T/C)-3' or DNA binding domains thereof can be used as a DNA binding factor according to the present invention provided that these B-type ARRs take part in cytokinin signaling and/or are homologous to the B-type response regulators set forth herein, especially to the B-type response regulators having the amino acid sequences as set forth in SEQ ID NOs: 12 to 50.

The term "transcriptional repressor domain" is to be understood as a polypeptide which is capable of achieving transcriptional repression when fused to a DNA binding factor or DNA binding domain. Transcriptional repression can be measured as the reduction of the expression of a reporter gene, e.g. luciferase, in a reporter gene assay. A "transcriptional repressor domain" within the meaning of the present invention is capable of reducing the expression of such a reporter gene by at least 10%, preferably by at least 20%, preferably by at least 30%, preferably by at least 40%, preferably by at least 50%, preferably by at least 60%, preferably by at least 70%, preferably by at least 80%, preferably by at least 90%, more preferably by at least 95%, even more preferably by at least 98% or most preferably by at least 99%.

"Homologs" are defined herein as two nucleic acids or polypeptides that have similar, or "homologous", nucleotide or amino acid sequences, respectively. Homologs within the meaning of the present application are to be understood as naturally occurring nucleic acids or polypeptides. Homologs include allelic variants, orthologs, and paralogs. In a narrow sense, two nucleic acids or polypeptides are considered homologs, if they share a common evolutionary ancestry. Within the context of the present application two nucleic acids or polypeptides are also considered "homologs" if they share a certain degree of sequence identity regardless whether said two nucleic acids or polypeptides share a common ancestry or not. More precisely, two nucleic acids or polypeptides shall be considered as homologs, if they exhibit at least 30% sequence identity, preferably at least 40% sequence identity, preferably at least 50% sequence identity, more preferably at least 60% sequence identity, more preferably at least 70% sequence identity, more preferably at least 80% sequence identity, even more preferably at least 90% sequence identity, and most preferably at least 95% sequence identity. Preferably, the homologs of the present invention exhibit the indicated homology, i.e. identity, and preferably the homology is over a continuous stretch of 20, 30, 40, 45, 50, 60, 70, 80, 90, 100 or more amino acids or the respective encoding nucleic acids, i.e. 60, 90, 120, 135, 150, 180, 210, 240, 270, 300 or more. Preferably, the continuous stretch of homologous amino acids spans the DNA binding domain or the DNA binding domain and the dimerization domain. The similarity of nucleotide and amino acid sequences, i.e. the percentage of sequence identity, can be determined via sequence alignments. Such alignments can be carried out with several art-known algorithms, preferably with hmmalign (HMMER package) or with the CLUSTAL algorithm (Thompson, J. D., Higgins, D. G. & Gibson, T. J. (1994) Nucleic Acids Res. 22, 4673-80or on. Preferred parameters used are the default parameters. The grade of sequence identity(sequence matching) may be calculated using e.g. BLAST, BLAT or BlastZ (or BlastX). Preferably, sequence matching analysis may be supplemented by established homology mapping techniques like Shuffle-LAGAN (Brudno M., Bioinformatics 2003b, 19 Suppl 1:154-162) or Markov random fields. When percentages of sequence identity are calculated, these percentages are typically calculated in relation to the full length of the longer sequence.

The term "variant" is to be understood herein as a polypeptide which differs in comparison to the protein or protein domain from which it is derived by one or more changes in the amino acid sequence. The term "variant" and the term "derivative" are used interchangeably throughout this application. Typically a variant is constructed artificially, preferably by gene-technological means. Typically, the protein or protein domain from which the variant is derived is a wild-type protein or protein domain. However, the variants of the present invention may also be derived from homologs or from artificially constructed variants, provided that the variants of the DNA binding factor of the present invention are capable of specifically binding to a B-type ARR DNA motif, and provided that the variants of the repressor domain of the present invention are capable of achieving transcriptional repression when fused to a DNA binding factor. The changes in the amino acid sequence may be amino acid exchanges, insertions, deletions, N-terminal truncations, or C-terminal truncations, or any combination of these changes, which may occur at one or several sites. The amino acid exchanges may be conservative or non-conservative. In preferred embodiments, a DNA binding factor or a DNA binding domain of the present invention differs from the protein or domain from which it is derived at least by 1, 2, 3, 4, 5, 6, 7, 8, 9, 10, 15, 20, 25, 30, 35, 40, 45, 50, 55, 60, 65, 70, 75, 80, 85, 90, 95, 100 or more amino acid exchanges, preferably conservative amino acid changes. Likewise, in preferred embodiments a repressor domain of the present invention differs from the protein or domain from which it is derived at least by 1, 2, 3, 4, 5, 6, 7, 8, 9, 10, 15, 20, 25, 30, 35, 40, 45, 50, 55, 60, 65, 70, 75, 80, 85, 90, 95, 100 or more amino acid exchanges, preferably conservative amino acid changes. Variants may additionally or alternatively comprise deletions of amino acids, which may be N-terminal truncations, C-terminal truncations or internal deletions or any combination of these. Such a deletion variant may be naturally occurring or it may be constructed artificially, preferably by gene-technological means. Typically, the protein or protein domain from which the deletion variant is derived is a wild-type protein. However, the variants of the present invention carrying deletions may also be derived from homologs or from artificially constructed variants, provided that the deletion variants of the DNA binding factor of the present invention are capable of specifically binding to a B-type ARR DNA motif, and provided that the deletion variants of the repressor domain of the present invention are capable of achieving transcriptional repression when fused to a DNA binding factor. In preferred embodiments a fragment of the DNA binding factor of the present invention is derived from a B-Type ARR having the amino acid sequence as shown in any one of SEQ ID NOs: 12 to 22. In further preferred embodiments, a deletion variant of the DNA binding factor of the present invention comprises the DNA binding domain of a B-Type ARR having the amino acid sequence as shown in any one of SEQ ID NOs: 1 to 11. Preferably a fragment has a deletion of 1, 2, 3, 4, 5, 6, 7, 8, 9, 10, 15, 20, 25, 30, 35, 40, 45, 50, 55, 60, 65, 70, 75, 80, 85, 90, 95, 100 or more amino acids at its N-terminus and/or C-terminus. In preferred embodiments a variant of the DNA binding factor of the present invention is derived from a B-Type ARR having the amino acid sequence as shown in any one of SEQ ID NOs: 12 to 22. In further preferred embodiments, a variant of the DNA binding factor of the present invention is derived from the DNA binding domain of a B-Type ARR having the amino acid sequence as shown in any one of SEQ ID NOs: 1 to 11.

"Non-conservative substitutions" or "non-conservative amino acid exchanges" are defined as exchanges of an amino acid by another amino acid listed in a different group of the six standard amino acid groups shown below:
(1) hydrophobic: Met, Ala, Val, Leu, Ile;
(2) neutral hydrophilic: Cys, Ser, Thr;
(3) acidic: Asp, Glu;
(4) basic: Asn, Gln, H is, Lys, Arg;
(5) residues that influence chain orientation: Gly, Pro; and
(6) aromatic: Trp, Tyr, Phe.

Conservative substitutions are defined as exchanges of an amino acid by another amino acid listed within the same group of the six standard amino acid groups shown above.

The term "EAR motif" (ERF-associated Amphiphilic Repression motif) is a repression motif of transcriptional repressors of the class II ethylene response factors (ERF). The EAR motif or variations of it are found in numerous plant transcriptional repressors (Kazan, 2006; Ohta et al., 2001; Tiwari et al., 2004). The minimal consensus sequence of the EAR motif is the amino acid sequence DLELRL (SEQ ID NO: 51; Hiratsu K. et al. (2004) Identification of the minimal repression domain of SUPERMAN shows that the DLELRL hexapeptide is both necessary and sufficient for repression of transcription in Arabidopsis. BBRC 321. 172-178). An especially preferred embodiment of the EAR motif having improved repression potential is the so-called SRDX motif (SEQ ID NO: 52; (Hiratsu et al., 2003)).

The "nuclear localization signal" (NLS) usable in the present invention is not particularly limited, provided that the signal is capable of achieving transport of the polypeptide to which it is bound to the nucleus of a cell. Nuclear localization signals comprise inter alia: PKKKRKV (SEQ ID NO: 53), KIPIK (SEQ ID NO: 54), SPPKAVKRPAATKK-AGQAKKKKLDKEDES (SEQ ID NO: 55), MEEAVTMA-PAAVSSAVVGDPMEYNAILRRKLEEDLE (SEQ ID NO: 56), KKRARL VRNRESAQLS RQRKK (SEQ ID NO: 57). A non-limiting list of such nuclear localization signals can be found for example in: Raikhel, N. (1992) Nuclear targeting in plants. Plant Phys. 100. 1627-1632; which is incorporated herein by reference in its entirety. Nuclear localization signals which are especially well-suited in the fusion proteins of the present invention can be found in FIG. 2 on p. 1628 of Raikhel, N. (1992), supra.

Reference herein to a "promoter" is to be taken in its broadest context and includes the transcriptional regulatory sequences derived from a classical eukaryotic genomic gene, typically including the TATA box which is required for accurate transcription initiation, with or without a CCAAT box sequence and additional regulatory or control elements (e.g. upstream activating sequences, repressors, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences. The term "promoter" is also used to describe a synthetic or fusion molecule, or derivative which confers, activates or enhances expression of a nucleic acid molecule in a cell, tissue or organ. Promoters may contain additional copies of one or more specific regulatory elements, to further enhance expression and/or to alter the spatial expression and/or temporal expression of a nucleic acid molecule to which it is operatively linked. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits. In the context of the present invention, the promoter preferably is a plant-expressible promoter sequence. Promoters that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. The terms "plant-operative" and "operative in a plant" when used herein, in respect of a promoter sequence, shall be taken to be equivalent to a plant-expressible promoter sequence. Regulatable promoters as part of a binary viral plant expression system are also known to the skilled artisan (Yadav 1999—WO 99/22003; Yadav 2000—WO 00/17365).

In the present context, a "regulatable promoter sequence" is a promoter that is capable of conferring expression of a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression of a gene to which it is operatively linked in a particular location within the plant or alternatively, throughout the plant under a specific set of conditions, such as following induction of gene expression by a chemical compound or other elicitor. Preferably, the regulatable promoter used in the performance of the present invention confers expression in a specific location within the plant, either constitutively or following induction, however, not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon). Similarly, the term "tissue-specific" shall be taken to indicate that expression is predominantly in a particular tissue or tissue-type, preferably of plant origin, albeit not necessarily exclusively in said tissue or tissue-type. Similarly, the term "organ-specific" shall be taken to indicate that expression is predominantly in a particular organ, preferably of plant origin, albeit not necessarily exclusively in said organ. Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin. Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development. Those skilled in the art will readily be capable of selecting appropriate promoter sequences for use in regulating appropriate expression of the fusion protein from publicly-available sources, without undue experimentation. Placing a nucleic acid molecule under the regulatory control of a promoter sequence, or in operative connection or linkage with a promoter sequence, means positioning said nucleic said molecule such that expression is controlled by the promoter sequence. A promoter is usually, but not necessarily, positioned upstream, or at the 5'-end, and within 2 kb of the start site of transcription, of the nucleic acid molecule which it regulates, albeit enhancers and silencers, which are also comprised by the term "promoter" may be placed further away from the transcriptional start site. It is thought that these elements bind to proteins capable of long range action due to looping out of the intervening sequence. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur. Examples of promoters suitable for use in gene constructs of the present invention include those listed in Table 1, amongst others. Table 1 consists of three parts marked with Roman numbers I, III and IV.

TABLE 1

Promoters usable in the invention.

I: CELL-SPECIFIC, TISSUE-SPECIFIC, AND ORGAN-SPECIFIC PROMOTERS

| GENE SOURCE | EXPRESSION PATTERN | REFERENCE |
| --- | --- | --- |
| α-amylase (Amy32b) | aleurone | Lanahan, M. B., et al., Plant Cell 4: 203-211, 1992; Skriver, K., et al. Proc. Natl. Acad. Sci. (USA) 88: 7266-7270, 1991 |
| cathepsin β-like gene | aleurone | Cejudo, F. J., et al. Plant Molecular Biology 20: 849-856, 1992. |
| *Agrobacterium rhizogenes* rolB | cambium | Nilsson et al., Physiol. Plant. 100: 456-462, 1997 |
| AtPRP4 | flowers | |
| chalcone synthase (chsA) | flowers | Van der Meer, et al., Plant Mol. Biol 15, 95-109, 1990. |
| LAT52 | anther | Twell et al. Mol. Gen Genet. 217: 240-245 (1989) |
| apetala-3 | flowers | |
| chitinase | fruit (berries, grapes, etc.) | Thomas et al. CSIRO Plant Industry, Urrbrae, South Australia, Australia; |
| rbcs-3A | green tissue (eg leaf) | Lam, E. et al., The Plant Cell 2: 857-866, 1990; Tucker et al., Plant Physiol 113: 1303-1308, 1992. |
| leaf-specific genes | leaf | Baszczynski, et al., Nucl. Acid Res. 16: 4732, 1988. |
| AtPRP4 | leaf | |
| chlorella virus adenine methyltransferase gene promoter | leaf | Mitra and Higgins, 1994, Plant Molecular Biology 26: 85-93 |
| aldP gene promoter from rice | leaf | Kagaya et al., 1995, Molecular and General Genetics 248: 668-674 |
| rbcs promoter from rice or tomato | leaf | Kyozuka et al., 1993, Plant Physiology 102: 991-1000 |
| *Pinus* cab-6 | leaf | Yamamoto et al., Plant Cell Physiol. 35: 773-778, 1994. |

TABLE 1-continued

Promoters usable in the invention.

| | | |
|---|---|---|
| rubisco promoter | leaf | |
| cab (chlorophyll a/b/binding protein) | leaf | |
| SAM22 | senescent leaf | Crowell, et al., Plant Mol. Biol. 18: 459-466, 1992. |
| ltp gene (lipid transfer gene) | | Fleming, et al., Plant J. 2, 855-862. |
| R. japonicum nif gene | Nodule | U.S. Pat. No. 4,803,165 |
| B. japonicum nifH gene | Nodule | U.S. Pat. No. 5,008,194 |
| GmENOD40 | Nodule | Yang, et al., The Plant J. 3: 573-585. |
| PEP carboxylase (PEPC) | Nodule | Pathirana et al., Plant Mol. Biol. 20: 437-450, 1992. |
| leghaemoglobin (Lb) | Nodule | Gordon, et al., J. Exp. Bot. 44: 1453-1465, 1993. |
| Tungro bacilliform virus gene | phloem | Bhattacharyya-Pakrasi, et al., The Plant J. 4: 71-79, 1992. |
| pollen-specific genes | pollen; microspore | Albani, et al., Plant Mol. Biol. 15: 605, 1990; Albani, et al., Plant Mol. Biol. 16: 501, 1991) |
| Zm13 | pollen | Guerrero et al Mol. Gen. Genet. 224: 161-168 (1993) |
| apg gene | microspore | Twell et al. Sex. Plant Reprod. 6: 217-224 (1993) |
| maize pollen-specific gene | pollen | Hamilton, et al., Plant Mol. Biol. 18: 211-218, 1992. |
| sunflower pollen-expressed gene | pollen | Baltz, et al., The Plant J. 2: 713-721, 1992. |
| B. napus pollen-specific gene | pollen; anther; tapetum | Arnoldo, et al., J. Cell. Biochem., Abstract No. Y101, 204, 1992. |
| root-expressible genes | roots | Tingey, et al., EMBO J. 6: 1, 1987. |
| tobacco auxin-inducible gene | root tip | Van der Zaal, et al., Plant Mol. Biol. 16, 983, 1991. |
| β-tubulin | root | Oppenheimer, et al., Gene 63: 87, 1988. |
| tobacco root-specific genes | root | Conkling, et al., Plant Physiol. 93: 1203, 1990. |
| B. napus G1-3b gene | root | U.S. Pat. No. 5,401,836 |
| SbPRP1 | roots | Suzuki et al., Plant Mol. Biol. 21: 109-119, 1993. |
| AtPRP1; AtPRP3 | roots; root hairs | |
| RD2 gene | root cortex | |
| TobRB7 gene | root vasculature | |
| AtPRP4 | leaves; flowers; lateral root primordia | |
| seed-specific genes | seed | Simon, et al., Plant Mol. Biol. 5: 191, 1985; Scofield, et al., J. Biol. Chem. 262: 12202, 1987; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al., Plant Mol Biol, 14(3): 323-32, 1990 |
| napA | seed | Stalberg, et al., Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al., Plant Cell, 9: 171-184, 1997 |
| wheat α, β, γ-gliadins | endosperm | EMBO 3: 1409-15, 1984 |
| barfey ltr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al., The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al., Plant Cell Physiology 39(8) 885-889, 1998 |
| rice α-globulin Glb-1 | endosperm | Wu et al., Plant Cell Physiology 39(8) 885-889, 1998 |
| rice OSH1 | embryo | Sato et al., Proc. Natl. Acad. Sci. USA, 93: 8117-8122, 1996 |
| rice α-globulin REB/OHP-1 | endosperm | Nakase et al., Plant Mol. Biol. 33: 513-522, 1997 |
| rice ADP-glucose PP | endosperm | Trans Res 6: 157-68, 1997 |

TABLE 1-continued

Promoters usable in the invention.

| | | |
|---|---|---|
| maize ESR gene family | endosperm | Plant J 12: 235-46, 1997 |
| sorgum γ-kafirin | endosperm | PMB 32: 1029-35, 1996 |
| KNOX | embryo | Postma-Haarsma, et al., Plant Mol. Biol. 39: 257-71, 1991 |
| rice oleosin | embryo and aleuron | Wu et al., J. Biochem., 123: 386, 1998 |
| sunflower oleosin | seed (embryo and dry seed) | Cummins, et al., Plant Mol. Biol. 19: 873-876, 1992 |
| LEAFY | shoot meristem | Weigel et al., Cell 69: 843-859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah, et al., Proc. Natl. Acad. Sci. USA 85: 5551, 1988; Trick, et al., Plant Mol. Biol. 15: 203, 1990. |
| class I patatin gene | tuber | Liu et al., Plant Mol. Biol. 153: 386-395, 1991. |
| PCNA rice | meristem | Kosugi et al., Nucleic Acids Research 19: 1571-1576, 1991; Kosugi S. and Ohashi Y., Plant Cell 9: 1607-1619, 1997. |
| Pea TubA1 tubulin | Dividing cells | Stotz and Long, Plant Mol Biol. 41, 601-614, 1999 |
| *Arabidopsis* cdc2a | cycling cells | Chung and Parish, FEBS Lett, 3: 362(2): 215-9, 1995 |
| *Arabidopsis* Rop1A | Anthers; mature pollen + pollen tubes | Li et al. 1998 Plant Physiol 118, 407-417. |
| *Arabidopsis* AtDMC1 | Meiosis-associated | Klimyuk and Jones 1997 Plant J. 11, 1-14. |
| Pea PS-IAA4/5 and PS-IAA6 | Auxin-inducible | Wong et al., 1996 Plant J. 19, 587-599. |
| Pea farnesyltransferase | Meristematic tissues; phloem near growing tissues; light- and sugar-repressed | Zhou et al., 1997 Plant J. 12, 921-930 |
| Tobacco (*N. sylvestris*) cyclin B1; 1 | Dividing cells/ meristematic tissue | Trehin et al. 1997 Plant Mol. Biol. 35, 667-672. |
| *Catharanthus roseus* Mitotic cyclins CYS (A-type) and CYM (B-type) | Dividing cells/ meristematic tissue | Ito et al. 1997 Plant J. 11, 983-992 |
| *Arabidopsis* cyc1At (=cyc B1; 1) and cyc3aAt (A-type) | Dividing cells/ meristematic tissue | Shaul et al. 1996 Proc. Natl. Acad. Sci. U.S.A. 93, 4868-4872. |
| *Arabidopsis* tef1 promoter box | Dividing cells/ meristematic tissue | Regad et al. 1995 Mol. Gen. Genetic. 248, 703-711. |
| *Catharanthus roseus* cyc07 | Dividing cells/ meristematic tissue | Ito et al. 1994 Plant Mol Biol 24, 863-878. |

| III: EXEMPLARY STRESS-INDUCIBLE PROMOTERS | | |
|---|---|---|
| NAME | STRESS | REFERENCE |
| P5CS (delta(1)-pyrroline-5-carboxylate syntase) | salt, water | Zhang et al. Plant Science. 129: 81-89, 1997 |
| cor15a | cold | Hajela et al., Plant Physiol. 93: 1246-1252, 1990 |
| cor15b | cold | Wlihelm et al., Plant Mol Biol. 23: 1073-1077, 1993 |
| cor15a (−305 to +78 nt) | cold, drought | Baker et al., Plant Mol Biol. 24: 701-713, 1994 |
| rd29 | salt, drought, cold | Kasuga et al., Nature Biotechnology 18: 287-291, 1999 |
| heat shock proteins, including artificial promoters containing the heat shock element (HSE) | heat | Barros et al., Plant Mol Biol 19: 665-75, 1992. Marrs et al., Dev Genet. 14: 27-41, 1993. Schoffl et al., Mol Gen Gent, 217: 246-53, 1989. |
| smHSP (small heat shock proteins) | heat | Waters et al., J Experimental Botany 47: 325-338, 1996 |
| wcs120 | cold | Ouellet et al., FEBS Lett. 423: 324-328, 1998 |
| ci7 | cold | Kirch et al., Plant Mol Biol 33: 897-909, 1997 |
| Adh | cold, drought, hypoxia | Dolferus et al., Plant Physiol 105: 1075-87, 1994 |
| pwsl18 | water; salt and drought | Joshee et al., Plant Cell Physiol 39: 64-72, 1998 |
| ci21A | cold | Schneider et al., Plant Physiol 113: 335-45, 1997 |
| Trg-31 | drought | Chaudhary et al., Plant Mol Biol 30; 1247-57, 1996 |
| osmotin | osmotic | Raghothama et al., Plant Mol Biol 23: 1117-28, 1993 |

TABLE 1-continued

Promoters usable in the invention.

| | | |
|---|---|---|
| Rab17 | osmotic, ABA | Vilardell et al., Plant Mol Biol 17: 985-93, 1991 |
| lapA | wounding, environmental | WO99/03977 University of California/INRA |

| IV: EXEMPLARY PATHOGEN-INDUCIBLE PROMOTERS | | |
|---|---|---|
| NAME | PATHOGEN | REFERENCE |
| RB7 | Root-knot nematodes (*Meloidogyne* spp.) | U.S. Pat. No. 5,760,386 - North Carolina State University; Opperman et al. (1994) Science 263: 221-23. |
| PR-1, 2, 3, 4, 5, 8, 11 | fungal, viral, bacterial | Ward et al. (1991) Plant Cell 3: 1085-1094; Reiss et al. 1996; Lebel et al. (1998), Plant J, 16(2): 223-33; Melchers et al (1994), Plant J, 5(4): 469-80; Lawton et al (1992), Plant Mol Biol, 19(5): 735-43. |
| HMG2 | nematodes | WO9503690 - Virginia Tech Intellectual Properties Inc. |
| Abi3 | Cyst nematodes (*Heterodera* spp.) | Unpublished |
| ARM1 | nematodes | Barthels et al., (1997) The Plant Cell 9, 2119-2134. WO 98/31822 - Plant Genetic Systems |
| Att0728 | nematodes | Barthels et al., (1997) The Plant Cell 9, 2119-2134. PCT/EP98/07761 |
| Att1712 | nematodes | Barthels et al., (1997) The Plant Cell 9, 2119-2134. PCT/EP98/07761 |
| Gst1 | Different types of pathogens | Strittmatter et al. (1996) Mol. Plant-Microbe Interact. 9, 68-73. |
| LEMMI | nematodes | WO 92/21757 - Plant Genetic Systems |
| CLE | geminivirus | PCT/EP99/03445 - CINESTAV |
| PDF1.2 | Fungal including *Alternaria brassicicola* and *Botrytis cinerea* | Manners et al. (1998), Plant Mol Biol, 38(6): 1071-80. |
| Thi2.1 | Fungal - *Fusarium oxysporum* f sp. *matthiolae* | Vignutelli et al. (1998) Plant J; 14(3): 285-95 |
| DB#226 | nematodes | Bird and Wilson (1994) Mol. Plant-Microbe Interact., 7, 419-42 WO 95.322888 |
| DB#280 | nematodes | Bord and Wilson (1994) Mol. Plant-Microbe Interact., 7, 419-42 WO 95.322888 |
| Cat2 | nematodes | Niebel et al. (1995) Mol Plant Microbe Interact 1995 May-June; 8(3): 371-8 |
| ☐Tub | nematodes | Aristizabal et al. (1996) 8$^{th}$ International Congress on Plant-Microbe Interaction, Knoxville US B-29 |
| SHSP | nematodes | Fenoll et al. (1997) In: Cellular and molecular aspects of plant-nematode interactions. Kluwer Academic, C. Fenoll, F. M. W. Grundler and S. A. Ohl (Eds.) |
| Tsw12 | nematodes | Fenoll et al. (1997) In: Cellular and molecular aspects of plant-nematode interactions. Kluwer Academic, C. Fenoll, F. M. W. Grundler and S. A. Ohl (Eds.) |
| Hs1(pro1) | nematodes | WO 98/122335 - Jung |
| NsLTP | viral, fungal, bacterial | Molina & García-Olmedo (1993) FEBS Lett, 316(2): 119-22 |
| RIP | viral, fungal | Turner et al. (1997) Proc Natl Acad Sci USA, 94(8): 3866-71 |

The promoters listed in Table 1 are provided for the purposes of exemplification only and the present invention is not to be limited by the list provided therein. Those skilled in the art will readily be in a position to provide additional promoters that are useful in performing the present invention. In the case of constitutive promoters or promoters that induce expression throughout the entire plant, it is preferred that such sequences are modified by the addition of nucleotide sequences derived from one or more of the tissue-specific promoters listed in Table 1, or alternatively, nucleotide sequences derived from one or more of the above-mentioned tissue-specific inducible promoters, to confer tissue-specificity thereon. For example, the CaMV 35S promoter may be modified by the addition of maize Adh1 promoter sequence, to confer anaerobically-regulated root-specific expression thereon, as described previously (Ellis et al., 1987). Another example describes conferring root specific or root abundant gene expression by fusing the CaMV35S promoter to elements of the maize glycine-rich protein GRP3 gene (Feix and Wulff 2000—WO 00/15662). Such modifications can be achieved by routine experimentation by those skilled in the art.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants. Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others. Preferred promoter sequences of the invention include root specific promoters such as but not limited to the ones listed in Table 1 and as outlined in the Examples. Those skilled in the art will be aware of additional promoter sequences and terminator sequences which may be suitable for use in performing the invention. Such sequences may readily be used without any undue experimentation.

The term "organogenesis", as used herein, means a process by which shoots and roots are developed sequentially from meristematic centres. The term "embryogenesis", as used herein, means a process by which shoots and roots develop together in a concerted fashion (not sequentially), whether from somatic cells or gametes.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* virgenes, nicked at the T-DNA borders and is transferred as a single stranded DNA to the nucleus of an eukaryotic cell. When used herein, with "T-DNA borders", "T-DNA border region", or "border region" are meant either right T-DNA border (LB) or left T-DNA border (LB). Such a border comprises a core sequence flanked by a border inner region as part of the T-DNA flanking the border and/or a border outer region as part of the vector backbone flanking the border. The core sequences comprise 22 by in case of octopine-type vectors and 25 by in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et el. 1987). One element enhancing T-DNA transfer has been characterized and resides in the right border outer region and is called overdrive (Peralta et al. 1986, van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell. With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats. The current invention includes optimized T-DNA vectors such that vector backbone integration in the genome of a eukaryotic cell is minimized or absent. With "optimized T-DNA vector" is meant a T-DNA vector designed either to decrease or abolish transfer of vector backbone sequences to the genome of a eukaryotic cell. Such T-DNA vectors are known to the one familiar with the art and include those described by Hanson et al. (1999) and in WO 99/01563. The current invention clearly considers the inclusion of a DNA sequence encoding a fusion protein in any T-DNA vector comprising binary transformation vectors, super-binary transformation vectors, co-integrate transformation vectors, bi-derived transformation vectors as well as in T-DNA carrying vectors used in agrolistic transformation.

With "binary transformation vector" is meant a T-DNA transformation vector comprising: (a) a T-DNA region comprising at least one gene of interest and/or at least one selectable marker active in the eukaryotic cell to be transformed; and (b) a vector backbone region comprising at least origins of replication active in *E. coli* and *Agrobacterium* and markers for selection in *E. coli* and *Agrobacterium*. The T-DNA borders of a binary transformation vector can be derived from octopine-type or nopaline-type Ti plasmids or from both. The T-DNA of a binary vector is only transferred to a eukaryotic cell in conjunction with a helper plasmid.

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pT1Bo542 of the super-virulent *A. tumefaciens* strain A281 (EP 0 604 662, EP 0 687 730). Super-binary transformation vectors arg used in conjunction with a helper plasmid.

With "co-integrate transformation vector" is meant a T-DNA vector at least comprising: (a) a T-DNA region comprising at least one gene of interest and/or at least one selectable marker active in plants; and (b) a vector backbone region comprising at least origins of replication active in *Escherichia coli* and *Agrobacterium*, and markers for selection in *E. coli* and *Agrobacterium*, and a set of vir genes necessary for enabling transfer of the T-DNA. The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a helper Ri-plasmid carrying the necessary set of vir genes.

As used herein, the term "selectable marker gene" or "selectable marker" or "marker for selection" includes any gene which confers a phenotype to a cell in which it is expressed to facilitate the identification and/or selection of cells which are transfected or transformed with a gene construct of the invention or a derivative thereof. Suitable selectable marker genes contemplated herein include the ampicillin resistance (Amp$^r$, tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene, and luciferase gene, amongst others.

With "agrolistics"; "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in plantal production of VirD1 and VirD2 with or without, VirE2 (WO9712046).

With "foreign DNA" is meant any DNA sequence that is introduced in the host's genome by recombinant techniques.

Said foreign DNA includes e.g. a T-DNA sequence or a part thereof such as the T-DNA sequence comprising the selectable marker in an expressible format. Foreign DNA furthermore includes intervening DNA sequences as defined supra or infra.

Embodiments of the Invention

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect, the present invention provides a fusion protein comprising, essentially consisting or consisting of:
(a) a DNA binding factor capable of specifically binding to a B-type *Arabidopsis* response regulator (ARR) DNA motif, the DNA motif comprising the sequence 5'-(A/G)GAT(T/C)-3'; and
(b) a transcriptional repressor domain.

In preferred embodiments the DNA binding factor comprises, essentially consists of or consists of a DNA binding domain.

In a second aspect, the present invention provides a fusion protein comprising, essentially consisting or consisting of:
(a) a DNA binding factor comprising a DNA binding domain of a B-type ARR; and
(b) a transcriptional repressor domain.

In preferred embodiments the DNA binding factor according to the second aspect is also a DNA binding factor according to the first aspect, i.e. in preferred embodiments the DNA binding factor comprises, essentially consists of or consists of a DNA binding domain of a B-type ARR and is capable of specifically binding to a B-type ARR DNA motif, the DNA motif comprising the sequence 5'-(A/G)GAT(T/C)-3'. In especially preferred embodiments, the DNA binding domain of the B-type ARR is capable of specifically binding to the DNA motif comprising the sequence 5'-(A/G)GAT(T/C)-3'.

In a preferred embodiment the DNA binding domain comprises, essentially consists or consists of the amino acid sequence $X_1X_2X_3WX_4X_5X_6LX_7X_8PKX_9X_{10}X_{11}X_{12}X_{13}X_{14}X_{15}X_{16}$ $X_{17}X_{18}X_{19}X_{20}X_{21}RX_{22}NVASHLQKX_{23}R$, wherein $X_1$ is selected from R or K, preferably R; $X_2$ is selected from V, I, or M, preferably V; $X_3$ is selected from V, L, Q, T or W, preferably V; $X_4$ is selected from S or T; $X_5$ is any amino acid, preferably V, H, I, Q, F, D, P, E, or N; $X_6$ is selected from E, S, or P, preferably E; $X_7$ is selected from H or Q, preferably H; $X_8$ is a stretch of 13 to 17 amino acids, i.e. 13, 14, 15, 16, or 17 amino acids, preferably independently from each other selected from A, C, D, E, F, G, H, I, K, L, M, N, Q, R, S, V, or Y; $X_9$ is selected from K, R, T or V, preferably K; $X_{10}$ is selected from I or L, preferably I; $X_{11}$ is selected from L or V, preferably L; $X_{12}$ is selected from D, A, E, or K, preferably D or E; $X_{13}$ is selected from L, M, F, C, I, or Y, preferably L; $X_{14}$ is selected from M or L, preferably M; $X_{15}$ is selected from N, Q, or S, preferably N; $X_{16}$ is a stretch of 0 to 4 amino acids, i.e. 1, 2, 3, or 4, preferably independently selected from E, L, M, N or R, preferably 0 amino acids; $X_{17}$ is selected from V or I, preferably V; $X_{18}$ is selected from P, D, E, or Q, preferably P; $X_{19}$ is selected from G, K, W, or Y, preferably G; $X_{20}$ is selected from L or I, preferably L; $X_{21}$ is selected from T or S, preferably T; $X_{22}$ is selected from E, N or S, preferably E; $X_{23}$ is selected from Y, F or H, preferably Y, and is capable of specifically binding to a B-type *Arabidopsis* response regulator. The ability of any of the preferred DNA binding domains to specifically bind to such an element can be assayed by any number of art known assay including band shift, transcriptional activation or repression assays. In a preferred embodiment $X_1$ is R; and/or $X_2$ is V; and/or $X_3$ is V; and/or $X_4$ is S or T; and/or $X_5$ is V, H, I, Q, F, D, P, E, or N; and/or $X_6$ is E; and/or $X_7$ is H; $X_8$ is a stretch of 13 to 17 amino acids, i.e. 13, 14, 15, 16, or 17 amino acids, preferably independently from each other selected from A, C, D, E, F, G, H, I, K, L, M, N, Q, R, S, V, or Y; and/or $X_9$ is K; and/or $X_{10}$ is I; and/or $X_{11}$ is L; and/or $X_{12}$ is D or E; and/or $X_{13}$ is L; and/or $X_{14}$ is M; and/or $X_{15}$ is N; and/or $X_{17}$ is V; and/or $X_{18}$ is P; and/or $X_{19}$ is G; and/or $X_{20}$ is L; and/or $X_{21}$ is T; and/or $X_{22}$ is E; and/or $X_{23}$ is Y.

In a further preferred embodiment of the fusion protein of the present invention the DNA binding domain is selected from the group of
(a) DNA binding domains of ARR1 according to SEQ ID NO: 1, ARR2 according to SEQ ID NO: 2, ARR10 according to SEQ ID NO: 3, ARR11 according to SEQ ID NO: 4, ARR12 according to SEQ ID NO: 5, ARR13 according to SEQ ID NO: 6, ARR14 according to SEQ ID NO: 7, ARR18 according to SEQ ID NO: 8, ARR19 according to SEQ ID NO: 9, ARR20 according to SEQ ID NO: 10, ARR21 according to SEQ ID NO: 11, APRR2 according to SEQ ID NO: 60, APRR4 according to SEQ ID NO: 61, or CCA1 according to SEQ ID NO: 62;
(b) a homologue of a DNA binding domain according to (a) from a plant other than *Arabidopsis thaliana* capable of specifically binding to a B-type ARR DNA motif; or
(c) a variant of a DNA binding domain according to (a) or (b) comprising one or more modifications selected from the group consisting of amino acid exchanges, amino acid insertions, amino acid deletions, N-terminal truncations and C-terminal truncations, wherein the variant is capable of specifically binding to a B-type ARR DNA motif.

In a further preferred embodiment of the fusion protein of the present invention the DNA binding factor is:
(a) selected from the group of B-type ARRs from *Arabidopsis thaliana* consisting of ARR1 according to SEQ ID NO: 12, ARR2 according to SEQ ID NO: 13, ARR10 according to SEQ ID NO: 14, ARR11 according to SEQ ID NO: 15, ARR12 according to SEQ ID NO: 16, ARR13 according to SEQ ID NO: 17, ARR14 according to SEQ ID NO: 18, ARR18 according to SEQ ID NO: 19, ARR19 according to SEQ ID NO: 20, ARR20 according to SEQ ID NO: 21, and ARR21 according to SEQ ID NO: 22;
(b) a homologue of a B-type ARR according to (a) from a plant other than *Arabidopsis thaliana* capable of specifically binding to a B-type ARR DNA motif; or
(c) a variant of a B-type ARR according to (a) or (b) comprising one or more modifications selected from the group consisting of amino acid exchanges, amino acid insertions, amino acid deletions, N-terminal truncations and C-terminal truncations capable of specifically binding to a B-type ARR DNA motif.

In a further preferred embodiment of the fusion protein of the present invention the DNA binding factor is:
(a) selected from the group of polypeptides consisting of APRR2 according to SEQ ID NO: 63, APRR4 according to SEQ ID NO: 64, and CCA1 according to SEQ ID NO: 65.
(b) a homologue of a polypeptide according to (a) from a plant other than *Arabidopsis thaliana* capable of specifically binding to a B-type ARR DNA motif; or
(c) a variant of a polypeptide according to (a) or (b) comprising one or more modifications selected from the group consisting of amino acid exchanges, amino acid insertions, amino acid deletions, N-terminal truncations and C-terminal truncations capable of specifically binding to a B-type ARR DNA motif.

In preferred embodiments, the "plant other than *Arabidopsis thaliana*" to which any of the above embodiments refer is a monocotyledonous plant or a dicotyledonous plant. It is also contemplated within the present invention that such "other plants" can be lower plants, e.g. mosses such as *Physcomitrella patens*. It is also considered that B-type ARRs from other plants and especially B-type ARRs from non-plant organisms may have other DNA binding specificities than B-type ARRs from *Arabidopsis thaliana*. In more preferred embodiments, the homolog of the DNA binding domain or the homolog of the B-type ARR protein is derived from *Oryza sativa, Zea mays, Catharanthus roseus, Medicago truncatula, Poncirus trifoliata, Vitis vinifera, Brassica rapa, Vitis shuttleworthii, Allium cepa, Phaseolus vulgaris, Citrus clementina, Solanum tuberosum, Sorghum bicolor, Pinus taeda* or *Populus deltoides*. In especially preferred embodiments of the present invention, the homolog of the B-type ARR protein is selected from response regulator proteins listed in table 2, and the homolog of the DNA binding domain is selected from the DNA binding domains of the response regulator proteins listed in Table 2.

In a preferred embodiment of the fusion protein of the present invention the transcriptional repressor domain is selected from the group consisting of an EAR motif, a paired amphipathic helix 3/histone deacetylase interaction domain (PAH3/HID), a histone deacetylase domain (Long, J. A., Ohno, C., Smith, Z. R. and Meyerowitz, E. M. (2006) TOPLESS regulates apical embryonic fate in *Arabidopsis*. Science 312, 1520-1523), an en[298] domain of ENGRAILED (Chandler, J. W. and Werr, W. (2003) When negative is positive in functional genomics. TIPS 8. 279-285), a repressor domain of BZR1 (He J. X. et al. (2005) BZR1 is a transcriptional repressor with dual roles in brassinosteroid homeostasis and growth response. Science 307 (5715), pp. 1634-1638), the repressor domain (RD) of the C-terminal regulatory region (CTR) of class B heat shock transcriptions factors (HSFs) (Czarnecka-VernerE. et al. (2004) Plant Mol. Biol. 56 (1), pp. 57-75), and domain I of Aux/IAA proteins (Tiwari S. B. et al. (2004) Plant Cell 16 (2), pp. 533-543).

In preferred embodiments of the invention the EAR motif comprises the sequence DLELRL (SEQ ID NO: 51) or a variant thereof having EAR motif repressor activity. The repressor activity of the EAR motif can be determined with methods known to the person skilled in the art, e.g. by reporter gene assays using luciferase as reporter gene. An EAR motif

TABLE 2

Non-limiting list of known response regulator protein sequences

| Organism | protein | Locus name or Accession number | SEQ ID NO: |
|---|---|---|---|
| Arabidopsis thaliana | ARR1 | At 3g16857 | 12 |
| Arabidopsis thaliana | ARR2 | At 4g16110 | 13 |
| Arabidopsis thaliana | ARR10 | At 4g31920 | 14 |
| Arabidopsis thaliana | ARR11 | At 1g67710 | 15 |
| Arabidopsis thaliana | ARR12 | At 2g25180 | 16 |
| Arabidopsis thaliana | ARR13 | At 2g27070 | 17 |
| Arabidopsis thaliana | ARR14 | At 2g01760 | 18 |
| Arabidopsis thaliana | ARR18 | At 5g58080 | 19 |
| Arabidopsis thaliana | ARR19 | At 1g49190 | 20 |
| Arabidopsis thaliana | ARR20 | At 3g62670 | 21 |
| Arabidopsis thaliana | ARR21 | At 5g07210 | 22 |
| Oryza sativa L. | Ehd1, B-type RR10 | AB092509 | 23 |
| Oryza sativa L | ORR1 B-type response regulator | AB246780 | 24 |
| Oryza sativa L. | ORR2 | AP007226 (Q5SML5) | 25 |
| Oryza sativa L | ORR3 | AP004094 | 26 |
| Oryza sativa L. | ORR4 | AP004087 | 27 |
| Oryza sativa L | ORR5 | AP004008 | 28 |
| Oryza sativa L. | ORR6 | AP006838 | 29 |
| Zea mays | ZMRR10 | AB071695 | 30 |
| Zea mays | ZMRR8 | AB060130 | 31 |
| Zea mays | ZMRR9 | AB062095 | 32 |
| Catharanthus roseus | RR5 | AF534891 | 33 |
| Medicago truncatula (barrel medic) | B-type ARR (EST) | mtru82397 | 34 |
| Poncirus trifoliata | B-type ARR (EST) | ptri1402 | 35 |
| Vitis vinifera (wine grape) | B-type ARR (EST) | vvin34184 | 36 |
| Medicago truncatula (barrel medic) | B-type ARR (EST) | mtru93971 | 37 |
| Brassica rapa (field mustard) | B-type ARR (EST) | brap8642 | 38 |
| Brassica rapa (field mustard) | B-type ARR (EST) | brap313 | 39 |
| Vitis shuttleworthii (calloose grape) | B-type ARR (EST) | vshu2736 | 40 |
| Allium cepa (onion) | B-type ARR (EST) | acep18399 | 41 |
| Phaseolus vulgaris (common bean) | B-type ARR (EST) | pvul1438 | 42 |
| Citrus clementina | B-type ARR (EST) | ccle4118 | 43 |
| Solanum tuberosum (potato) | B-type ARR (EST) | stub37069 | 44 |
| Sorghum bicolor | B-type ARR (EST) | sorg41303 | 45 |
| Medicago truncatula (barrel medic) | B-type ARR (EST) | mtru90179 | 46 |
| Pinus taeda (loblolly pine) | B-type ARR (EST) | ptae45447 | 47 |
| Pinus taeda (loblolly pine) | B-type ARR (EST) | ptae43050 | 48 |
| Pinus taeda (loblolly pine) | B-type ARR (EST) | ptae63373 | 49 |
| Populus deltoides | B-type ARR (EST) | pdel1045 | 50 |
| Arabidopsis thaliana | APRR2 | At 4g18020 | 63 |
| Arabidopsis thaliana | APRR4 | At 5g49240 | 64 |
| Arabidopsis thaliana | CCA1 | At 2g46830 | 65 | has "EAR motif repressor activity" within the meaning of the present invention, if the EAR motif exhibits a reduction of the expression of the reporter gene in a reporter gene assay by at least 10%, at least 20%, at least 30%, at least 40%, at least 50%, at least 60%, at least 70%, at least 80%, at least 90, at least 95%, at least 98% or at least 99%. In especially preferred embodiments the EAR motif comprises the sequence LDLD-LELRLGFA (SEQ ID NO: 52) or a variant thereof having EAR motif repressor activity. The sequence according to SEQ ID NO: 52 is also known under the name SRDX motif (Hiratsuka et al. (2003) Plant J. 34 (5), pp. 733-739).

In preferred embodiments the PAH3/HID is derived from a protein selected from the group consisting of Sin3A, SAP30L, and SAP18.

In preferred embodiments of the fusion protein of the invention the DNA binding factor and the repressor domain are coupled directly to each other or via a linker. The linker preferably comprises a polypeptide consisting of 1 to 100 amino acids, preferably 1 to 60 amino acids, more preferably 1 to 50 amino acids, more preferably 1 to 40 amino acids, and even more preferably said polypeptide consists of 1, 2, 3, 4, 5, 6, 7, 8, 9, 10, 15, 20, 25, 30, 35, or 40 amino acids. It is especially preferred that the linker comprises one or more glycine residues. In preferred embodiments the DNA binding factor is coupled to the N-terminal end of the linker and the transcriptional repressor domain is coupled to the C-terminal end of the linker. Embodiments, wherein the transcriptional repressor domain is coupled to the N-terminal end of the linker and the DNA binding factor is coupled to the C-terminal end of the linker are also considered within the present invention.

In preferred embodiments the fusion further comprises a nuclear localization signal. In especially preferred embodiments the nuclear localisation signal is selected from the group consisting of PKKKRKV (SEQ ID NO: 53), KIPIK (SEQ ID NO: 54), SPPKAVKRPAATKKAGQAKKKKLD-KEDES (SEQ ID NO: 55), MEEAVTMAPAAVSSAV-VGDPMEYNAILRRKLEEDLE (SEQ ID NO: 56), KKRARL VRNRESAQLS RQRKK (SEQ ID NO: 57) and homologs and variants of any of these nuclear localisation signals.

The present invention further provides a polynucleotide comprising a nucleic acid sequence encoding the fusion protein of the invention as defined supra or infra or as set forth in preferred embodiments of the invention. The present invention further provides a vector comprising said polynucleotide. In preferred embodiments said vector is constructed in such a manner that the polynucleotide is operatively linked to expression control sequences allowing expression of the nucleic acid sequence encoding the fusion protein in prokaryotic and/or eukaryotic host cells. The invention further provides a cell comprising said polynucleotide or said vector as defined supra or infra or as set forth in preferred embodiments of the invention.

The present invention further provides a transgenic plant comprising said polynucleotide, said vector or said cell as defined supra or infra or as set forth in preferred embodiments of the invention. The present invention further provides parts, cells, or seeds of said transgenic plant. The present invention also provides plants or propagating material thereof regenerated from a transgenic plant as defined supra or infra or as set forth in preferred embodiments.

The present invention is further directed at a process for making a transgenic plant, parts, cells, or seeds thereof or propagating material as defined supra or infra or as set forth in preferred embodiments comprising the step of transforming a cell or cells of a plant with a vector of the invention as set forth supra or infra. In preferred embodiments, the process comprises the further step of selecting transformed cells and regenerating of transformed plants from the cells. The cell that can be used include any cell that is known in the art to be transfectable with a vector including without limitation tissue culture cells and developing floral tissues as in the floral-dip method (Clough S. J. and Bent A F (1998) Plant J. 16:735-43).

The present invention further relates to the use of a transgenic plant, parts, cells, or seeds thereof or propagating material as defined supra or infra or as set forth in preferred embodiments for producing seeds of enhanced size, with enhanced seed filling, with reduced seed loss and/or with more rapid germination, wherein the transgenic plants are cultured under culturing conditions and the preferably mature seeds are harvested.

The present invention also relates to the use of a transgenic plant, parts, cells, or seeds thereof or propagating material as defined supra or infra or as set forth in preferred embodiments for producing a live root system with increased root mass, root length and/or root branching, wherein the transgenic plant is cultured under culturing conditions. In a preferred embodiment this live root system with increased root mass, root length and/or root branching is useful for bioremediation and/or lodging resistance and/or altered mineral composition of the shoot and/or the harvested product and/or the root products. In another preferred embodiment this live root system is a rootstock used in a grafting procedure with a scion for improving the root-related characteristics of the resulting plant or tree (or similar).

The present invention further relates to a use of a transgenic plant of the invention for producing wood with modified characteristics, wherein the activity of the cambial tissue is modified, and wherein the transgenic plant is cultured under culturing conditions. The present invention further relates to a use of a transgenic plant of the invention for producing a shoot with altered shoot architecture (i.e. with modified branching pattern), wherein the apical dominance in plants is altered, and wherein the transgenic plant is cultured under culturing conditions. The present invention also relates to a use of a transgenic plant of the invention for producing leaves with altered leaf senescence, wherein the transgenic plant is cultured under culturing conditions. The present invention also relates to a use of a transgenic plant of the invention for producing flowers with altered timing of reproduction, e.g. with earlier flower induction, wherein the transgenic plant is cultured under culturing conditions. It is contemplated within the present invention that the direction of any of the above-mentioned changes, such as altered leaf senescence, altered timing of reproduction, etc., may differ between different plant species. It is shown in Example 3.4 below that the 35S:ARR1_SRDX transgenic *Arabidopsis thaliana* plants exhibit an earlier flowering. However, transgenic plants of other species expressing the fusion protein of the invention could exhibit a later flowering.

The present invention is further directed at the use of a transgenically expressed fusion protein of the invention as defined supra or infra or as set forth in preferred embodiments for enhancing the seed size, the seed filling, the root mass, the root length and/or the root branching and/or for reducing seed loss and/or germination time of a plant.

The present invention is also directed at the use of a transgenically expressed fusion protein of the invention as defined supra or infra or as set forth in preferred embodiments for modifying the characteristics of wood, for altering shoot architecture (i.e. modifying the branching pattern of the shoot), for altering leaf senescence and other senescence processes and/or for altering the timing of reproduction, e.g. causing earlier or later flower induction.

In preferred embodiments of any of the above uses of the present invention the fusion protein is tissue-specifically expressed. In more preferred embodiments, the fusion protein is specifically expressed in tissue selected from the group consisting of root tissue, embryo tissue, endosperm tissue, and aleurone tissue.

The present invention further provides a method for enhancing the seed size, the seed filling, the root mass, the root length and/or the root branching and/or for reducing seed loss and/or germination time of a plant, comprising the steps of
- introducing by genetic engineering into the plant a nucleic acid; and
- expressing said nucleic acid, wherein the nucleic acid is the polynucleotide or the vector of the invention as defined supra or infra or as set forth in preferred embodiments.

In preferred embodiments of this method the expression of the polynucleotide is controlled by a tissue-specific regulatory element. In more preferred embodiments the tissue for which the regulatory element is specific is selected from the group consisting of root tissue, embryo tissue, endosperm tissue, and aleurone tissue. In even more preferred embodiments the tissue-specific regulatory element is a promoter selected from the group consisting of the promoters disclosed in table 1.

Furthermore, the present invention provides a method for making seeds of enhanced size, with enhanced seed filling, reduced seed loss and/or more rapid germination, wherein the transgenic plant, parts, cells, seeds or propagating material thereof as defined supra or infra or as set forth in preferred embodiments are cultured under culturing conditions and preferably mature seeds being produced thereby are harvested.

The present invention further provides seeds obtainable by any of the methods described supra or infra.

The present invention also provides a method for making plants with increased root mass, root length and/or root branching and/or for reducing seed loss and/or germination time of a plant, wherein the transgenic plant, parts, cells, seeds or propagating material thereof as defined supra or infra or as set forth in preferred embodiments are cultured under culturing conditions.

It is also contemplated within the present invention that the fusion proteins or the transgenic plants as defined supra or infra or as set forth in preferred embodiments can be used to enhance the resistance to pathogens which induce cell division in plants. Such pathogens include inter alia *Agrobacterium*, certain nematodes, and *Plasmodiophora brassicae* in the case of *Brassica* species (see e.g. Siemens et al., Mol. Plant. Mic. Interact. 19, 480-494, 2006). Accordingly, the present invention also provide a method for enhancing the resistance to pathogens which induce cell division in plants, the methods comprising the steps of introducing by genetic engineering into the plant a nucleic acid; and expressing said nucleic acid; wherein the nucleic acid is the polynucleotide or the vector of the invention as defined supra or infra or as set forth in preferred embodiments. It is especially preferred that the polynucleotide is controlled by a pathogen-specific regulatory element, preferably by a pathogen-inducible promoter as shown in Table 1.

In preferred embodiments of the transgenic plants, methods and uses of the present invention, variants of the DNA binding factor and/or the repressor domain of the invention may comprise one or more further modifications selected from the group consisting of amino acid exchanges, amino acid insertions, and amino acid deletions. The deletions can be internal deletions, N-terminal truncations and/or C-terminal truncations. A protein variant differing from the protein from which it is derived by deletions only may be termed a protein "fragment". In preferred embodiments the DNA binding factor variant and/or the repressor domain variant preferably comprise independently from each other from 1 to 100, from 1 to 80, from 1 to 60, from 1 to 50, from 1 to 40, from 1 to 30, from 1 to 20, from 1 to 15, from 1 to 12, or from 1 to 10 modifications. These modifications can be any combination of amino acid exchanges, amino acid insertions, and amino acid deletions (i.e. internal deletions, N-terminal truncations and C-terminal truncations). The term "modification" in this context is to be understood as any change to an amino acid as compared to the corresponding protein sequence. For example, if a protein is modified by the insertion of 5 amino acids, the deletion of 6 amino acids, the exchange of 7 amino acids, an N-terminal truncation, wherein 8 N-terminal amino acids are deleted, and a C-terminal truncation, wherein 9 C-terminal amino acids are deleted, the total number of modifications amounts to 35 (5+6+7+8+9=35). In preferred embodiments thereof the DNA binding factor variant and/or the repressor domain variant comprise independently from each other from 1 to 50, from 1 to 40, from 1 to 30, from 1 to 20, from 1 to 15, from 1 to 12, or from 1 to 10 amino acid insertions. In further preferred embodiments thereof the DNA binding factor variant and/or the repressor domain variant comprise independently from each other from 1 to 50, from 1 to 40, from 1 to 30, from 1 to 20, from 1 to 15, from 1 to 12, or from 1 to 10 amino acid deletions. In other preferred embodiments thereof the DNA binding factor variant and/or the repressor domain variant comprise independently from each other from 1 to 50, from 1 to 40, from 1 to 30, from 1 to 20, from 1 to 15, from 1 to 12, or from 1 to 10 amino acid substitutions. It is preferred that the further modification leads to a molecule that is at least 50% identical to the DNA binding factor or the repressor domain, respectively, from which it is derived, preferably at least 60%, at least 70%, at least 80%, at least 85%, at least 90% or at least 95% identical to the DNA binding factor or the repressor domain, respectively.

The invention allows obtaining favorable phenotype features, but avoiding unfavorable phenotype features. For example, enhanced root branching may be obtained without dwarf growth of other plant parts. The same applies in an analogous manner to the seed size, the seed filling or the germination time. As a result, yield parameters, like the harvest index are considerably improved.

The target tissue is preferably selected from the group consisting of "root tissue, embryo tissue, endosperm tissue, and aleurone tissue". If the target tissue is root tissue and other tissue is not target tissue, a plant is obtained, which shows enhanced root branching but unaltered shoot growth. If the target tissue is embryo tissue, endosperm tissue or aleurone tissue, but other tissue is not target tissue, larger seeds are obtained at unaltered other properties of the plant. It is, however, also possible to combine both said subgroups of target tissue, provided that other tissue is not target tissue. This will result in a plant, wherein both, root branching and seed size are enhanced. This is most favorable since the increase in yield parameters is enhanced further.

It is possible to genetically modify specifically the target tissue in such a manner that fusion proteins are expressed tissue-specifically. Tissue specific expression of fusion proteins may be achieved in that the expression of the compound is controlled by a regulatory element, which is tissue specific, i.e. promotes expression only in the target tissue and not in tissue not being target tissue.

The transgenic plant of the invention is naturally not capable of reducing cytokinin signaling activity tissue-specifically. A foreign DNA sequence is introduced by genetic engineering, which encodes for at least one nucleic acid or at least one protein or peptide, wherein the foreign DNA sequence stands under the control of a tissue-specific regulatory element.

The transgenic plant of the invention produces seeds of enhanced size, enhanced seed filling, reduced seed loss, reduced germination time and/or produces roots with enhanced branching, length and/or mass.

The invention further comprises a method for enhancing the seed size, the seed filling, the root mass, the root length and/or the root branching and/or for reducing seed loss and/or germination time of a plant, wherein the cytokinin signaling activity is essentially unaltered in tissue not being target tissue. The target tissue is preferably selected from the group consisting of "root tissue, embryo tissue, endosperm tissue, and aleurone tissue". The tissue-specific regulatory element may be a promoter selected from the group consisting of the elements of the table 1 or any other promoter of the said specificity. Further details about applicable promoters and how to identify such promoters are obtainable from Zimmermann et al., (2004) Plant Physiol. 136, 2621-2632. Based on these data the expert skilled in the art can identify promoters with the needed specificity of expression.

Plants with an enhanced root system are better adapted to stress, they enhance plant vigour, they grow better on soil poor in nutritional elements (minerals), they show improved growth with limited water resources and enhanced resistance to drought finally leading to improved yield parameters, in particular an improved harvest index. They can also be used for phytoremediation, i.e. plant mediated removal of toxic substances from soil, and/or prevention and/or arrest of soil erosion. The methods of the invention as well as the plants thereof typically result in enhanced growth of the primary root and/or strongly enhanced root branching.

Improvement of the root system in particular is favourable for staple crops, like sugar beet, manioc, yams, sweet potato, vegetables with consumable root parts like carrots and radish, and medicinal plants with usable root parts, like ginseng. But also the yield parameters of other crops like wheat, maize etc. are increased, since the plant growth is improved due to the comparatively better uptake of water and nutritional substances from the soil.

Plants with an increased seed size provide higher yield parameters for obvious reasons.

Without wishing to be bound by any particular theory, the inventors believe that the above depicted advantageous properties of the transgenic plants of the invention are mainly achieved by means of a reduction in cytokinin signaling. However, it is also contemplated that the fusion proteins of the present invention act as transcriptional repressors in other pathways than the cytokinin signaling pathway, e.g. they may also interfere with ethylene signaling and/or red-light signaling pathways.

The present invention is applicable to any plant, in particular to monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Avena sativa*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeda japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalla villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Muse sapientum*, *Nicotiana* spp., *Onobrychis* spp., *Ornithopus* spp., *Oryza* spp., *Panicum virgatum*, *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria flecltii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Siiburus alopecuroides*, *Stylosanthos humilis*, *Tadehagi* spp, *Taxodium distichum*, *Themeda triandra*, *Trifolium* spp., *Triticum* spp., *Tsuga heterophylia*, *Vaccinium* spp., *Vicia* spp., *Vitis vinifera*, *Watsonia pyramidata*, *Zantedeschia aethiopica*, *Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugar beet, sugar cane, sunflower, switchgrass, tomato, squash, and tea, amongst others.

Means for introducing foreign resp. recombinant DNA into plant tissue or cells include, but are not limited to, transformation using $CaCl_2$ and variations thereof, in particular the method described by Hanahan (Hanahan, D. (1983) J. Mol. Biol. 166, 557-580), direct DNA uptake into protoplasts (Krens, F. A. et al (1982) Nature 296, 72-74); Paszkowski J. et al. (1984) EMBO J. 3, 2717-2722), PEG-mediated uptake to protoplasts (Armstrong C. L. et al. (1990) Plant Cell Reports 9, 335-339) microparticle bombardment, electroporation (Fromm et al., 1985), microinjection of DNA (Crossway A. et al. (1986) Mol. Gen. Genet. 2002, 179-185), microparticle bombardment of tissue explants or cells (Christou et al. (1988) Plant Physiol. 87, 671-674; Sanford, 1988), vacuum-infiltration of tissue with nucleic acid, or in the case of plants, T-DNA-mediated transfer from *Agrobacterium* to the plant tissue as described essentially by An et al. (1985), Dodds et al., (1985), An G. et al. (1985) EMBO J. 4, 277-284; Dodds, J. H. "Plant genetic engineering" Cambridge University Press; Herrera-Estrella L. et al. (1983) EMBO J. 2, 987-995. Methods for transformation of monocotyledonous plants are well known in the art and include *Agrobacterium*-mediated transformation (WO 97/48814; WO 98/54961; WO 94/00977; WO 98/17813; WO 99/04618; WO 95/06722), microprojectile bombardment (U.S. Pat. Nos. 5,969,213; 5,736,369; WO 94/13822; U.S. Pat. Nos. 5,874,265/5,990,390; 5,405,765; 5,955,362), DNA uptake (WO 93/18168), microinjection of *Agrobacterium* cells (DE 43 092 03) and sonication (U.S. Pat. No. 5,693,512). For microparticle bombardment of cells, a microparticle is propelled into a cell to produce a transformed cell. Any suitable ballistic cell transformation methodology and apparatus can be used in performing the present invention. Exemplary apparatus and procedures are disclosed in U.S. Pat. Nos. 5,122,466 and 4,945,050. When using ballistic transformation procedures, the gene construct may incorporate a plasmid capable of replicating in the cell to be transformed. Examples of microparticles suitable for use in such systems include 1 to 5 µm gold spheres. The DNA construct may be deposited on the microparticle by any suitable technique, such as by precipitation. A whole plant may be regenerated from the transformed or transformed cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

Preferably, the plant produced according to the inventive method is transfected or transformed with a genetic sequence, or amenable to the introduction of a fusion protein by any art-recognized means, such as microprojectile bombardment, microinjection, *Agrobacterium*-mediated transformation (including in planta transformation), protoplast fusion, or electroporation, amongst others. Most preferably said plant is produced by *Agrobacterium*-mediated transformation. *Agrobacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

(b) A phylogenetic tree of the DNA-binding domains of the B-type response regulators. The tree was constructed using Neighbour joining algorithm. Phylogenetic and molecular evolutionary analyses were conducted using the MEGA 3.1 program (Kumar et al., 2004).

Figure 2:
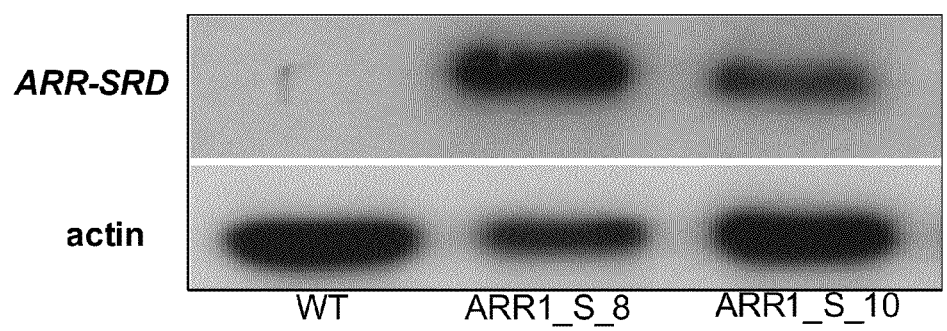

FIG. 2. Expression of the 35S::ARR1-SRDX gene fusion.
Total RNA samples were isolated from 35 days old plants and the transcript was analysed by Northern blot hybridization using a probe specific for the ARR1-SRDX gene fusion. The actin transcript was used as loading control. WT, wild type Col-0; ARR1_S_8 and ARR1_S_10 are different, independent lines of 35S::ARR1—SRDX transgenic plants.

Figure 3:
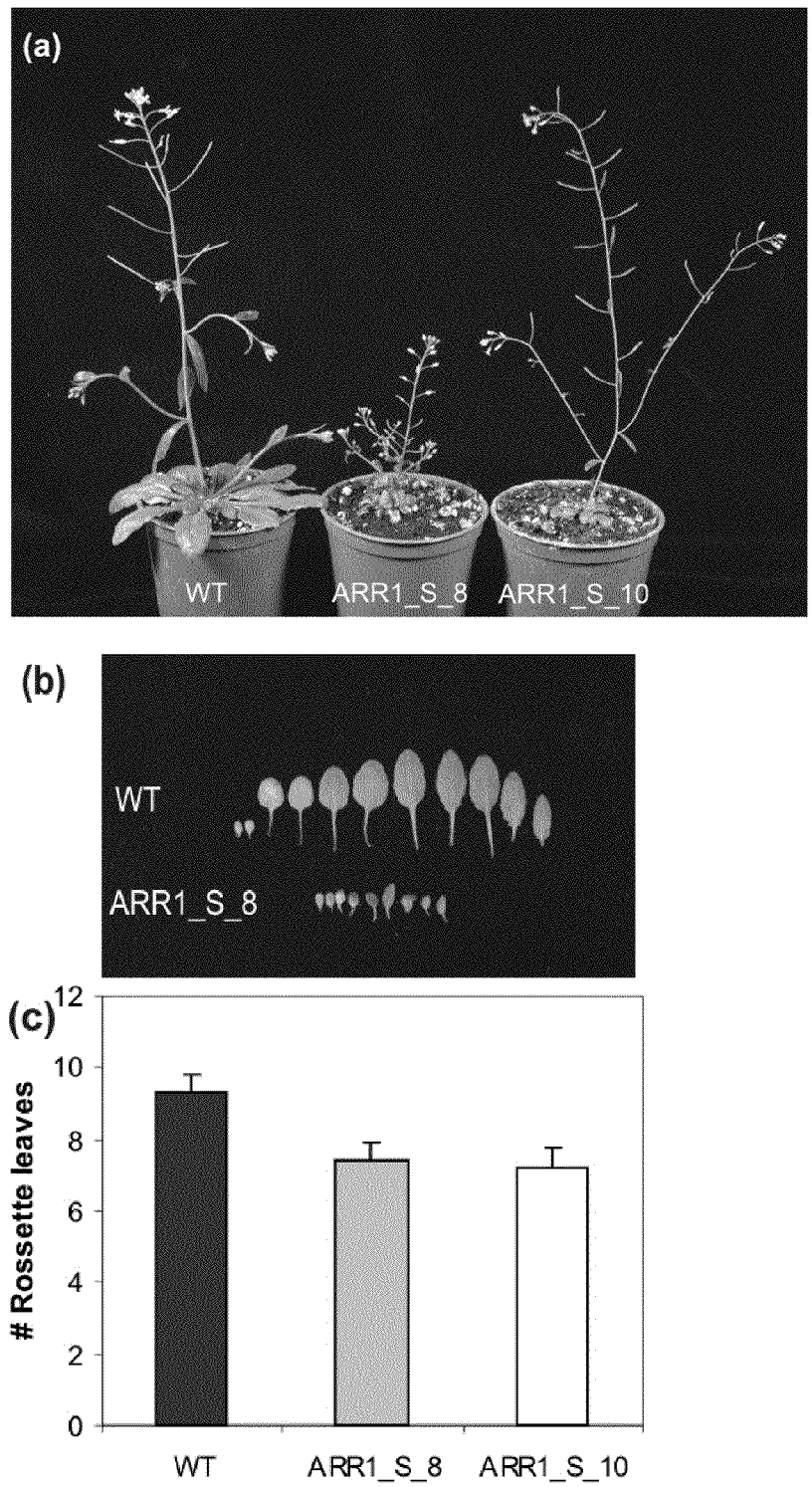

FIG. 3. Shoot phenotype of 35S::ARR1-SRDX transgenic plants.

(a) Shoot phenotype of transgenic 35S::ARR1-SRDX plants, 35 DAG (days after germination) compared to WT.

(b) Leaf phenotype of an ARR1_S_8 and of a WT plant 20 DAG.

(c) 35S::ARR1—SRDX transgenic plants have formed less leaves than WT at the onset of flowering. The total number of rosette leaves were counted 19 DAG. Error bars represents SD (n>20).

Figure 4:
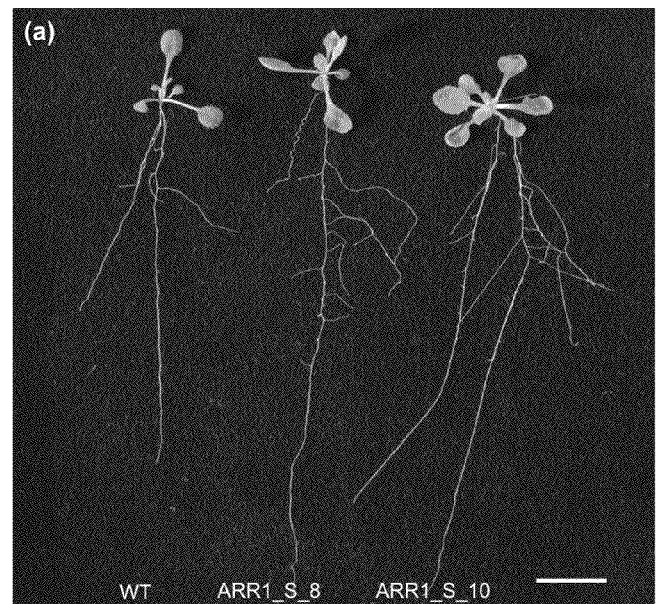
Figure 4:
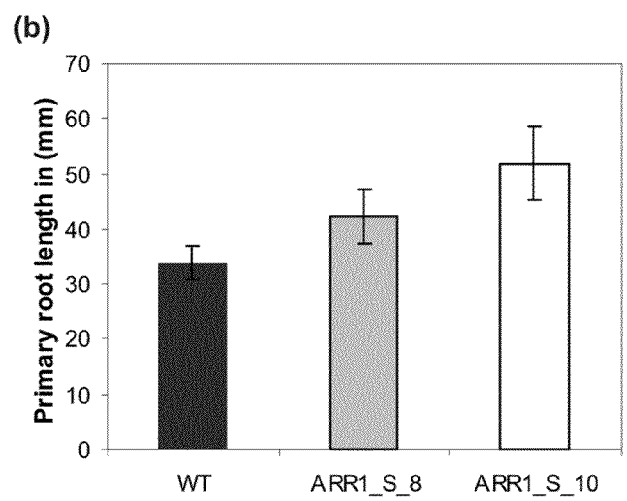
Figure 4:
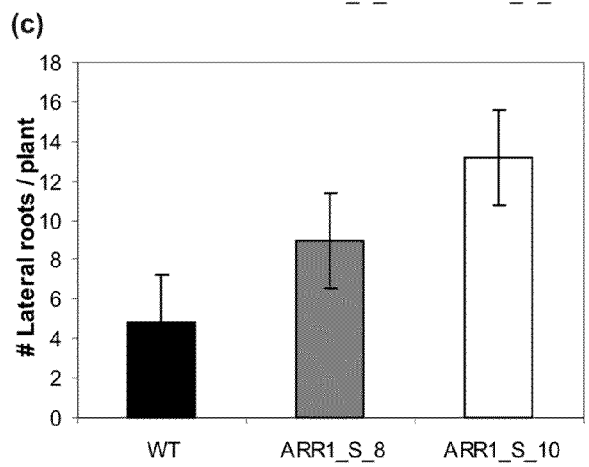

FIG. 4. Root phenotype of 35S::ARR1-SRDX transgenic plants.

(a) Transgenic plants show longer and more branched roots than WT plants. Seedlings were grown vertically on MS plates. The pictures were taken 10 DAG. Bar size is 1 cm.

(b) 35S::ARR1-SRDX plants produce larger primary root than WT. The primary root length of each line is measured 10 DAG.

(c) 35S::ARR1-SRDX plants produce a greater number of lateral roots compared to WT. The number of lateral roots was determined 10 DAG.

Results shown in (b-c) for each line represent means from at least three independent replicates. Error bars represent SD (n>15).

Figure 5:
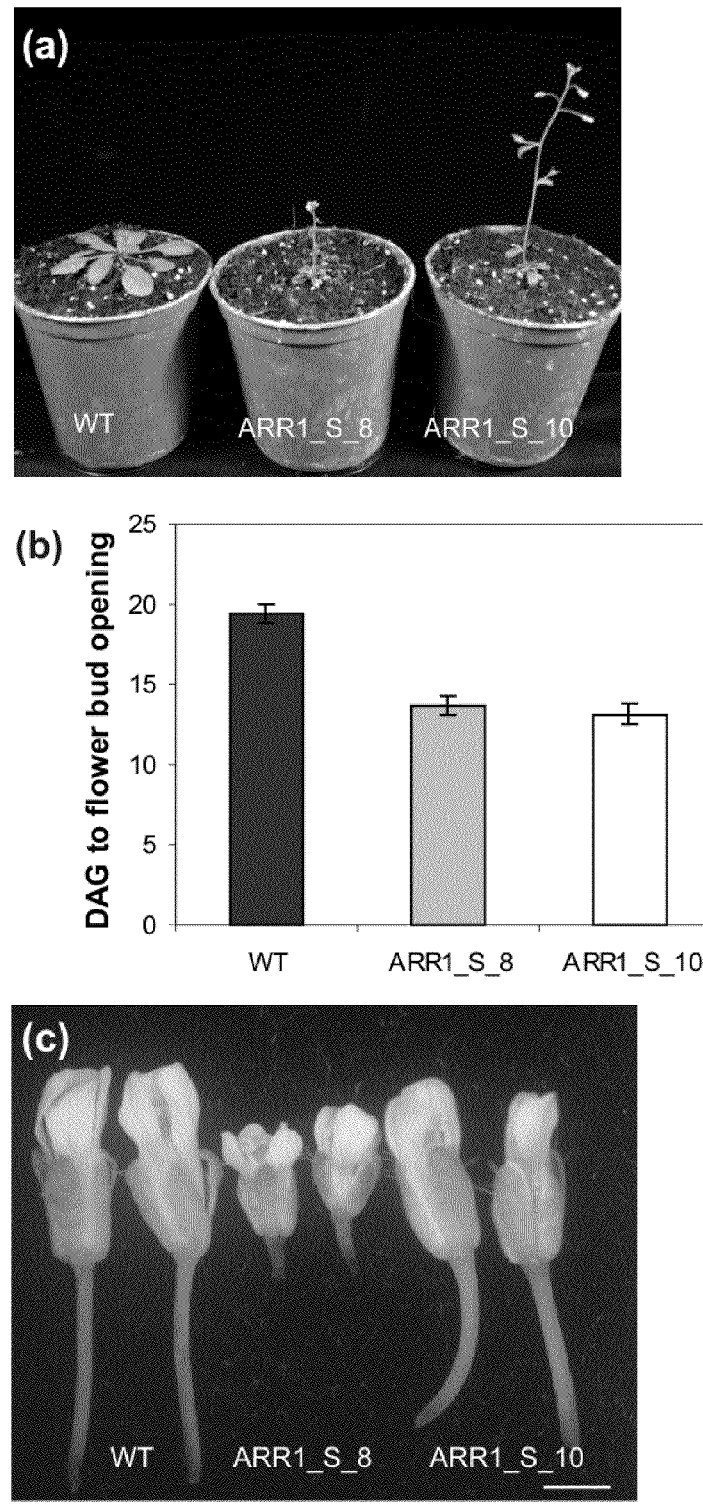
Figure 5:
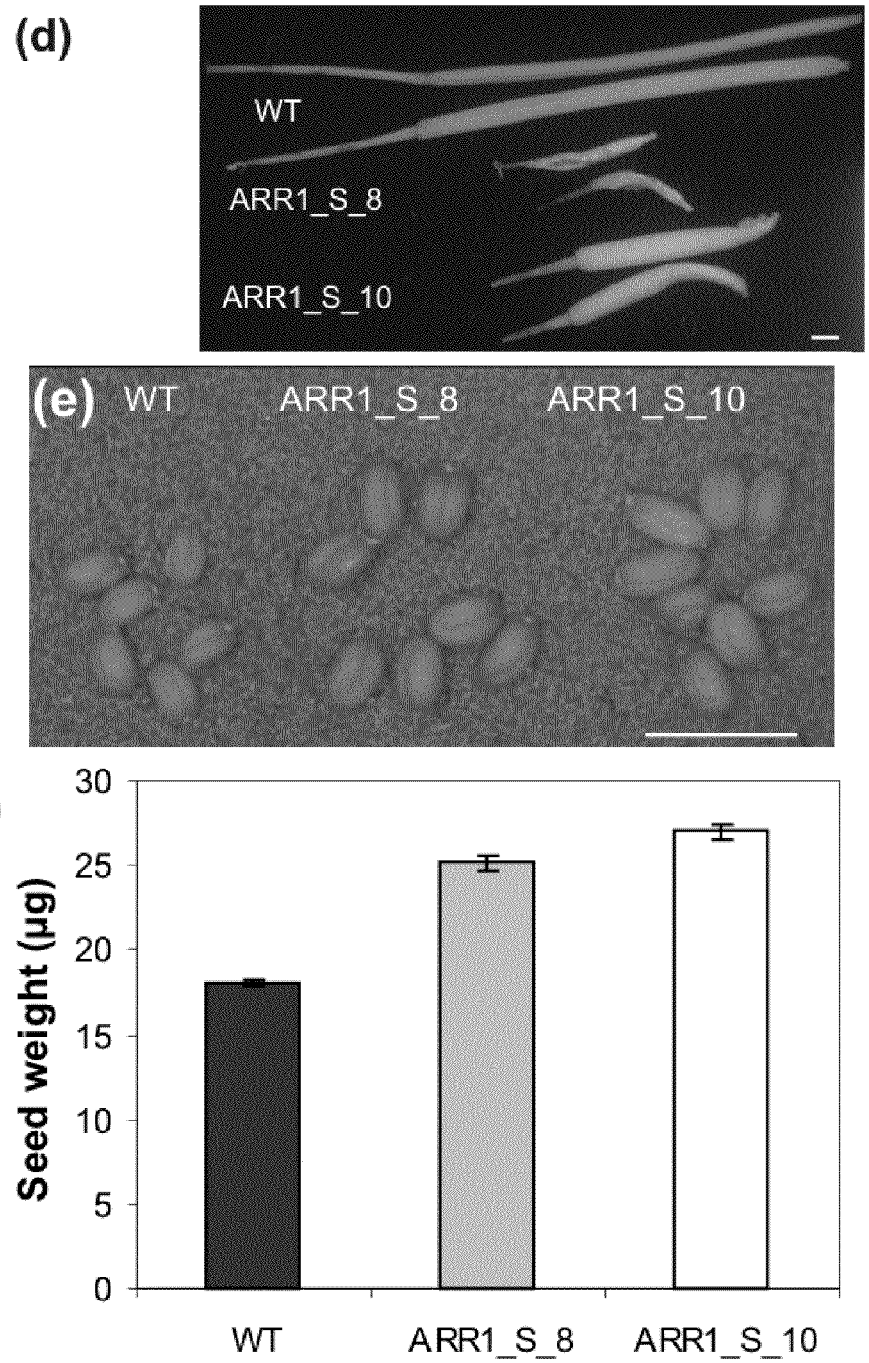

FIG. 5. Reproductive organs phenotype of 35S::ARR1-SRDX transgenic plants.

(a) Flower induction occurs earlier in 35S::ARR1-SRDX transgenic plants compared to WT plants. The plants were grown in day/night conditions at 22° C. and photographed 19 DAG.

(b) Quantitative analysis of the early flowering phenotype of 35S::ARR1-SRDX transgenic plants. The graph shows the time span required for flower bud opening (DAG) in transgenic plants compared to WT.

(c) Flower morphology of two independent lines of 35S::ARR1-SRDX plants compared to WT.

(d) Siliques of transgenic plants compared to WT.

(e) Seeds of transgenic lines compared to WT.

(f) The seeds of transgenic plants show an increased weight. Seed biomass was determined by weighting ten pools of 200 seeds for each line. Bar size in c-e is 1.0 mm.

Figure 6:
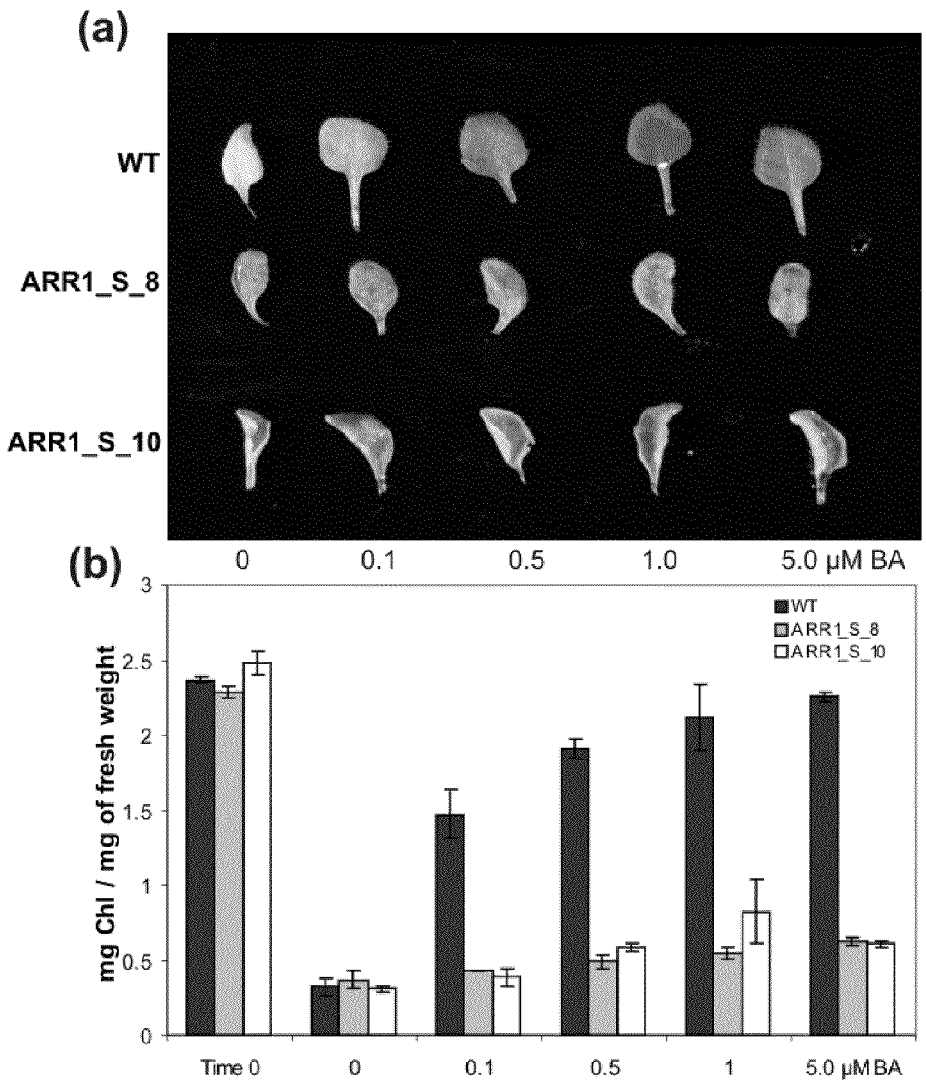

FIG. 6. 35S::ARR1-SRDX plants are less sensitive to cytokinin in a chlorophyll retention assay.

(a) Leaf phenotype of transgenic and WT plants during cytokinin dependent chlorophyll retention. Fully expanded leaves were excised from 24d old plants and floated on water supplemented with various concentrations of cytokinin for 10d in dark.

(b) Quantification of chlorophyll retention by cytokinin. The graph shows the amount of chlorophyll per mg fresh weight of WT and transgenic plants following treatment various concentrations of BA. Three independent plates with five leaves per plate were examined for each concentration. Two chlorophyll measurements were taken per plate. The chlorophyll content was determined spectrophotometrically as described in Example 3.5. Error bars represent SD (n=15).

Figure 7:
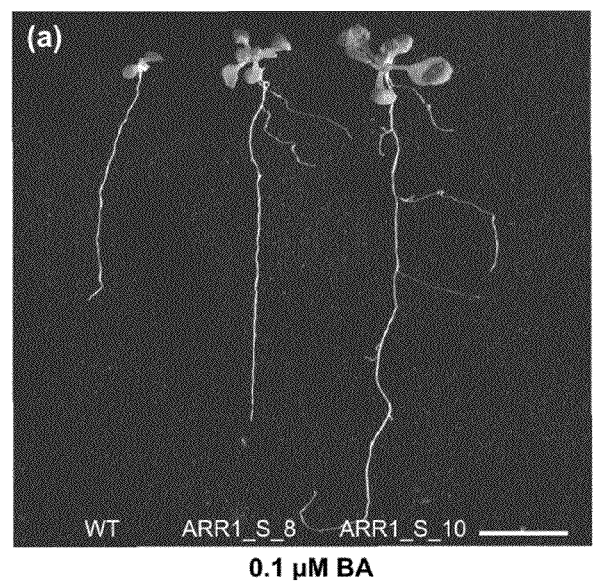
Figure 7:
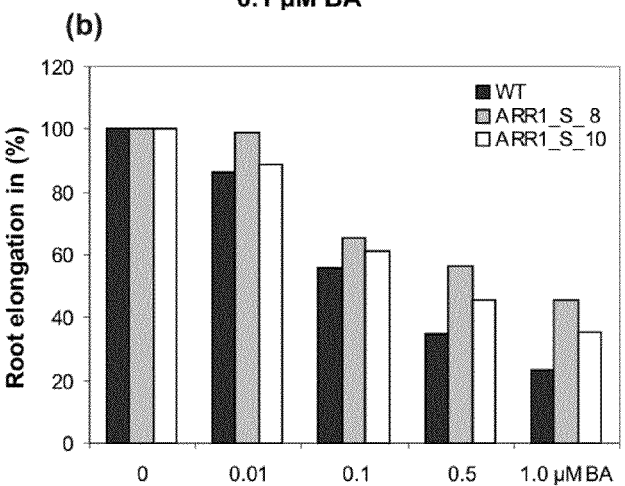
Figure 7:
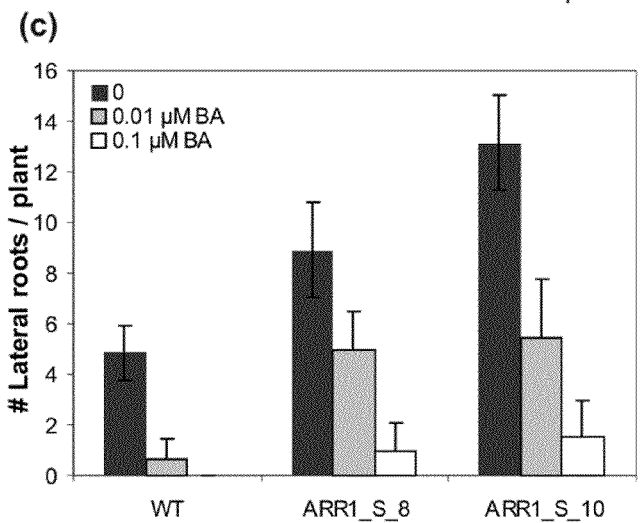

FIG. 7. Cytokinin sensitivity in roots of 35S::ARR1—SRDX transgenic plants.

(a) Transgenic plants show longer and more branched roots than control plants. Seedlings were grown vertically on plates supplemented with different concentrations of BA ranging from 0.01 μM to 1.0 μM. The pictures were taken 10 DAG on 0.1 μM BA. Bar size is 1 cm.

(b) 35S::ARR1-SRDX plants are less sensitive to cytokinin inhibition of root elongation. Root elongation was measured for each line between 4 and 9 DAG. The root elongation of each line is expressed as percentage of its DMSO control. Results shown for each line represent means from at least three independent replicates.

(c) 35S::ARR1-SRDX plants are less sensitive to cytokinin inhibition of lateral root formation. The number of lateral roots was determined 9 DAG. Error bars represent SD (n>15).

Figure 8:
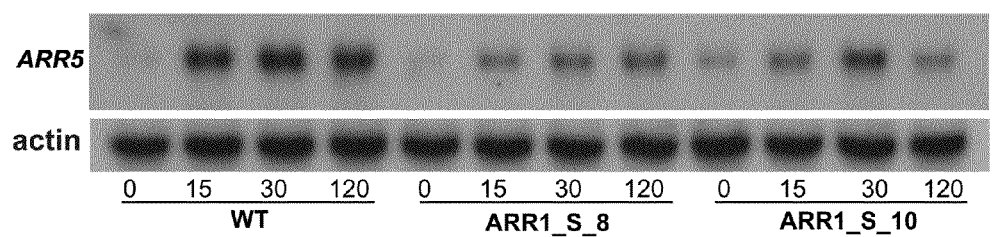

FIG. 8. 35S::ARR1-SRDX gene expression dampens the primary cytokinin response.

Total RNA was isolated from 5-days-old wild type and 35S::ARR1-SRDX seedlings treated with 5 μM BA for 0 min, 15 min, 30 min and 120 min. Northern blots were hybridized with a probe specific for the cytokinin response gene ARR5. Hybridisation with an actin probe was used as loading control.

Figure 9:
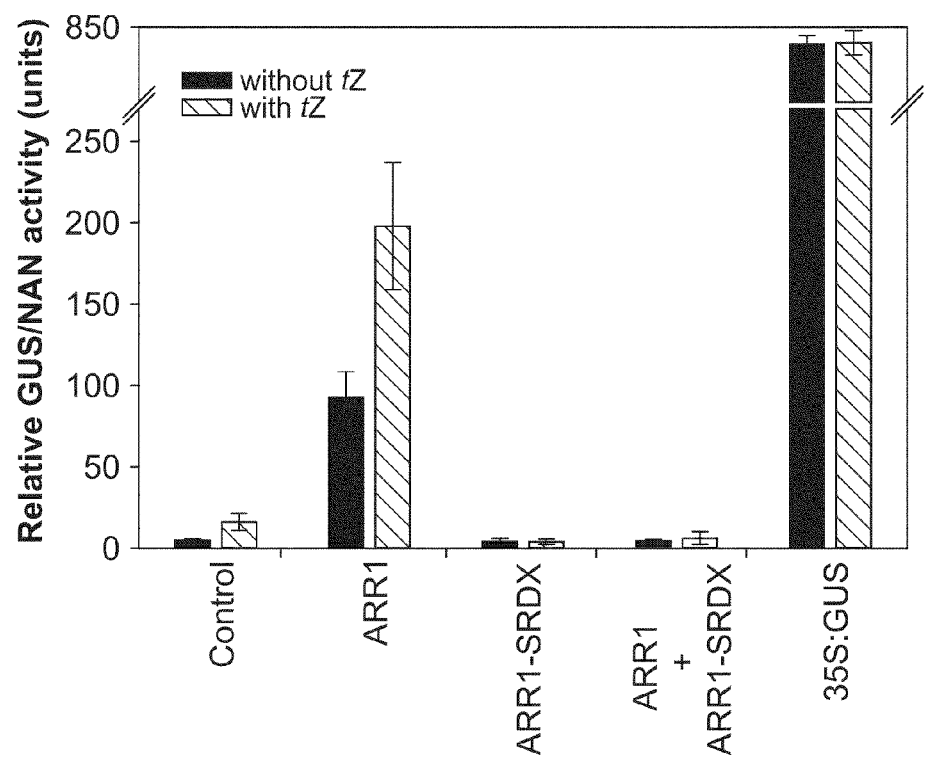

FIG. 9. 35S::ARR1-SRDX Represses the Transactivation Capacity of ARR1 in a Protoplast Transactivation Assay.

The activation of the ARR6:GUS reporter gene was measured without and 16 h after the addition of 500 nM trans-zeatin (tZ). The ARR6:GUS reporter construct and a 35S: GUS construct without any effector plasmid were used as controls. Protoplasts were co-transfected with the ARR6: GUS reporter and an effector plasmid expressing ARR1, ARR1-SRDX or both effector plasmids simultaneously. The fusion of the SRDX domain to ARR1 effectively repressed the transactivation capacity of ARR1. Variations in transformation efficiencies were normalized by using a 35S:NAN reporter gene construct. The mean values and SD of four independent transfection assays were calculated and shown as relative GUS/NAN activity units.

Figure 10:
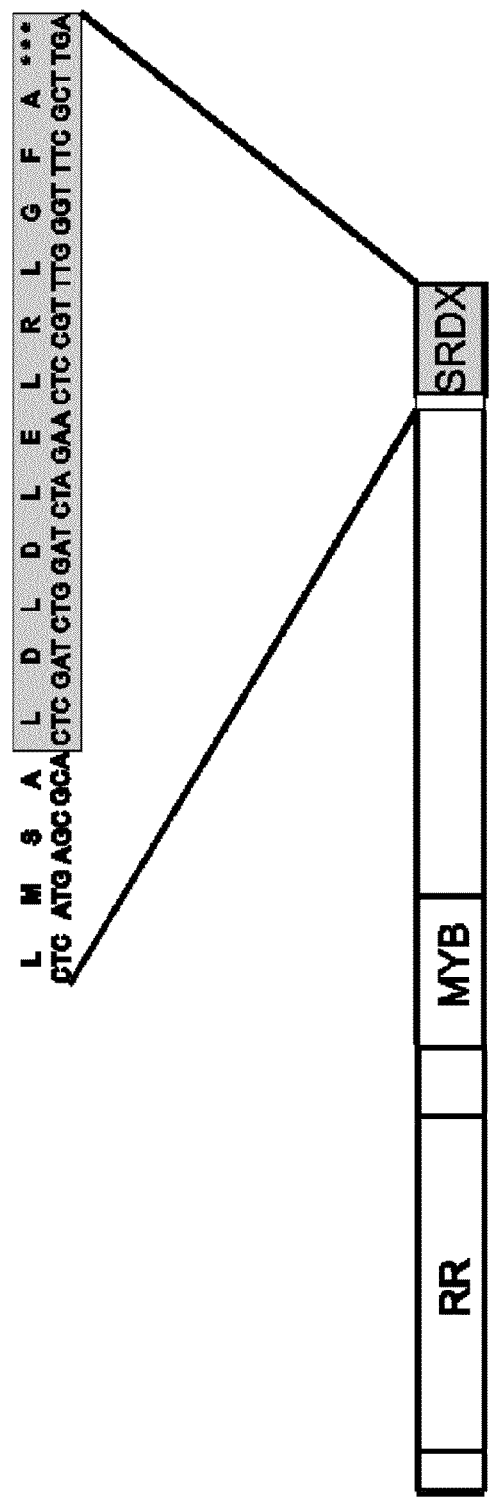

FIG. 10. Schematic Representation of the ARR1-SRDX Fusion Protein.

This figure shows a scheme of the ARR1-SRDX fusion protein with the junction between ARR1 and the SRDX peptide highlighted in the excerpt. The size of the domains is not drawn to scale. RR, response regulator domain; MYB, DNA-binding domain; SRDX, SRDX domain. The indicated amino acid sequence and nucleotide sequence are listed in the sequence listing as SEQ ID NO: 66 and SEQ ID NO: 67, respectively.

EXAMPLES

In the following the invention is explained in more detail by non-limiting examples:

Example 1

Sequence Analysis of the DNA-binding domains of B-type ARRs

Figure 1:
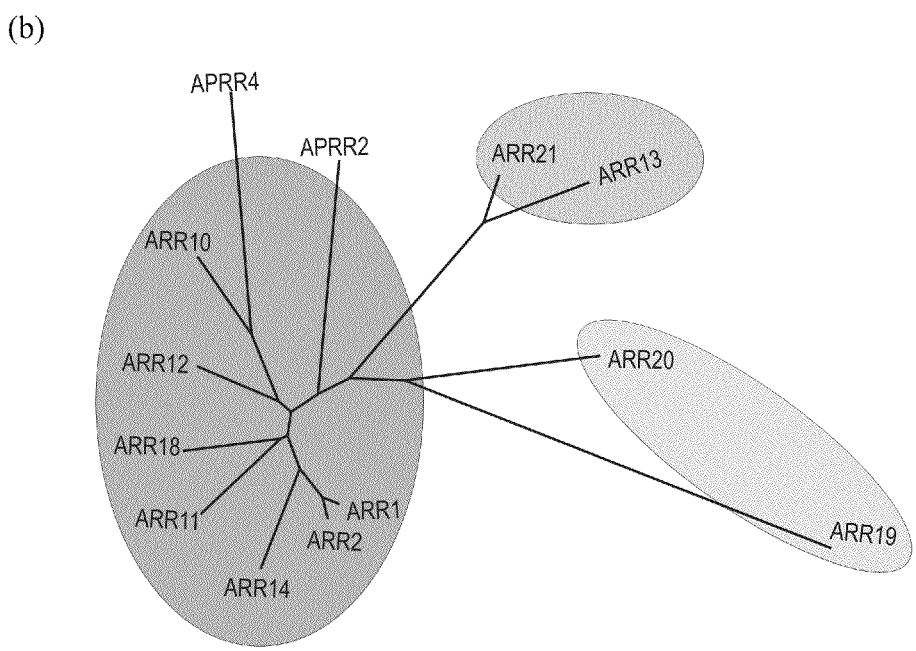
FIG. 1. Sequence comparison and phylogenetic analysis of DNA binding domains of B-type ARRs (a) Multiple sequence alignment of the DNA binding domains of B-type response regulator. Full-length protein sequences of the response regulators were obtained from Entrez Protein Database (National Centre for Biotechnology Information [NCBI]) and their DNA binding domains sequences were identified by searching Protein family database (Pfam)(Finn et al., 2006). Binding domain sequences were aligned using the ClustalW program. The conserved amino acids are highlighted using the Boxshade 3.21 program. The ★ indicates the amino acids which are in direct contact with DNA (Hosada et al., 2002)

The CRES-T is based on the dominant repression of target gene expression. To be effective as repressors of a whole protein family, the DNA-binding domains and thus the promoter target sequences of those transcription factors should be similar. Therefore we analyzed first the similarity of the DNA-binding domains of B-type ARRs and of pseudo response regulators APRR2 and APRR4, which contain a MYB DNA-binding domain (Makino et al., 2000). The respective domains were identified using the Pfam programme (Finn et al., 2006) and subsequently the sequences were aligned using the Clustal W algorithm (Thompson et al., 1994) (SEQ ID NO: 1 to SEQ ID NO: 11, SEQ ID NO: 60 to SEQ ID NO: 61; FIG. 1a). The DNA-binding domain of another MYB-protein, CCA1, which has a complementary target sequence to the B-type ARR1 (Wang et al., 1997), was also added to the alignment (SEQ ID NO: 62).

The DNA binding domain of ARR1 (SEQ ID NO: 1) shares the highest homology with ARR2 (SEQ ID NO: 2) and the lowest with ARR19 (SEQ ID NO: 9) (96% and 47% identity, respectively). The high degree of conservation of amino acids important for DNA recognition (FIG. 1a) and the fact that several B-type ARRs have been shown to bind to the same or very similar sequence motifs (Sakai et al. 2000; Hosoda et al. 2002), are consistent with a redundant function of B-type ARRs. In addition, nine amino acids, which were identified in ARR10 (SEQ ID NO: 3) to be most likely in direct contact with the DNA are particularly well conserved in the B-type response regulators and the pseudo response regulators (FIG. 1a). Phylogenetic analysis separates the B-type ARRs into three distinct subgroups, which is similar to the outcome of previous analyses using not the DNA-binding but the response regulator domains for comparison (FIG. 1b and (Mason et al., 2004; Tajima et al., 2004). One large subgroup contains seven B-type ARRs. ARR19 (SEQ ID NO: 9) and ARR20 (SEQ ID NO: 10) as well as ARR21 (SEQ ID NO: 11) and ARR13 (SEQ ID NO: 6) form separate groups (FIG. 1b). ARR13 was included in this alignment although Pfam did not detect a MYB domain in this protein using the default cut off of 1.

Example 2

Generating the ARR1-SRDX Fusion Protein and Transgenic Plants Expressing the Fusion Protein Example 2.1 Generating the ARR1-SRDX Fusion Protein The protein coding region of the ARR1 gene was amplified by PCR using a cDNA library from *Arabidopsis thaliana* C24 (Minet et al., 1992). The DNA fragment coding for the SRDX peptide (SEQ ID NO: 52: LDLDLELRLGFA; (Hiratsu et al., 2003)) was synthesized with a TAA stop codon and a Bsr GI restriction site at the 3' end and an in frame Hha I site at the 5' end. The ARR1 gene was isolated from the plasmid pDONR201 (Invitrogen, Carlsbad, USA) by restriction digestion with Bsr GI and the resulting fragment was further digested with Hha I. The appropriate DNA fragments were ligated and recloned into entry vector pDONR201 (Invitrogen, Carlsbad, USA). The resulting ARR1-SRDX gene was shuttled into the vector pB2GW7 (Invitrogen, Carlsbad, USA) for overexpression under the control of the 35S promoter.

Example 2.2 Generating the Transgenic Plants Expressing the ARR1-SRDX Fusion Protein The construct obtained in 2.1 was transformed using *Agrobacterium tumefaciens* mediated transformation into wild-type *Arabidopsis* plants (Col-0) by the floral dip method (Clough and Bent, 1998).

More than 10 independent transgenic lines with a distinct phenotype were recovered of which two lines, ARR1_S_8 and ARR1_S_10, were characterized in more detail. Genetic analysis showed that ARR1_S_8 contained a single T-DNA insertion locus and ARR1_S_10 carried insertions at two independent loci.

Example 2.3 RNA Extraction and Analysis

Total RNA was extracted from three week old seedlings as described (Brenner et al., 2005). For Northern blot analysis, 20 μg of RNA were separated in a denaturing agarose-formaldehyde gel (1.2%) containing 10% of 10×MOPS and 3% of 37% formaldehyde and transferred to a Hybond-N+ nylon membrane (Amersham, Little Chalfont, UK). The fixed membranes were then hybridized with radioactive [α-32P] dCTP labelled DNA. Hybridization was performed at 68° C. in a phosphate buffer containing 7% SDS and 1% BSA. Washing was done with 2×SSC, and 0.2×SSC, 0.1% SDS at 65° C. As a control for loading, blots were reprobed with an actin 2 probe. The SRDX-specific probe was prepared by amplifying the SRDX containing segment of the ARR1-SRDX gene using the following primers 5'-ATGAGCG-CACTCGATC-3' (SEQ ID NO: 58) and 5'-AGTTTGTA-CAAGAAAG-3' (SEQ ID NO: 59).

Northern blot analysis using the SRDX-specific probe showed the expression of the ARR1-SRDX transcript in both lines (FIG. 2). The steady state transcript level was higher in ARR1_S__8 compared to ARR1_S__10. The wild type control showed no signal for the ARR1-SRDX transcript confirming the specificity of the used probe (FIG. 2).

Example 3

Phenotypical Characterization of the Transgenic Plants Expressing the ARR1-SRDX Fusion Protein

Example 3.1 Plant Material and Growth Conditions

Plants of the Columbia (Col-0) accession of *Arabidopsis thaliana* was used as wild type. The plants were grown in the greenhouse on soil at 22° C. under long-day conditions (16 h light/8 h dark). For in vitro experiments, seeds were surface-sterilized with saturated calcium hypo-chlorate solution. After sowing they were kept at 4° C. for 3 d in the dark and then exposed to white light (75 μE). Seedlings were grown at 22° C. on media containing 1× Murashige and Skoog (MS) salts, 3% sucrose, 0.05% MES and 0.9% agarose (Merck) unless specified otherwise. For flowering phenotype total number of rosette leaves was counted upon flower bud initiation.

Example 3.2 Phenotypic Characterization: Shoot

The transgenic plants expressing the ARR1-SRDX construct displayed a strong pleiotropic shoot phenotype. Plants were generally smaller in habitus and showed enhanced branching of the shoot. This effect was stronger in line ARR1_S__8 than in ARR1_S__10 (FIG. 3*a*). The leaves of the dominant repressors were strongly reduced in both size and number when compared to the wild-type plants. In the strongest expressing line ARR1_S__8 even the true leaves were only about the size of the cotyledons in the wild type (FIG. 3*b*). In addition, the formation of new leaves was slow in the transgenic lines. While the wild-type plant had on average nine rosette leaves 20 DAG (days after germination), the ARR1-SRDX expressing plants had only seven leaves at that time point (FIG. 3*c*).

Example 3.3 Phenotypic Characterization: Root System

*Arabidopsis* seeds were grown on vertical plates containing different concentration of BA ranging from 0.01 μM to 1.0 mM. 0.1% dimethyl sulfoxide (DMSO) was included as vehicle control. The primary root lengths were marked on day four and nine after germination. Photographs were taken with a digital camera (Nikon Coolpix 8800) and root lengths were determined using Scion Image program version beta 4.02 (www.scioncorp.com). The number of lateral roots emerging from the epidermis of the primary root was counted under a microscope ten DAG. The experiments were performed using three independent replicates and 15 seedlings in each replicate.

Opposite to the reduced shoot size, ARR1-SRDX transgenic plants showed a generally enhanced root system when compared to the wild type (FIG. 4*a*). While the ARR_S__8 plants had only a slightly longer primary root than the wild type, the primary root of line ARR_S__10 was more than 30% longer (34.9±3.1 mm in wild type compared to 51.9±6.6 mm in line ARR_S__10; FIG. 4*b*). The difference between the transgenic lines and the wild type was more pronounced in the number of lateral roots. 10 DAG plants of line ARR1_S__8 had developed about twice as much lateral roots as the wild type and line ARR1_S__10 had even about three times more (13.2±1.9 lateral roots compared to 4.8±1.1 lateral roots in wild type)(FIG. 4*c*).

Example 3.4 Phenotypic Characterization: Reproductive Development

The 35S:ARR1_SRDX transgenic plants flowered earlier than wild type (FIG. 5*a*). To quantify this phenotype, the number of days from germination to the opening of the first flower bud was counted. In the wild type the first flower buds opened 19 days after germination. In contrast, both lines 8 and 10 flowered already around 14 days after germination (FIG. 5*b*) In the 35S:ARR1-SRDX transgenic plants, all reproductive organs were reduced in size. Both, the flowers and the siliques were smaller compared to wild type. This was more pronounced in line ARR1—S__8, where the flowers were only half the size of the wild type (FIG. 5*c*). While the sepals showed only a relative minor reduction in size, the petal size was strongly diminished in line ARR1_S__8. The phenotype of line ARR1_S__10 was intermediate (FIG. 5*c*). The smaller flowers of the 35S:ARR$_1$—SRDX plants gave rise to siliques which were smaller than those of wild type. Here again the phenotype of line ARR1_S__8 was stronger. The siliques of this line were about 30% of the length of the wild type. The shape differed also from the wild type as it was twisted and crooked (FIG. 5*d*). The phenotype of line ARR1_S__10 was intermediate as the reduction of the silique size was not as dramatic as in line ARR1_S__8 and the shape resembled more the wild type (FIG. 5*d*).

Determination of seed size and seed weight was carried out as described by Riefler et al. (2006) and Werner et al. (2003), respectively. Seed size of wild type and ARR1-SRDX overexpressers was determined measuring length and width of 60 seeds harvested from two different plants. The volume was estimated by calculating with the formula for a spheroid (volume=4/3·length·width·depth). Biomass of seed was weighed by using a fine Balance LE244S (Sartorius, Göttingen, Germany). The weight of one seed was calculated from the weight of pools of 200 seeds. The sample size for each genotype was ten.

While the number of seeds obtained by selfing was considerably lower in the 35S:ARR1-SRDX plants (data not shown), the seed themselves showed an increased biomass, which was 40% and 50% higher in the lines ARR1_S__8 and ARR1_S_10, respectively (FIG. 5g). All transgenic seeds showed a high germination capacity.

Example 3.5 Phenotypic Characterization: Long Term Response to Cytokinin

The phenotype of the 35S:ARR1-SRDX plants is reminiscent of plants with a reduced cytokinin signaling (Higuchi et al., 2004; Nishimura et al., 2004; Riefler et al., 2006). To test further whether the cytokinin signaling pathway is impaired and whether this affects specific responses, we carried out several cytokinin sensitivity assays.

Cytokinin is known to delay the onset of leaf senescence and to increase the chlorophyll retention in detached leaves incubated in the dark (Richmond and Lang, 1957; Riefler et al., 2006).

The chlorophyll retention assay was performed as described by (Riefler et al., 2006). Either the sixth or the seventh leaf was detached from 24-days-old in vitro grown seedlings and floated on distilled water supplemented with 0, 0.01, 0.1, 0.5, 1.0 or 5.0 µM BA in 0.1% DMSO in small Petri dishes for 10 d at RT in the dark. Three replicates of each genotype, each consisting of five leaves were taken for measurement. Chlorophyll was extracted with methanol for 24 h in the dark. The amount of chlorophyll was measured with a spectrophotometer, normalized to fresh weight, and the chlorophyll content was calculated as described (Porra et al., 1989).

Detached wild type leaves kept in the dark for 10 days lost more than 80% of their chlorophyll compared to fresh leaves (FIG. 6). The addition of increasing amounts of cytokinin reversed this effect. In wild type leaves 0.1 µM BA strongly increased chlorophyll retention and at 5 µM BA the chlorophyll level of dark-incubated detached leaves was similar to fresh leaves. In contrast, in both 35S:ARR1-SRDX lines the addition of cytokinin to the media caused only a small increase in chlorophyll retention, even at the highest concentration (FIGS. 6a, b), indicating that the cytokinin sensitivity in the leaves has been lost almost completely.

To investigate the cytokinin response in roots, seedlings of wild type and the 35S:ARR1-SRDX lines were grown on media containing increasing amounts of cytokinin. On control media without cytokinin the transgenic seedlings developed a longer primary root compared to the wild type (FIG. 4a). The relative difference in root length increased with increasing cytokinin concentrations (FIG. 7a). Seedlings of line ARR1_S_8 displayed a higher resistance to cytokinin than line ARR1_S_10. At the highest tested cytokinin concentration (1 µM BA), the root length of the wild type plants was reduced by 75% compared to the control plants. In contrast, in ARR1_S_8 the root length was only reduced by around 55%. However, the sensitivity to cytokinin, while being clearly reduced was not completely eliminated in either 35S:ARR1-SRDX line (FIG. 7b). Furthermore it was tested if the lateral root formation was altered in the presence of the hormone. In all seedlings the addition of cytokinin to the media led to a dramatic decrease in the number of lateral roots (FIG. 7a). But whereas the lateral root formation of the wild type was almost totally repressed already at 0.01 µM cytokinin, lateral root formation of both 35S:ARR1-SRDX lines was only halved at this cytokinin concentration. They developed about the same number of lateral roots as the wild type on cytokinin-free medium (FIG. 7c). At 0.1 µM BA the wild type was unable to produce lateral roots, while the dominant repressor lines still showed a significant number (FIG. 7c). It is interesting to note that although without cytokinin line ARR1_S_10 forms more lateral roots than line ARR1_S_8 this difference between the transgenic lines disappeared when exogenous cytokinin was added (FIG. 7c).

Example 3.6 Phenotypic Characterization: Rapid Response to Cytokinin

The phenotypic changes and cytokinin bioassays described above show altered long term responses to the hormone. We were interested to analyze whether also rapid cytokinin responses were altered in the 35S:ARR1-SRDX lines and used a primary cytokinin response gene to test this. The transcript level of ARR5, which encodes a member of the A-type ARRs, is rapidly induced by cytokinin (D'Agostino et al., 2000) and it has often been used as a molecular maker for the cytokinin response in *Arabidopsis* (D'Agostino et al., 2000; Romanov et al., 2002). It was also shown that the A-type ARRs are target genes of the B-type ARRs (Hwang and Sheen, 2001). FIG. 8 shows that the transcript level of ARR5 was rapidly and strongly induced in wild type seedlings following the application of cytokinin. The early induction of ARR5 was strongly diminished in both transgenic lines (FIG. 8).

Example 3.7 Comparison of 35S:ARR1-SRDX Transgenics with Known Signaling Mutants The phenotype of the 35S:ARR1-SRDX transgenic plants resembled in various aspects the phenotype of cytokinin receptor triple mutants (Higuchi et al., 2004; Nishimura et al., 2004; Riefler et al., 2006). As in those mutants the shoot growth in 35S:ARR1-SRDX plants was strongly retarded, with a reduced plastochrone and the formation of a reduced number of leaves of a smaller size when compared to the wild type (Higuchi et al., 2004; Nishimura et al., 2004; Riefler et al., 2006). Plants of 35S:ARR1-SRDX lines have also larger seeds as have cytokinin receptor mutants (Riefler et al., 2006). In addition, comparable phenotypic changes were seen in shoots of *Arabidopsis* plants with reduced cytokinin content (Werner et al., 2003). Retarded shoot growth was also reported for ARR2 mutant plants (Hass et al., 2004), however not as strong as in the dominant repressor lines reported here.

Cytokinins are known to play a crucial role in plant senescence, which is in part mimicked by the dark-induced chlorophyll retention assay we used in our analysis (Riefler et al., 2006). Previous analysis using different cytokinin receptor mutant combinations determined AHK3 to play crucial roles mediating the cytokinin function in this process. 35S:ARR1-SRDX plants show a complete resistance to cytokinin in the chlorophyll retention assay, which is similar to the phenotype of ahk2 ahk3 receptor mutants (Riefler et al., 2006). This is consistent with the overall strong activity of the ARR1-SRDX repressor in shoot tissues and indicates that most if not all of the cytokinin activities in regulating chlorophyll retention are dependent on B-type ARRs. In particular it indicates that the ARR2 function is suppressed in leaves as this B-type ARR has been shown to play a role in mediating cytokinin-dependent chlorophyll retention (Kim et al., 2006)

ARR2 mutant plants flower earlier than wild type (Hass et al., 2004), while triple mutants and cytokinin-deficient plants show retarded flowering. It could be that the negative regulatory function of ARR2 in controlling flowering is lost by its repression.

The shoot morphology as well as the complete resistance to cytokinin of leaves in the chlorophyll retention assay indicates a very strong suppressor activity of the ARR1-SRDX protein. A shoot phenotype was not reported even for various triple B-type arr mutants (Mason et al., 2005).

Cytokinin greatly influences root structure and growth. In cytokinin deficient plants as well as in receptor and B-type ARR signaling mutants, the primary roots are longer and more lateral roots are formed (Higuchi et al., 2004; Mason et al., 2005; Nishimura et al., 2004; Riefler et al., 2006; Werner et al., 2003). The same is true also for the dominant repressor plants reported here. Also the reduced cytokinin sensitivity of roots of 35S:ARR1-SRDX transgenic lines is similar to changes seen in various mutants with a reduced cytokinin status (Werner et al., 2003). However, Mason and colleagues notice, that the inclusion of an arr2 knockout allele in arr mutant combinations caused a reduction of the strength of the phenotype, indicating that ARR2 might have an antagonistic function to the other B-type ARRs in regulating root elongation and rootbranching (Mason et al., 2005). As in the dominant repression plants ARR2, as a close homologue of ARR1, is very likely to be affected, this would explain the somewhat weaker root phenotype in the 35S:ARR1-SRDX transgenic plants compared to the arr1, arr10, arr12 triple mutant combination (Mason et al., 2005).

The inducibility of the cytokinin response gene ARR5 was clearly dampened in both dominant repressor lines, indicating that the ARR1-SRDX protein interferes directly with the activity of transcription factors mediating the cytokinin response. The reduction of gene induction is comparable to the arr1, 10, 12 triple mutant (Mason et al., 2005), but clearly weaker than that of the receptor triple mutants (Higuchi et al., 2004). This may indicate that transcription of the A-type ARRs might be also regulated via an AHK dependent, but B-type ARR independent pathway. In fact, it was recently shown that the CRFs are regulated in an AHK dependent manner by cytokinin. The six members of this class of transcription factors rapidly localize to the nucleus upon cytokinin treatment and have been shown to redundantly regulate several aspects of plant development. The function of this family of transcription factors is only partially overlapping with those of the B-type ARRs. However, ARR5 was shown to be one of the genes transcriptionally regulated by both gene families. This might explain, why in the 35S:ARR1-SRDX plans the induction of ARR5 is only dampened and not completely abolished (FIG. 8 +(Rashotte et al., 2006).

Example 4

The ARR1-SRDX Fusion Protein Suppresses Cytokinin-Dependent Induction of a Cytokinin Response Gene Example 4.1 Protoplast Transactivation Assay For the protoplast assay, the reporter plasmid was generated by amplifying the 1000 by fragment directly upstream of the ARR6 gene using the forward primer 5'-GCAAGCTTA-CAATCACAACAGCTCATGAACAAAATC-3' (SEQ ID NO: 68) and the reverse primer 5'-GCTCTAGAGAAAC-CATGGTGGCAGTGGTTGGGC-3' (SEQ ID NO: 69). The resulting PCR product was digested with HindIII and XbaI and ligated into the pBT10-GUS vector (Sprenger-Haussels and Weisshaar, 2000). The 35S:ARR1 gene was generated by shuttling the ARR1 gene from the pDONR201-ARR1 vector (Dortay et al., 2006) into the pB2GW7 vector (Karimi et al., 2002) for expression under the control of the 35S promoter. A dominant repressor for the B-type ARRs was generated by introducing a 36 by long DNA sequence encoding the SRDX domain (LDLDLELRLGFA (SEQ ID NO: 52); Hiratsu et al., 2003) 20 nucleotides 5' of the ARR1 stop codon (FIG. 10).

Protoplast isolation and transformation was carried out according to the method described by Hwang and Sheen (Hwang and Sheen, 2001). For isolation of mesophyll protoplasts 4-5 weeks old rosette leaves were used. Transformation of protoplasts was mediated by 40% PEG solution. For cytokinin treatment protoplasts were incubated overnight with 500 nM trans-zeatin (tZ). For the transactivation assays, 9 μg of the ARR6: GUS reporter plasmid and 14 μg of each effector plasmid carrying 35S:ARR1 and 35S:ARR1-SRDX were used. For normalization 3 μg of a plasmid harboring the 35S:NAN gene (Kirby and Kavanagh, 2002) was added. Both GUS and NAN enzyme assays were performed according to Kirbay and Kavanagh (Kirby and Kavanagh, 2002). The ratios of GUS and NAN activities were calculated as relative GUS/NAN activity units.

The in planta effect of the ARR1-SRDX was first examined in a protoplast transactivation assay (Ehlert et al., 2006), using a 1000 by promoter fragment upstream of the transcriptional start of ARR6, a primary cytokinin response gene (Hwang and Sheen, 2001), fused to the GUS reporter gene. The addition of cytokinin resulted in a more than threefold induction of the reporter gene expression compared to the non-induced condition (FIG. 9). Co-transfection with ARR1 under the control of a 35S promoter led to a strong increase in GUS activity even in the absence of cytokinin. The addition of cytokinin caused a further, twofold increase of the GUS activity, indicating that ARR1 mediates the cytokinin response in this assay. In contrast, the expression of ARR1-SRDX under the control of a 35S promoter effectively suppressed the cytokinin induction of GUS expression. Furthermore, ARR1-SRDX completely abolished the ARR1-caused expression of the reporter gene in the absence and presence of cytokinin (FIG. 9). The expression of the GUS reporter gene under the control of a 35S promoter was not cytokinin inducible. These results clearly demonstrate that ARR1-SRDX is a dominant repressor of the cytokinin primary transcriptional response in planta.

INDUSTRIAL APPLICABILITY

Previous studies using the CRES-Technology have shown its usefulness for studying function of closely related transcription factors (Chandler and Werr, 2003; Hiratsu et al., 2003). However, in no case more than two transcription factors with overlapping functions were studied. In the present invention it was shown for the first time that this technology can be used to achieve transcriptional repression in larger transcription factor families. In fact, 35S:ARR1-SRDX transgenic plants show a stronger loss of function phenotype than do knockout mutants in single B-type ARR genes or various double and triple knockout combinations (cf. Hass et al., 2004; Horák et al., 2003; Mason et al., 2005; Sakai et al., 2001). This effect is not based on co-suppression, as the level of ARR1 transcript was not decreased in the 35S:ARR1-SRDX lines.

In conclusion, the present invention provides transgenic plants and methods for their production which are superior over the single, double and triple mutants known from the prior art. The transgenic plants of the present invention exhibit advantageous properties such as enhanced seed size, enhanced seed filling, reduced seed loss, enhanced root mass, enhanced root length, enhanced root branching, reduced germination time, altered leaf senescence and/or altered timing of reproduction.

REFERENCES

Aida, M., Ishida, T., Fukaki, H., Fujisawa, H. and Tasaka, M. (1997) Genes involved in organ separation in *Arabidopsis*: an analysis of the cup-shaped cotyledon mutant. *Plant Cell,* 9, 841-857.

Brenner, W. G., Romanov, G. A., Köllmer, I., Bürkle, L. and Schmülling, T. (2005) Immediate-early and delayed cytokinin response genes of *Arabidopsis thaliana* identified by genome-wide expression profiling reveal novel cytokinin-sensitive processes and suggest cytokinin action through transcriptional cascades. *Plant J,* 44, 314-333.

Chandler, J. W. and Werr, W. (2003) When negative is positive in functional genomics. *Trends Plant Sci,* 8, 279-285.

Clough, S. J. and Bent, A. F. (1998) Floral dip: a simplified method for Agrobacterium-mediated transformation of *Arabidopsis thaliana. Plant J.,* 16, 735-743.

D'Agostino, I. B., Deruere, J. and Kieber, J. J. (2000) Characterization of the response of the *Arabidopsis* response regulator gene family to cytokinin. *Plant Physiol.,* 124, 1706-1717.

Dortay, H., Mehnert, N., Bürkle, L., Schmülling, T., and Heyl, A. (2006). Analysis of protein interactions within the cytokinin-signaling pathway of *Arabidopsis thaliana.* FEBS Journal 273, 4631-4644.

Ehlert, A., Weltmeier, F., Wang, X., Mayer, C. S., Smeekens, S., Vicente-Carbajosa, J., and Dröge-Laser, W. (2006). Two-hybrid protein-protein interaction analysis in *Arabidopsis* protoplasts: establishment of a heterodimerization map of group C and group S bZIP transcription factors. Plant J. 46, 890-900.

Ferreira, F. J. and Kieber, J. J. (2005) Cytokinin signaling. *Curr. Opin. Plant Biol.,* 8, 518-525.

Finn, R. D., Mistry, J., Schuster-Bockler, B., Griffiths-Jones, S., Hollich, V., Lassmann, T., Moxon, S., Marshall, M., Khanna, A., Durbin, R., Eddy, S. R., Sonnhammer, E. L. and Bateman, A. (2006) Pfam: clans, web tools and services. *Nucleic Acids Res,* 34, D247-251.

Grefen, C. and Harter, K. (2004) Plant two-component systems: principles, functions, complexity and cross talk. *Planta,* 219, 733-742.

Hass, C., Lohrmann, J., Albrecht, V., Sweere, U., Hummel, F., Yoo, S. D., Hwang, I., Zhu, T., Schäfer, E., Kudla, J. and Harter, K. (2004) The response regulator 2 mediates ethylene signalling and hormone signal integration in *Arabidopsis. EMBO J.,* 23, 3290-3302.

Heyl, A., Werner, T. and Schmulling, T., eds. (2006) *Cytokinin metabolism and signal transduction.* Oxford: Blackwell Publishing Ltd.

Higuchi, M., Pischke, M. S., Mahonen, A. P., Miyawaki, K., Hashimoto, Y., Seki, M., Kobayashi, M., Shinozaki, K., Kato, T., Tabata, S., Helariutta, Y., Sussman, M. R. and Kakimoto, T. (2004) In planta functions of the *Arabidopsis* cytokinin receptor family. *Proc. Natl. Acad. Sci. USA,* 101, 8821-8826.

Hiratsu, K., Matsui, K., Koyama, T. and Ohme-Takagi, M. (2003) Dominant repression of target genes by chimeric repressors that include the EAR motif, a repression domain, in *Arabidopsis. Plant J,* 34, 733-739.

Horák, J., Brzobohatý, B. and Lexa, M. (2003) Molecular and physiological characterisation of an insertion mutant in the ARR21 putative response regulator gene from *Arabidopsis thaliana. Plant Biol.,* 5, 245-254.

Hosoda, K., Imamura, A., Katoh, E., Hatta, T., Tachiki, M., Yamada, H., Mizuno, T. and Yamazaki, T. (2002) Molecular structure of the GARP family of plant Myb-related DNA binding motifs of the *Arabidopsis* response regulators. *Plant Cell,* 14, 2015-2029.

Hwang, I., Chen, H. C. and Sheen, J. (2002) Two-component signal transduction pathways in *Arabidopsis. Plant Physiol.,* 129, 500-515.

Hwang, I. and Sakakibara, H. (2006) Cytokinin biosynthesis and perception. *Planta,* 126, 528-538.

Hwang, I. and Sheen, J. (2001) Two-component circuitry in *Arabidopsis* cytokinin signal transduction. *Nature,* 413, 383-389.

Imamura, A., Kiba, T., Tajima, Y., Yamashino, T. and Mizuno, T. (2003) In vivo and in vitro characterization of the ARR11 response regulator implicated in the His-to-Asp phosphorelay signal transduction in *Arabidopsis thaliana. Plant Cell Physiol.,* 44, 122-131.

Kakimoto, T. (2003) Perception and signal transduction of cytokinins. *Annu. Rev. Plant Biol.,* 54, 605-627.

Karimi, M., Inze, D., and Depicker, A. (2002). GATEWAY vectors for *Agrobacterium*-mediated plant transformation. Trends Plant Sci. 7, 193-195.

Kazan, K. (2006) Negative regulation of defence and stress genes by EAR-motif-containing repressors. *Trends Plant Sci,* 11, 109-112.

Kirby, J., and Kavanagh, T. A. (2002). NAN fusions: a synthetic sialidase reporter gene as a sensitive and versatile partner for GUS. Plant J. 32, 391-400.

Kumar, S., Tamura, K., and Nei, M. (2004). MEGA3: Integrated software for Molecular Evolutionary Genetics Analysis and sequence alignment. Brief Bioinform. 5, 150-163.

Larsen, P. B. and Chang, C. (2001) The *Arabidopsis* eer1 mutant has enhanced ethylene responses in the hypocotyl and stem. *Plant Physiol,* 125, 1061-1073.

Lohrmann, J., Sweere, U., Zabaleta, E., Bäurle, I., Keitel, C., Kozma, B. L., Brennicke, A., Schäfer, E., Kudla, J. and Harter, K. (2001) The response regulator ARR2: A pollen-specific transcription factor involved in the expression of nuclear genes for components of mitochondrial complex I in *Arabidopsis. Mol. Genet. Genomics,* 265, 2-13.

Makino, S., Kiba, T., Imamura, A., Hanaki, N., Nakamura, A., Suzuki, T., Taniguchi, M., Ueguchi, C., Sugiyama, T., and Mizuno, T. (2000). Genes encoding pseudo-response regulators: insight into His-to-Asp phosphorelay and circadian rhythm in *Arabidopsis thaliana.* Plant Cell Physiol. 41, 791-803.

Mason, M. G., Li, J., Mathews, D. E., Kieber, J. J. and Schaller, G. E. (2004) Type-B response regulators display overlapping expression patterns in *Arabidopsis. Plant Physiol.,* 135, 927-937.

Mason, M. G., Mathews, D. E., Argyros, D. A., Maxwell, B. B., Kieber, J. J., Alonso, J. M., Ecker, J. R. and Schaller, G. E. (2005) Multiple type-B response regulators mediate cytokinin signal transduction in *Arabidopsis. Plant Cell,* 17, 3007-3018.

Minet, M., Dufour, M. E. and Lacroute, F. (1992) Complementation of *Saccharomyces cerevisiae* auxotrophic mutants by *Arabidopsis thaliana* cDNAs. *Plant J,* 2, 417-422.

Mizuno, T. (2004) Plant response regulators implicated in signal transduction and circadian rhythm. *Curr. Opin. Plant Biol.,* 7, 499-505.

Mok, D. W. and Mok, M. C. (2001) Cytokinin metabolism and action. *Annu. Rev. Plant Physiol. Plant Mol. Biol.,* 52, 89-118.

Nishimura, C., Ohashi, Y., Sato, S., Kato, T., Tabata, S. and Ueguchi, C. (2004) Histidine kinase homologs that act as cytokinin receptors possess overlapping functions in the regulation of shoot and root growth in *Arabidopsis*. *Plant Cell*, 16, 1365-1377.

Ohta, M., Matsui, K., Hiratsu, K., Shinshi, H. and Ohme-Takagi, M. (2001) Repression domains of class II ERF transcriptional repressors share an essential motif for active repression. *Plant Cell*, 13, 1959-1968.

Porra, R. J., Thompson, W. A. and Kriedemann, E. (1989) Determination of accurate extinction coefficients and simultaneous equations for assaying chlorophylls a and b with four different solvents: Verification of the concentrations of chlorophyll standarts fy atomic adsorption spectroscopy. *Biochchim Biophys Acta*, 975, 384-394.

Rashotte, A. M., Mason, M. G., Hutchison, C. E., Ferreira, F. J., Schaller, G. E. and Kieber, J. J. (2006) A subset of *Arabidopsis* AP2 transcription factors mediates cytokinin responses in concert with a two-component pathway. *Proc Natl Acad Sci USA*, 103, 11081-11085.

Richmond, A. E. and Lang, A. (1957) Effect of kinetin on protein content and survival of detached *Xanthium* leaves. *Science* (Washington D.C.), 125, 650.

Riechmann, J. L., Heard, J., Martin, G., Reuber, L., Jiang, C. Z., Keddie, J., Adam, L., Pineda, O., Ratcliffe, O. J., Samaha, R. R., Creelman, R., Pilgrim, M., Broun, P., Zhang, J. Z., Ghandehari, D., Sherman, B. K. and Yu, G. L. (2000) *Arabidopsis* transcription factors: Genome-wide comparative analysis among eukaryotes. *Science* (*Wash. D C*), 290, 2105-2110.

Riefler, M., Novak, O., Strnad, M. and Schmülling, T. (2006) *Arabidopsis* Cytokinin Receptor Mutants Reveal Functions in Shoot Growth, Leaf Senescence, Seed Size, Germination, Root Development, and Cytokinin Metabolism. *Plant Cell*, 18, 40-54.

Romanov, G. A., Kieber, J. J. and Schmulling, T. (2002) A rapid cytokinin response assay in *Arabidopsis* indicates a role for phospholipase D in cytokinin signalling. *FEBS Lett.*, 515, 39-43.

Sakai, H., Aoyama, T. and Oka, A. (2000) *Arabidopsis* ARR1 and ARR2 response regulators operate as transcriptional activators. *Plant J*, 24, 703-711.

Sakai, H., Honma, T., Aoyama, T., Sato, S., Kato, T., Tabata, S. and Oka, A. (2001) ARR1, a transcription factor for genes immediately responsive to cytokinins. *Science*, 294, 1519-1521.

Smalle, J., Haegman, M., Kurepa, J., Van Montagu, M. and Straeten, D. V. (1997) Ethylene can stimulate *Arabidopsis* hypocotyl elongation in the light. *Proc Natl Acad Sci USA*, 94, 2756-2761.

Sprenger-Haussels, M., and Weisshaar, B. (2000). Transactivation properties of parsley proline-rich bZIP transcription factors. Plant J. 22, 1-8.

Sweere, U., Eichenberg, K., Lohrmann, J., Mira-Rodado, V., Baurle, I., Kudla, J., Nagy, F., Schafer, E. and Harter, K. (2001) Interaction of the response regulator ARR4 with phytochrome B in modulating red light signaling. *Science*, 294, 1108-1111.

Tajima, Y., Imamura, A., Kiba, T., Amano, Y., Yamashino, T. and Mizuno, T. (2004) Comparative studies on the type-B response regulators revealing their distinctive properties in the His-to-Asp phosphorelay signal transduction of *Arabidopsis thaliana*. *Plant Cell Physiol.*, 45, 28-39.

Takada, S., Hibara, K., Ishida, T. and Tasaka, M. (2001) The CUP-SHAPED COTYLEDON1 gene of *Arabidopsis* regulates shoot apical meristem formation. *Development*, 128, 1127-1135.

Thompson, J. D., Higgins, D. G. and Gibson, T. J. (1994) CLUSTAL W: improving the sensitivity of progressive multiple sequence alignment through sequence weighting, position-specific gap penalties and weight matrix choice. *Nucleic Acids Res.*, 22, 4673-4680.

Tiwari, S. B., Hagen, G. and Guilfoyle, T. J. (2004) Aux/IAA proteins contain a potent transcriptional repression domain. *Plant Cell*, 16, 533-543.

To, J. P., Haberer, G., Ferreira, F. J., Deruere, J., Mason, M. G., Schaller, G. E., Alonso, J. M., Ecker, J. R. and Kieber, J. J. (2004) Type-A *Arabidopsis* response regulators are partially redundant negative regulators of cytokinin signaling. *Plant Cell*, 16, 658-671.

Werner, T., Motyka, V., Laucou, V., Smets, R., Van, O. H. and Schmülling, T. (2003) Cytokinin-deficient transgenic *Arabidopsis* plants show multiple developmental alterations indicating opposite functions of cytokinins in the regulation of shoot and root meristem activity. *Plant Cell*, 15, 2532-2550.

The invention claimed is:

1. A polynucleotide comprising a nucleic acid sequence encoding a fusion protein comprising;
   (a) a DNA binding factor capable of specifically binding to a B-type Arabidopsis response regulator (ARR) DNA motif, the DNA motif comprising the sequence 5'-(A/G)GAT(T/C)-3', wherein said DNA binding factor comprises a DNA binding domain of a B-type ARR, wherein said DNA binding domain is selected from the group consisting of:
      (i) DNA binding domains of ARR1 according to SEQ ID NO: 1, ARR2 according to SEQ ID NO: 2, ARR10 according to SEQ ID NO: 3, ARR11 according to SEQ ID NO: 4, ARR12 according to SEQ ID NO: 5, ARR13 according to SEQ ID NO: 6, ARR14 according to SEQ ID NO: 7, and ARR18 according to SEQ ID NO: 8 and
      (ii) a homologue of a DNA binding domain according to (i) from a plant other than Arabidopsis thaliana capable of specifically binding to a B-type ARR DNA motif, wherein said homologue exhibits at least 70% sequence identity to the DNA-binding domain of ARR1 of SEQ ID NO: 1 and when aligned to the DNA binding domain of ARR1 according to SEQ ID NO: 1, has the same amino acid as SEQ ID NO: 1 in the amino acid positions corresponding to positions 1, 3, 4, 41, 44, 45, 47, 48 and 49 of SEQ ID NO: 1 and
   (b) a transcriptional repressor domain, wherein said transcriptional repressor domain is an EAR motif.

2. A vector comprising the polynucleotide of claim 1.

3. The vector of claim 2, wherein the polynucleotide is operatively linked to expression control sequences allowing expression of the nucleic acid sequence encoding the fusion protein in prokaryotic and/or eukaryotic host cells.

4. An isolated cell comprising the polynucleotide of claim 1.

5. A transgenic plant comprising the vector of claim 3.

6. Parts, cells, or seeds of the transgenic plant according to claim 5, wherein said parts, cells or seeds comprise said vector.

7. Plants or propagating material thereof regenerated from the transgenic plant according to claim 5, wherein said plants or propagating material thereof comprise said vector.

8. Process for making a transgenic plant, parts, cells, or seeds thereof or propagating material according to any one of claims 5-7, comprising the step of transforming a cell or cells of a plant with a vector comprising a polynucleotide comprising a nucleic acid sequence encoding a fusion protein comprising;
   (a) a DNA binding factor capable of specifically binding to a B-type Arabidopsis response regulator (ARR) DNA motif, the DNA motif comprising the sequence 5'-(A/G)GAT(T/C)-3', wherein said DNA binding factor comprises a DNA binding domain of a B-type ARR, wherein said DNA binding domain is selected from the group consisting of:
      (i) DNA binding domains of ARR1 according to SEQ ID NO: 1, ARR2 according to SEQ ID NO: 2, ARR10 according to SEQ ID NO: 3, ARR11 according to SEQ ID NO: 4, ARR12 according to SEQ ID NO: 5, ARR13 according to SEQ ID NO: 6, ARR14 according to SEQ ID NO: 7, and ARR18 according to SEQ ID NO: 8 and
      (ii) a homologue of a DNA binding domain according to (i) from a plant other than Arabidopsis thaliana capable of specifically binding to a B-type ARR DNA motif, wherein said homologue exhibits at least 70% sequence identity to the DNA-binding domain of ARR1 of SEQ ID NO: 1 and when aligned to the DNA binding domain of ARR1 according to SEQ ID NO: 1, has the same amino acid as SEQ ID NO: 1 in the amino acid positions corresponding to positions 1, 3, 4, 41, 44, 45, 47, 48 and 49 of SEQ ID NO: 1 and
   (b) a transcriptional repressor domain, wherein said transcriptional repressor domain is an EAR motif
   and wherein the polynucleotide is operably linked to expression control sequences allowing expression of the nucleic acid sequence.

9. The process according to claim 8, further comprising the step of selecting transformed cells and regenerating of transformed plants from the cells.

10. A method for enhancing the seed size of a plant and/or the seed filling of a plant, comprising:
   culturing the transgenic plant, parts, cells, or seeds thereof or propagating material according to any one of claims 5-7 under culturing conditions;

growing the plant; and allowing seeds to be produced.

11. A method for altering shoot architecture, for altering leaf senescence and/or for altering the timing of reproduction, comprising culturing the transgenic plant, parts, cells or seeds thereof or propagating material according to any one of claims 5-7 under culturing conditions.

12. A method for enhancing the seed size of a plant and/or the seed filling of a plant, comprising the steps of
   (a) introducing by genetic engineering into the plant the vector according to claim 3;
   (b) expressing the polynucleotide within said vector;
   (c) growing the plant; and
   (d) allowing seeds to be produced.

13. The method of claim 12, wherein the expression of the polynucleotide is controlled by a tissue-specific regulatory element.

14. The method of claim 13, wherein the tissue for which the regulatory element is specific is selected from the group consisting of root tissue, embryo tissue, endosperm tissue, and aleurone tissue.

15. A method for making seeds of enhanced size, with enhanced seed filling, comprising culturing the transgenic plant, parts, cells, or seeds thereof or propagating material according to any one of claims 5-7 under culturing conditions, wherein a plant is grown therefrom, wherein seeds are allowed to be produced and wherein preferably mature seeds being produced thereby are harvested.

16. The method according to claim 15, wherein the fusion protein is tissue-specifically expressed.

17. The method of claim 16, wherein the fusion protein is specifically expressed in tissue selected from the group consisting of root tissue, embryo tissue, endosperm tissue, and aleurone tissue.

18. Seeds produced by the method of claim 12, wherein said seeds comprise said polynucleotide.

19. A method for making plants with increased root mass, root length and/or root branching comprising culturing the transgenic plant, parts, cells, seeds or propagating material thereof according to any one of claims 5-7 under culturing conditions.

20. An isolated cell comprising the vector of claim 2.

21. An isolated cell comprising the vector of claim 3.

22. A transgenic plant comprising the vector of claim 2.

23. A transgenic plant comprising the cell of claim 4.

24. A method for enhancing the root mass, the root length and/or the root branching of a plant, comprising:
   culturing the transgenic plant, parts, cells, or seeds thereof or propagating material according to any one of claims 5-7 under culturing conditions; and
   growing the plant.

25. A method for enhancing the root mass, the root length and/or the root branching of a plant, comprising the steps of:
   (a) introducing by genetic engineering into the plant the vector according to claim 3;
   (b) expressing the polynucleotide within said vector; and
   (c) growing the plant.

26. The polynucleotide of claim 1, wherein the transcriptional repressor domain is an EAR motif, wherein the EAR motif comprises the sequence DLELRL of SEQ ID NO: 51.

27. The polynucleotide of claim 1, wherein the transcriptional repressor domain is an EAR motif, wherein the EAR motif comprises the sequence LDLDLELRLGFA of SEQ ID NO: 52.

28. The polynucleotide of claim 1, wherein the DNA binding factor comprises the DNA binding domain of a B-type ARR, wherein said DNA binding domain is selected from the group consisting of ARR1 according to SEQ ID NO: 1, ARR2 according to SEQ ID NO: 2, ARR10 according to SEQ ID NO: 3, ARR11 according to SEQ ID NO: 4, ARR12 according to SEQ ID NO: 5, ARR13 according to SEQ ID NO: 6, ARR14 according to SEQ ID NO: 7, and ARR18 according to SEQ ID NO:8.

* * * * *

SEQUENCE LISTING

```
<160> NUMBER OF SEQ ID NOS: 70

<210> SEQ ID NO 1
<211> LENGTH: 51
<212> TYPE: PRT
<213> ORGANISM: Arabidopsis thaliana

<400> SEQUENCE: 1

Arg Val Val Trp Ser Val Glu Leu His Gln Gln Phe Val Ala Ala Val
1               5                   10                  15

Asn Gln Leu Gly Val Glu Lys Ala Val Pro Lys Lys Ile Leu Glu Leu
            20                  25                  30

Met Asn Val Pro Gly Leu Thr Arg Glu Asn Val Ala Ser His Leu Gln
        35                  40                  45

Lys Tyr Arg
    50

<210> SEQ ID NO 2
<211> LENGTH: 51
<212> TYPE: PRT
```

<213> ORGANISM: Arabidopsis thaliana

<400> SEQUENCE: 2

```
Arg Val Val Trp Ser Val Glu Leu His Gln Gln Phe Val Ala Ala Val
1               5                   10                  15

Asn Gln Leu Gly Val Asp Lys Ala Val Pro Lys Lys Ile Leu Glu Met
            20                  25                  30

Met Asn Val Pro Gly Leu Thr Arg Glu Asn Val Ala Ser His Leu Gln
        35                  40                  45

Lys Tyr Arg
    50
```

<210> SEQ ID NO 3
<211> LENGTH: 51
<212> TYPE: PRT
<213> ORGANISM: Arabidopsis thaliana

<400> SEQUENCE: 3

```
Arg Val Leu Trp Thr His Glu Leu His Asn Lys Phe Leu Ala Ala Val
1               5                   10                  15

Asp His Leu Gly Val Glu Arg Ala Val Pro Lys Lys Ile Leu Asp Leu
            20                  25                  30

Met Asn Val Asp Lys Leu Thr Arg Glu Asn Val Ala Ser His Leu Gln
        35                  40                  45

Lys Phe Arg
    50
```

<210> SEQ ID NO 4
<211> LENGTH: 52
<212> TYPE: PRT
<213> ORGANISM: Arabidopsis thaliana

<400> SEQUENCE: 4

```
Arg Val Val Trp Ser Phe Glu Leu His His Lys Phe Val Asn Ala Val
1               5                   10                  15

Asn Gln Ile Gly Cys Asp His Lys Ala Gly Pro Lys Lys Ile Leu Asp
            20                  25                  30

Leu Met Asn Val Pro Trp Leu Thr Arg Glu Asn Val Ala Ser His Leu
        35                  40                  45

Gln Lys Tyr Arg
    50
```

<210> SEQ ID NO 5
<211> LENGTH: 51
<212> TYPE: PRT
<213> ORGANISM: Arabidopsis thaliana

<400> SEQUENCE: 5

```
Arg Val Val Trp Thr Val Glu Leu His Lys Lys Phe Val Ala Ala Val
1               5                   10                  15

Asn Gln Leu Gly Tyr Glu Lys Ala Met Pro Lys Lys Ile Leu Asp Leu
            20                  25                  30

Met Asn Val Glu Lys Leu Thr Arg Glu Asn Val Ala Ser His Leu Gln
        35                  40                  45

Lys Phe Arg
    50
```

<210> SEQ ID NO 6
<211> LENGTH: 51

```
<212> TYPE: PRT
<213> ORGANISM: Arabidopsis thaliana

<400> SEQUENCE: 6

Lys Ile Trp Trp Thr Asn Pro Leu Gln Asp Leu Phe Leu Gln Ala Ile
1               5                   10                  15

Gln His Ile Gly Tyr Asp Lys Val Val Pro Lys Lys Ile Leu Ala Ile
            20                  25                  30

Met Asn Val Pro Tyr Leu Thr Arg Glu Asn Val Ala Ser His Leu Gln
        35                  40                  45

Lys Tyr Arg
    50

<210> SEQ ID NO 7
<211> LENGTH: 51
<212> TYPE: PRT
<213> ORGANISM: Arabidopsis thaliana

<400> SEQUENCE: 7

Arg Val Val Trp Ser Ile Glu Leu His Gln Gln Phe Val Asn Ala Val
1               5                   10                  15

Asn Lys Leu Gly Ile Asp Lys Ala Val Pro Lys Arg Ile Leu Glu Leu
            20                  25                  30

Met Asn Val Pro Gly Leu Ser Arg Glu Asn Val Ala Ser His Leu Gln
        35                  40                  45

Lys Phe Arg
    50

<210> SEQ ID NO 8
<211> LENGTH: 51
<212> TYPE: PRT
<213> ORGANISM: Arabidopsis thaliana

<400> SEQUENCE: 8

Arg Val Val Trp Ser Gln Glu Leu His Gln Lys Phe Val Ser Ala Val
1               5                   10                  15

Gln Gln Leu Gly Leu Asp Lys Ala Val Pro Lys Lys Ile Leu Asp Leu
            20                  25                  30

Met Ser Ile Glu Gly Leu Thr Arg Glu Asn Val Ala Ser His Leu Gln
        35                  40                  45

Lys Tyr Arg
    50

<210> SEQ ID NO 9
<211> LENGTH: 51
<212> TYPE: PRT
<213> ORGANISM: Arabidopsis thaliana

<400> SEQUENCE: 9

Arg Met Thr Trp Thr Glu Glu Leu His Gln Lys Phe Leu Glu Ala Ile
1               5                   10                  15

Glu Ile Ile Gly Ala Asn Pro Lys Val Leu Val Glu Cys Leu Gln Glu
            20                  25                  30

Met Arg Ile Glu Gly Ile Thr Arg Ser Asn Val Ala Ser His Leu Gln
        35                  40                  45

Lys His Arg
    50

<210> SEQ ID NO 10
```

```
<211> LENGTH: 56
<212> TYPE: PRT
<213> ORGANISM: Arabidopsis thaliana

<400> SEQUENCE: 10

Arg Met Gln Trp Thr Pro Glu Leu His His Lys Phe Glu Val Ala Val
1               5                   10                  15

Glu Lys Met Gly Ser Leu Glu Lys Ala Phe Pro Lys Thr Ile Leu Lys
            20                  25                  30

Tyr Met Gln Glu Glu Leu Asn Val Gln Gly Leu Thr Arg Asn Asn Val
        35                  40                  45

Ala Ser His Leu Gln Lys Tyr Arg
    50                  55

<210> SEQ ID NO 11
<211> LENGTH: 51
<212> TYPE: PRT
<213> ORGANISM: Arabidopsis thaliana

<400> SEQUENCE: 11

Lys Ile Gln Trp Thr Asp Ser Leu His Asp Leu Phe Leu Gln Ala Ile
1               5                   10                  15

Arg His Ile Gly Leu Asp Lys Ala Val Pro Lys Lys Ile Leu Ala Phe
            20                  25                  30

Met Ser Val Pro Tyr Leu Thr Arg Glu Asn Val Ala Ser His Leu Gln
        35                  40                  45

Lys Tyr Arg
    50

<210> SEQ ID NO 12
<211> LENGTH: 669
<212> TYPE: PRT
<213> ORGANISM: Arabidopsis thaliana

<400> SEQUENCE: 12

Met Met Asn Pro Ser His Gly Arg Gly Leu Gly Ser Ala Gly Gly Ser
1               5                   10                  15

Ser Ser Gly Arg Asn Gln Gly Gly Gly Gly Thr Val Val Glu Met
            20                  25                  30

Phe Pro Ser Gly Leu Arg Val Leu Val Asp Asp Pro Thr Cys
        35                  40                  45

Leu Met Ile Leu Glu Arg Met Leu Arg Thr Cys Leu Tyr Glu Val Thr
    50                  55                  60

Lys Cys Asn Arg Ala Glu Met Ala Leu Ser Leu Leu Arg Lys Asn Lys
65                  70                  75                  80

His Gly Phe Asp Ile Val Ile Ser Asp Val His Met Pro Asp Met Asp
                85                  90                  95

Gly Phe Lys Leu Leu Glu His Val Gly Leu Glu Met Asp Leu Pro Val
            100                 105                 110

Ile Met Met Ser Ala Asp Asp Ser Lys Ser Val Val Leu Lys Gly Val
        115                 120                 125

Thr His Gly Ala Val Asp Tyr Leu Ile Lys Pro Val Arg Met Glu Ala
    130                 135                 140

Leu Lys Asn Ile Trp Gln His Val Val Arg Lys Arg Ser Glu Trp
145                 150                 155                 160

Ser Val Pro Glu His Ser Gly Ser Ile Glu Glu Thr Gly Glu Arg Gln
                165                 170                 175
```

```
Gln Gln Gln His Arg Gly Gly Gly Gly Ala Ala Val Ser Gly Gly
            180                 185                 190

Glu Asp Ala Val Asp Asp Asn Ser Ser Val Asn Glu Gly Asn Asn
            195                 200                 205

Trp Arg Ser Ser Arg Lys Arg Lys Asp Glu Glu Gly Glu Glu Gln
210                 215                 220

Gly Asp Asp Lys Asp Glu Asp Ala Ser Asn Leu Lys Lys Pro Arg Val
225                 230                 235                 240

Val Trp Ser Val Glu Leu His Gln Gln Phe Val Ala Val Asn Gln
            245                 250                 255

Leu Gly Val Glu Lys Ala Val Pro Lys Lys Ile Leu Glu Leu Met Asn
            260                 265                 270

Val Pro Gly Leu Thr Arg Glu Asn Val Ala Ser His Leu Gln Lys Tyr
            275                 280                 285

Arg Ile Tyr Leu Arg Arg Leu Gly Gly Val Ser Gln His Gln Gly Asn
290                 295                 300

Leu Asn Asn Ser Phe Met Thr Gly Gln Asp Ala Ser Phe Gly Pro Leu
305                 310                 315                 320

Ser Thr Leu Asn Gly Phe Asp Leu Gln Ala Leu Ala Val Thr Gly Gln
            325                 330                 335

Leu Pro Ala Gln Ser Leu Ala Gln Leu Gln Ala Ala Gly Leu Gly Arg
            340                 345                 350

Pro Ala Met Val Ser Lys Ser Gly Leu Pro Val Ser Ser Ile Val Asp
            355                 360                 365

Glu Arg Ser Ile Phe Ser Phe Asp Asn Thr Lys Thr Arg Phe Gly Glu
370                 375                 380

Gly Leu Gly His His Gly Gln Gln Pro Gln Gln Gln Pro Gln Met Asn
385                 390                 395                 400

Leu Leu His Gly Val Pro Thr Gly Leu Gln Gln Gln Leu Pro Met Gly
            405                 410                 415

Asn Arg Met Ser Ile Gln Gln Gln Ile Ala Ala Val Arg Ala Gly Asn
            420                 425                 430

Ser Val Gln Asn Asn Gly Met Leu Met Pro Leu Ala Gly Gln Gln Ser
            435                 440                 445

Leu Pro Arg Gly Pro Pro Met Leu Thr Ser Ser Gln Ser Ser Ile
450                 455                 460

Arg Gln Pro Met Leu Ser Asn Arg Ile Ser Glu Arg Ser Gly Phe Ser
465                 470                 475                 480

Gly Arg Asn Asn Ile Pro Glu Ser Ser Arg Val Leu Pro Thr Ser Tyr
            485                 490                 495

Thr Asn Leu Thr Thr Gln His Ser Ser Ser Ser Met Pro Tyr Asn Asn
            500                 505                 510

Phe Gln Pro Glu Leu Pro Val Asn Ser Phe Pro Leu Ala Ser Ala Pro
            515                 520                 525

Gly Ile Ser Val Pro Val Arg Lys Ala Thr Ser Tyr Gln Glu Glu Val
            530                 535                 540

Asn Ser Ser Glu Ala Gly Phe Thr Thr Pro Ser Tyr Asp Met Phe Thr
545                 550                 555                 560

Thr Arg Gln Asn Asp Trp Asp Leu Arg Asn Ile Gly Ile Ala Phe Asp
            565                 570                 575

Ser His Gln Asp Ser Glu Ser Ala Ala Phe Ser Ala Ser Glu Ala Tyr
            580                 585                 590

Ser Ser Ser Ser Met Ser Arg His Asn Thr Thr Val Ala Ala Thr Glu
```

```
                595                 600                 605
His Gly Arg Asn His Gln Gln Pro Pro Ser Gly Met Val Gln His His
    610                 615                 620

Gln Val Tyr Ala Asp Gly Asn Gly Gly Ser Val Arg Val Lys Ser Glu
625                 630                 635                 640

Arg Val Ala Thr Asp Thr Ala Thr Met Ala Phe His Glu Gln Tyr Ser
                645                 650                 655

Asn Gln Glu Asp Leu Met Ser Ala Leu Leu Lys Gln Val
                660                 665

<210> SEQ ID NO 13
<211> LENGTH: 664
<212> TYPE: PRT
<213> ORGANISM: Arabidopsis thaliana

<400> SEQUENCE: 13

Met Val Asn Pro Gly His Gly Arg Gly Pro Asp Ser Gly Thr Ala Ala
1               5                   10                  15

Gly Gly Ser Asn Ser Asp Pro Phe Pro Ala Asn Leu Arg Val Leu Val
                20                  25                  30

Val Asp Asp Asp Pro Thr Cys Leu Met Ile Leu Glu Arg Met Leu Met
            35                  40                  45

Thr Cys Leu Tyr Arg Val Thr Lys Cys Asn Arg Ala Glu Ser Ala Leu
    50                  55                  60

Ser Leu Leu Arg Lys Asn Lys Asn Gly Phe Asp Ile Val Ile Ser Asp
65                  70                  75                  80

Val His Met Pro Asp Met Asp Gly Phe Lys Leu Leu Glu His Val Gly
                85                  90                  95

Leu Glu Met Asp Leu Pro Val Ile Met Met Ser Ala Asp Asp Ser Lys
                100                 105                 110

Ser Val Val Leu Lys Gly Val Thr His Gly Ala Val Asp Tyr Leu Ile
            115                 120                 125

Lys Pro Val Arg Ile Glu Ala Leu Lys Asn Ile Trp Gln His Val Val
    130                 135                 140

Arg Lys Lys Arg Asn Glu Trp Asn Val Ser Glu His Ser Gly Gly Ser
145                 150                 155                 160

Ile Glu Asp Thr Gly Gly Asp Arg Asp Arg Gln Gln Gln His Arg Glu
                165                 170                 175

Asp Ala Asp Asn Asn Ser Ser Ser Val Asn Glu Gly Asn Gly Arg Ser
            180                 185                 190

Ser Arg Lys Arg Lys Glu Glu Glu Val Asp Asp Gln Gly Asp Asp Lys
    195                 200                 205

Glu Asp Ser Ser Ser Leu Lys Lys Pro Arg Val Val Trp Ser Val Glu
210                 215                 220

Leu His Gln Gln Phe Val Ala Ala Val Asn Gln Leu Gly Val Asp Lys
225                 230                 235                 240

Ala Val Pro Lys Lys Ile Leu Glu Met Met Asn Val Pro Gly Leu Thr
                245                 250                 255

Arg Glu Asn Val Ala Ser His Leu Gln Lys Tyr Arg Ile Tyr Leu Arg
            260                 265                 270

Arg Leu Gly Gly Val Ser Gln His Gln Gly Asn Met Asn His Ser Phe
    275                 280                 285

Met Thr Gly Gln Asp Gln Ser Phe Gly Pro Leu Ser Ser Leu Asn Gly
            290                 295                 300
```

```
Phe Asp Leu Gln Ser Leu Ala Val Thr Gly Gln Leu Pro Pro Gln Ser
305                 310                 315                 320

Leu Ala Gln Leu Gln Ala Ala Gly Leu Gly Arg Pro Thr Leu Ala Lys
            325                 330                 335

Pro Gly Met Ser Val Ser Pro Leu Val Asp Gln Arg Ser Ile Phe Asn
            340                 345                 350

Phe Glu Asn Pro Lys Ile Arg Phe Gly Asp Gly His Gly Gln Thr Met
            355                 360                 365

Asn Asn Gly Asn Leu Leu His Gly Val Pro Thr Gly Ser His Met Arg
            370                 375                 380

Leu Arg Pro Gly Gln Asn Val Gln Ser Ser Gly Met Met Leu Pro Val
385                 390                 395                 400

Ala Asp Gln Leu Pro Arg Gly Gly Pro Ser Met Leu Pro Ser Leu Gly
            405                 410                 415

Gln Gln Pro Ile Leu Ser Ser Ser Val Ser Arg Arg Ser Asp Leu Thr
            420                 425                 430

Gly Ala Leu Ala Val Arg Asn Ser Ile Pro Glu Thr Asn Ser Arg Val
            435                 440                 445

Leu Pro Thr Thr His Ser Val Phe Asn Asn Phe Pro Ala Asp Leu Pro
450                 455                 460

Arg Ser Ser Phe Pro Leu Ala Ser Ala Pro Gly Ile Ser Val Pro Val
465                 470                 475                 480

Ser Val Ser Tyr Gln Glu Glu Val Asn Ser Asp Ala Lys Gly Gly
            485                 490                 495

Ser Ser Ala Ala Thr Ala Gly Phe Gly Asn Pro Ser Tyr Asp Ile Phe
            500                 505                 510

Asn Asp Phe Pro Gln His Gln Gln His Asn Lys Asn Ile Ser Asn Lys
            515                 520                 525

Leu Asn Asp Trp Asp Leu Arg Asn Met Gly Leu Val Phe Ser Ser Asn
530                 535                 540

Gln Asp Ala Ala Thr Ala Thr Ala Thr Ala Ala Phe Ser Thr Ser Glu
545                 550                 555                 560

Ala Tyr Ser Ser Ser Thr Gln Arg Lys Arg Arg Glu Thr Asp Ala
            565                 570                 575

Thr Val Val Gly Glu His Gly Gln Asn Leu Gln Ser Pro Ser Arg Asn
            580                 585                 590

Leu Tyr His Leu Asn His Val Phe Met Asp Gly Gly Ser Val Arg Val
            595                 600                 605

Lys Ser Glu Arg Val Ala Glu Thr Val Thr Cys Pro Pro Ala Asn Thr
610                 615                 620

Leu Phe His Glu Gln Tyr Asn Gln Glu Asp Leu Met Ser Ala Phe Leu
625                 630                 635                 640

Lys Gln Glu Gly Ile Pro Ser Val Asp Asn Glu Phe Glu Phe Asp Gly
            645                 650                 655

Tyr Ser Ile Asp Asn Ile Gln Val
            660

<210> SEQ ID NO 14
<211> LENGTH: 552
<212> TYPE: PRT
<213> ORGANISM: Arabidopsis thaliana

<400> SEQUENCE: 14

Met Thr Met Glu Gln Glu Ile Glu Val Leu Asp Gln Phe Pro Val Gly
1               5                   10                  15
```

```
Met Arg Val Leu Ala Val Asp Asp Gln Thr Cys Leu Arg Ile Leu
         20                  25                  30

Gln Thr Leu Leu Gln Arg Cys Gln Tyr His Val Thr Thr Asn Gln
         35                  40                  45

Ala Gln Thr Ala Leu Glu Leu Leu Arg Glu Asn Lys Asn Lys Phe Asp
50                   55                  60

Leu Val Ile Ser Asp Val Asp Met Pro Asp Met Asp Gly Phe Lys Leu
65                   70                  75                  80

Leu Glu Leu Val Gly Leu Glu Met Asp Leu Pro Val Ile Met Leu Ser
                 85                  90                  95

Ala His Ser Asp Pro Lys Tyr Val Met Lys Gly Val Lys His Gly Ala
             100                 105                 110

Cys Asp Tyr Leu Leu Lys Pro Val Arg Ile Glu Glu Leu Lys Asn Ile
             115                 120                 125

Trp Gln His Val Val Arg Lys Ser Lys Leu Lys Lys Asn Lys Ser Asn
         130                 135                 140

Val Ser Asn Gly Ser Gly Asn Cys Asp Lys Ala Asn Arg Lys Arg Lys
145                 150                 155                 160

Glu Gln Tyr Glu Glu Glu Glu Glu Glu Arg Gly Asn Asp Asn Asp
                 165                 170                 175

Asp Pro Thr Ala Gln Lys Lys Pro Arg Val Leu Trp Thr His Glu Leu
             180                 185                 190

His Asn Lys Phe Leu Ala Ala Val Asp His Leu Gly Val Glu Arg Ala
         195                 200                 205

Val Pro Lys Lys Ile Leu Asp Leu Met Asn Val Asp Lys Leu Thr Arg
         210                 215                 220

Glu Asn Val Ala Ser His Leu Gln Lys Phe Arg Val Ala Leu Lys Lys
225                 230                 235                 240

Val Ser Asp Asp Ala Ile Gln Gln Ala Asn Arg Ala Ala Ile Asp Ser
             245                 250                 255

His Phe Met Gln Met Asn Ser Gln Lys Gly Leu Gly Gly Phe Tyr His
             260                 265                 270

His His Arg Gly Ile Pro Val Gly Ser Gly Gln Phe His Gly Gly Thr
         275                 280                 285

Thr Met Met Arg His Tyr Ser Ser Asn Arg Asn Leu Gly Arg Leu Asn
         290                 295                 300

Ser Leu Gly Ala Gly Met Phe Gln Pro Val Ser Ser Phe Pro Arg
305                 310                 315                 320

Asn His Asn Asp Gly Gly Asn Ile Leu Gln Gly Leu Pro Leu Glu Glu
             325                 330                 335

Leu Gln Ile Asn Asn Asn Ile Asn Arg Ala Phe Pro Ser Phe Thr Ser
             340                 345                 350

Gln Gln Asn Ser Pro Met Val Ala Pro Ser Asn Leu Leu Leu Leu Glu
             355                 360                 365

Gly Asn Pro Gln Ser Ser Ser Leu Pro Ser Asn Pro Gly Phe Ser Pro
370                 375                 380

His Phe Glu Ile Ser Lys Arg Leu Glu His Trp Ser Asn Ala Ala Leu
385                 390                 395                 400

Ser Thr Asn Ile Pro Gln Ser Asp Val His Ser Lys Pro Asp Thr Leu
             405                 410                 415

Glu Trp Asn Ala Phe Cys Asp Ser Ala Ser Pro Leu Val Asn Pro Asn
             420                 425                 430
```

```
Leu Asp Thr Asn Pro Ala Ser Leu Cys Arg Asn Thr Gly Phe Gly Ser
            435                 440                 445

Thr Asn Ala Ala Gln Thr Asp Phe Phe Tyr Pro Leu Gln Met Asn Gln
        450                 455                 460

Gln Pro Ala Asn Asn Ser Gly Pro Val Thr Glu Ala Gln Leu Phe Arg
465                 470                 475                 480

Ser Ser Asn Pro Asn Glu Gly Leu Leu Met Gly Gln Gln Lys Leu Gln
                485                 490                 495

Ser Gly Leu Met Ala Ser Asp Ala Gly Ser Leu Asp Asp Ile Val Asn
            500                 505                 510

Ser Leu Met Thr Gln Glu Gln Ser Gln Ser Asp Phe Ser Glu Gly Asp
        515                 520                 525

Trp Asp Leu Asp Gly Leu Ala His Ser Glu His Ala Tyr Glu Lys Leu
530                 535                 540

His Phe Pro Phe Ser Leu Ser Ala
545                 550

<210> SEQ ID NO 15
<211> LENGTH: 521
<212> TYPE: PRT
<213> ORGANISM: Arabidopsis thaliana

<400> SEQUENCE: 15

Met Glu Lys Ser Gly Phe Ser Pro Val Gly Leu Arg Val Leu Val Val
1               5                   10                  15

Asp Asp Asp Pro Thr Trp Leu Lys Ile Leu Glu Lys Met Leu Lys Lys
            20                  25                  30

Cys Ser Tyr Glu Val Thr Thr Cys Gly Leu Ala Arg Glu Ala Leu Arg
        35                  40                  45

Leu Leu Arg Glu Arg Lys Asp Gly Tyr Asp Ile Val Ile Ser Asp Val
    50                  55                  60

Asn Met Pro Asp Met Asp Gly Phe Lys Leu Leu Glu His Val Gly Leu
65                  70                  75                  80

Glu Leu Asp Leu Pro Val Ile Met Met Ser Val Asp Gly Glu Thr Ser
                85                  90                  95

Arg Val Met Lys Gly Val Gln His Gly Ala Cys Asp Tyr Leu Leu Lys
            100                 105                 110

Pro Ile Arg Met Lys Glu Leu Lys Ile Ile Trp Gln His Val Leu Arg
        115                 120                 125

Lys Lys Leu Gln Glu Val Arg Asp Ile Glu Gly Cys Gly Tyr Glu Gly
    130                 135                 140

Gly Ala Asp Trp Ile Thr Arg Tyr Asp Glu Ala His Phe Leu Gly Gly
145                 150                 155                 160

Gly Glu Asp Val Ser Phe Gly Lys Lys Arg Lys Asp Phe Asp Phe Glu
                165                 170                 175

Lys Lys Leu Leu Gln Asp Glu Ser Asp Pro Ser Ser Ser Ser Ser Lys
            180                 185                 190

Lys Ala Arg Val Val Trp Ser Phe Glu Leu His His Lys Phe Val Asn
        195                 200                 205

Ala Val Asn Gln Ile Gly Cys Asp His Lys Ala Gly Pro Lys Lys Ile
    210                 215                 220

Leu Asp Leu Met Asn Val Pro Trp Leu Thr Arg Glu Asn Val Ala Ser
225                 230                 235                 240

His Leu Gln Lys Tyr Arg Leu Tyr Leu Ser Arg Leu Glu Lys Gly Lys
                245                 250                 255
```

```
Glu Leu Lys Cys Tyr Ser Gly Val Lys Asn Ala Asp Ser Ser Pro
            260                 265                 270

Lys Asp Val Glu Val Asn Ser Gly Tyr Gln Ser Pro Gly Arg Ser Ser
        275                 280                 285

Tyr Val Phe Ser Gly Gly Asn Ser Leu Ile Gln Lys Ala Thr Glu Ile
    290                 295                 300

Asp Pro Lys Pro Leu Ala Ser Ala Ser Leu Ser Asp Leu Asn Thr Asp
305                 310                 315                 320

Val Ile Met Pro Pro Lys Thr Lys Thr Arg Ile Gly Phe Asp Pro
            325                 330                 335

Pro Ile Ser Ser Ser Ala Phe Asp Ser Leu Leu Pro Trp Asn Asp Val
            340                 345                 350

Pro Glu Val Leu Glu Ser Lys Pro Val Leu Tyr Glu Asn Ser Phe Leu
        355                 360                 365

Gln Gln Gln Pro Leu Pro Ser Gln Ser Ser Tyr Val Ala Asn Ser Ala
    370                 375                 380

Pro Ser Leu Met Glu Glu Met Lys Pro Pro Tyr Glu Thr Pro Ala
385                 390                 395                 400

Gly Gly Ser Ser Val Asn Ala Asp Glu Phe Leu Met Pro Gln Asp Lys
            405                 410                 415

Ile Pro Thr Val Thr Leu Gln Asp Leu Asp Pro Ser Ala Met Lys Leu
            420                 425                 430

Gln Glu Phe Asn Thr Glu Ala Ile Leu Arg Ser Leu Asn Trp Glu Leu
        435                 440                 445

Pro Glu Ser His His Ser Val Ser Leu Asp Thr Asp Leu Asp Leu Thr
    450                 455                 460

Trp Leu Gln Gly Glu Arg Phe Leu Ala Asn Thr Gly Leu Gln Phe Gln
465                 470                 475                 480

Asp Tyr Ser Ser Pro Ser Leu Leu Ser Glu Leu Pro Ala His Leu
            485                 490                 495

Asn Trp Tyr Gly Asn Glu Arg Leu Pro Asp Pro Asp Glu Tyr Ser Phe
        500                 505                 510

Met Val Asp Gln Gly Leu Phe Ile Ser
            515                 520
```

<210> SEQ ID NO 16
<211> LENGTH: 596
<212> TYPE: PRT
<213> ORGANISM: Arabidopsis thaliana

<400> SEQUENCE: 16

```
Met Thr Val Glu Gln Asn Leu Glu Ala Leu Asp Gln Phe Pro Val Gly
1               5                   10                  15

Met Arg Val Leu Ala Val Asp Asp Gln Thr Cys Leu Lys Ile Leu
            20                  25                  30

Glu Ser Leu Leu Arg His Cys Gln Tyr His Val Thr Thr Thr Asn Gln
        35                  40                  45

Ala Gln Lys Ala Leu Glu Leu Leu Arg Glu Asn Lys Asn Lys Phe Asp
    50                  55                  60

Leu Val Ile Ser Asp Val Asp Met Pro Asp Met Asp Gly Phe Lys Leu
65                  70                  75                  80

Leu Glu Leu Val Gly Leu Glu Met Asp Leu Pro Val Ile Met Leu Ser
            85                  90                  95

Ala His Ser Asp Pro Lys Tyr Val Met Lys Gly Val Thr His Gly Ala
```

```
                100             105              110
        Cys Asp Tyr Leu Leu Lys Pro Val Arg Ile Glu Glu Leu Lys Asn Ile
                    115             120             125

Trp Gln His Val Val Arg Ser Arg Phe Asp Lys Asn Arg Gly Ser Asn
            130             135             140

Asn Asn Gly Asp Lys Arg Asp Gly Ser Gly Asn Glu Val Gly Asn
        145             150             155                     160

Ser Asp Pro Asn Asn Gly Lys Gly Asn Arg Lys Arg Lys Asp Gln Tyr
                        165             170             175

Asn Glu Asp Glu Asp Glu Asp Arg Asp Asp Asn Asp Asp Ser Cys Ala
                    180             185             190

Gln Lys Lys Gln Arg Val Val Trp Thr Val Glu Leu His Lys Lys Phe
                195             200             205

Val Ala Ala Val Asn Gln Leu Gly Tyr Glu Lys Ala Met Pro Lys Lys
                210             215             220

Ile Leu Asp Leu Met Asn Val Glu Lys Leu Thr Arg Glu Asn Val Ala
        225             230             235             240

Ser His Leu Gln Lys Phe Arg Leu Tyr Leu Lys Arg Ile Ser Gly Val
                        245             250             255

Ala Asn Gln Gln Ala Ile Met Ala Asn Ser Glu Leu His Phe Met Gln
                    260             265             270

Met Asn Gly Leu Asp Gly Phe His His Arg Pro Ile Pro Val Gly Ser
                275             280             285

Gly Gln Tyr His Gly Gly Ala Pro Ala Met Arg Ser Phe Pro Pro Asn
            290             295             300

Gly Ile Leu Gly Arg Leu Asn Ser Ser Ser Gly Ile Gly Val Arg Ser
        305             310             315             320

Leu Ser Ser Pro Pro Ala Gly Met Phe Leu Gln Asn Gln Thr Asp Ile
                        325             330             335

Gly Lys Phe His His Val Ser Ser Leu Pro Leu Asn His Ser Asp Gly
                    340             345             350

Gly Asn Ile Leu Gln Gly Leu Pro Met Pro Leu Glu Phe Asp Gln Leu
                355             360             365

Gln Thr Asn Asn Asn Lys Ser Arg Asn Met Asn Ser Asn Lys Ser Ile
            370             375             380

Ala Gly Thr Ser Met Ala Phe Pro Ser Phe Ser Thr Gln Gln Asn Ser
        385             390             395             400

Leu Ile Ser Ala Pro Asn Asn Val Val Leu Glu Gly His Pro
                        405             410             415

Gln Ala Thr Pro Pro Gly Phe Pro Gly His Gln Ile Asn Lys Arg Leu
                    420             425             430

Glu His Trp Ser Asn Ala Val Ser Ser Thr His Pro Pro Pro
                435             440             445

Ala His Asn Ser Asn Ser Ile Asn His Gln Phe Asp Val Ser Pro Leu
        450             455             460

Pro His Ser Arg Pro Asp Pro Leu Glu Trp Asn Asn Val Ser Ser
        465             470             475             480

Tyr Ser Ile Pro Phe Cys Asp Ser Ala Asn Thr Leu Ser Pro Ala
                        485             490             495

Leu Asp Thr Thr Asn Pro Arg Ala Phe Cys Arg Asn Thr Asp Phe Asp
                    500             505             510

Ser Asn Thr Asn Val Gln Pro Gly Val Phe Tyr Gly Pro Ser Thr Asp
                515             520             525
```

```
Ala Met Ala Leu Leu Ser Ser Asn Pro Lys Glu Gly Phe Val Val
        530                 535                 540

Gly Gln Gln Lys Leu Gln Ser Gly Gly Phe Met Val Ala Asp Ala Gly
545                 550                 555                 560

Ser Leu Asp Asp Ile Val Asn Ser Thr Met Lys Gln Glu Gln Ser Gln
                565                 570                 575

Gly Asp Leu Ser Gly Gly Asp Leu Gly Tyr Gly Gly Phe Ser Ser Leu
                580                 585                 590

Arg Thr Cys Ile
            595

<210> SEQ ID NO 17
<211> LENGTH: 575
<212> TYPE: PRT
<213> ORGANISM: Arabidopsis thaliana

<400> SEQUENCE: 17

Met Ala Phe Ala Gln Ser Val Tyr Asn Gln Ser Val Leu Lys Ile
1               5                   10                  15

Asn Val Met Val Val Asp Asp Asn Arg Val Phe Leu Asp Ile Trp Ser
                20                  25                  30

Arg Met Leu Glu Lys Ser Lys Tyr Arg Glu Ile Thr Val Ile Ala Val
            35                  40                  45

Asp Tyr Pro Lys Lys Ala Leu Ser Thr Leu Lys Asn Gln Arg Asp Asn
        50                  55                  60

Ile Asp Leu Ile Ile Thr Asp Tyr Tyr Met Pro Gly Met Asn Gly Leu
65                  70                  75                  80

Gln Leu Lys Lys Gln Ile Thr Gln Glu Phe Gly Asn Leu Ser Val Leu
                85                  90                  95

Val Met Ser Ser Asp Pro Asn Lys Glu Glu Glu Ser Leu Ser Cys Gly
                100                 105                 110

Ala Met Gly Phe Ile Pro Lys Pro Ile Ala Pro Thr Asp Leu Pro Lys
            115                 120                 125

Ile Tyr Gln Phe Ala Leu Thr Tyr Lys Arg Asn Gly Lys Ser Thr Leu
        130                 135                 140

Ser Thr Glu Gln Asn Gln Lys Asp Ala Asn Val Ser Val Pro Gln Gln
145                 150                 155                 160

Ile Met Leu Val Pro Glu Gln Ala Tyr Val Leu Lys Thr Lys Lys Lys
                165                 170                 175

Asn Cys Ser Ser Lys Ser Asp Thr Arg Thr Val Asn Ser Thr Asn Val
                180                 185                 190

Ser His Val Ser Thr Asn Gly Ser Arg Lys Asn Arg Lys Arg Lys Pro
            195                 200                 205

Lys Gly Gly Pro Ser Asp Asp Gly Glu Ser Leu Ser Gln Pro Pro Lys
        210                 215                 220

Lys Lys Lys Ile Trp Trp Thr Asn Pro Leu Gln Asp Leu Phe Leu Gln
225                 230                 235                 240

Ala Ile Gln His Ile Gly Tyr Asp Lys Val Val Pro Lys Lys Ile Leu
                245                 250                 255

Ala Ile Met Asn Val Pro Tyr Leu Thr Arg Glu Asn Val Ala Ser His
                260                 265                 270

Leu Gln Lys Tyr Arg Leu Phe Val Lys Arg Val His Gln Gly Arg
            275                 280                 285

Phe Ser Met Leu Ser Asp Arg Gly Lys Asp Ser Met Phe Arg Gln Thr
```

```
                290                 295                 300
His Ile Lys Glu Pro Tyr Val Asn Tyr Tyr Thr Pro Ser Thr Ser Trp
305                 310                 315                 320

Tyr Glu Thr Ser Leu Asn Asn Arg Ser Phe Tyr Ser Glu Ser Val His
                325                 330                 335

Gly His Ser Arg Leu Leu Ser Glu Ala Arg Glu Pro Val Arg Tyr Asn
                340                 345                 350

Gln Met Ser Tyr Asn Tyr Met Asn Arg Asn Ile Ser Phe Glu Asn Gln
                355                 360                 365

Pro Ser Gln Asn Glu Glu Thr Arg Thr Val Phe Glu Pro Pro Val Met
370                 375                 380

Ala Asn Lys Ile Ser Gln Thr Ser Gln Val Leu Gly Phe Gly Gln Leu
385                 390                 395                 400

Gly Pro Ser Ala Ile Ser Gly His Asn Phe Asn Thr Asn Met Met Ser
                405                 410                 415

Ser Tyr Gly Ser Leu Thr Pro Asn Gln Pro Gly Thr Ser His Phe Ser
                420                 425                 430

Tyr Gly Met Gln Ser Val Leu Asn Asn Glu Asn Ala Thr Tyr Asn Pro
                435                 440                 445

Gln Pro Pro Ala Asn Ala Thr Thr Gln Pro Asn Leu Asp Glu Leu Pro
                450                 455                 460

Gln Leu Glu Asn Leu Asn Leu Tyr Asn Asp Leu Gly Asn Thr Ser Glu
465                 470                 475                 480

Leu Pro Tyr Asn Ile Ser Asn Phe Gln Ser Asp Asp Asn Lys Lys Gln
                485                 490                 495

Gly Glu Glu Asp Gly Asp Trp Thr Phe Val Asn Ile Asn Gln Asp Gln
                500                 505                 510

Ser Asn Gly Glu Ser Ser Asn Thr Ile Ala Thr Pro Glu Thr Asn Thr
                515                 520                 525

Pro Asn Phe Asn Ile Asn Pro Asn Gln Asn Gly Gln Ala Val Pro
                530                 535                 540

Glu Phe Thr Asp Trp Ser Phe Leu Asp Gln Gln Pro Arg Arg Leu Gly
545                 550                 555                 560

Ile Arg Ile Gly Tyr Phe Gly Phe Lys Phe Ser Gly Leu Glu Val
                565                 570                 575

<210> SEQ ID NO 18
<211> LENGTH: 382
<212> TYPE: PRT
<213> ORGANISM: Arabidopsis thaliana

<400> SEQUENCE: 18

Met Pro Ile Asn Asp Gln Phe Pro Ser Gly Leu Arg Ile Leu Val Val
1               5                   10                  15

Asp Asp Asp Thr Ser Cys Leu Phe Ile Leu Glu Lys Met Leu Leu Arg
                20                  25                  30

Leu Met Tyr Gln Val Thr Ile Cys Ser Gln Ala Asp Val Ala Leu Thr
                35                  40                  45

Ile Leu Arg Glu Arg Lys Asp Ser Phe Asp Leu Val Leu Ser Asp Val
                50                  55                  60

His Met Pro Gly Met Asn Gly Tyr Asn Leu Leu Gln Gln Val Gly Leu
65                  70                  75                  80

Leu Glu Met Asp Leu Pro Val Ile Met Met Ser Val Asp Gly Arg Thr
                85                  90                  95
```

-continued

```
Thr Thr Val Met Thr Gly Ile Asn His Gly Ala Cys Asp Tyr Leu Ile
            100                 105                 110

Lys Pro Ile Arg Pro Glu Glu Leu Lys Asn Ile Trp Gln His Val Val
        115                 120                 125

Arg Arg Lys Cys Val Met Lys Lys Glu Leu Arg Ser Ser Gln Ala Leu
    130                 135                 140

Glu Asp Asn Lys Asn Ser Gly Ser Leu Glu Thr Val Val Ser Val
145                 150                 155                 160

Ser Glu Cys Ser Glu Glu Ser Leu Met Lys Cys Arg Asn Lys Lys Lys
                165                 170                 175

Lys Lys Lys Arg Ser Val Asp Arg Asp Asp Asn Glu Asp Asp Leu Leu
            180                 185                 190

Leu Asp Pro Gly Asn Ser Lys Lys Ser Arg Val Val Trp Ser Ile Glu
        195                 200                 205

Leu His Gln Gln Phe Val Asn Ala Val Asn Lys Leu Gly Ile Asp Lys
    210                 215                 220

Ala Val Pro Lys Arg Ile Leu Glu Leu Met Asn Val Pro Gly Leu Ser
225                 230                 235                 240

Arg Glu Asn Val Ala Ser His Leu Gln Lys Phe Arg Leu Tyr Leu Lys
                245                 250                 255

Arg Leu Ser Gly Glu Ala Ser Gln Ser Asn Asp Ser Glu Ser Thr Lys
            260                 265                 270

Arg Tyr Glu Asn Ile Gln Ala Leu Val Ser Ser Gly Gln Leu His Pro
        275                 280                 285

Gln Thr Leu Ala Ala Leu Phe Gly Gln Pro Ile Asp Asn His His Ser
    290                 295                 300

Ala Ser Phe Gly Val Trp Ile Pro Asn Asp Asn Leu Gly Arg Ser Gln
305                 310                 315                 320

Asn Glu His Phe Ser Val Asp Val Ser Ser Ala Ser Asn Arg Pro Val
                325                 330                 335

Ser Val Ala Val His Gly Leu Ser Ser Ser Ala Asn Phe Arg Gln Arg
            340                 345                 350

Gly Asp Val Asn Asn Asn Arg Ile Arg Gln Gly Tyr Gly Ser Asn Val
        355                 360                 365

Asn Glu Glu Ser Trp Ile Leu Glu Arg Ser Ser Arg Gln Arg
    370                 375                 380
```

<210> SEQ ID NO 19
<211> LENGTH: 581
<212> TYPE: PRT
<213> ORGANISM: Arabidopsis thaliana

<400> SEQUENCE: 19

```
Met Val Leu Ser Cys Leu Lys Leu Val Leu Lys Trp Thr Phe Leu Ser
1               5                   10                  15

Ser Val Arg Leu Leu Pro Leu Phe Phe Ile Ser Thr Leu Ala Leu Ile
            20                  25                  30

Val Thr Cys Phe Ile Val Ser Val Leu Ser Ala His Ser Asp Tyr Asp
        35                  40                  45

Ser Val Met Lys Gly Ile Ile His Gly Ala Cys Asp Tyr Leu Val Lys
    50                  55                  60

Pro Val Gly Leu Lys Glu Leu Gln Asn Ile Trp His His Val Val Lys
65                  70                  75                  80

Lys Asn Ile Lys Ser Tyr Ala Lys Leu Leu Pro Pro Ser Glu Ser Asp
                85                  90                  95
```

```
Ser Val Pro Ser Ala Ser Arg Lys Arg Lys Asp Lys Val Asn Asp Ser
            100                 105                 110
Gly Asp Glu Asp Asp Ser Asp Arg Glu Glu Asp Asp Gly Glu Gly Ser
        115                 120                 125
Glu Gln Asp Gly Asp Gly Ser Gly Thr Arg Lys Lys Pro Arg Val Val
    130                 135                 140
Trp Ser Gln Glu Leu His Gln Lys Phe Val Ser Ala Val Gln Leu
145                 150                 155                 160
Gly Leu Asp Lys Ala Val Pro Lys Lys Ile Leu Asp Leu Met Ser Ile
                165                 170                 175
Glu Gly Leu Thr Arg Glu Asn Val Ala Ser His Leu Gln Lys Tyr Arg
            180                 185                 190
Leu Tyr Leu Lys Lys Ile Asp Glu Gly Gln Gln Gln Asn Met Thr Pro
        195                 200                 205
Asp Ala Phe Gly Thr Arg Asp Ser Ser Tyr Phe Gln Met Ala Gln Leu
    210                 215                 220
Asp Gly Leu Arg Asp Phe Thr Ala Ala Arg Gln Ile Pro Ser Ser Gly
225                 230                 235                 240
Leu Leu Ser Arg Ser His Leu Thr Lys Leu Gln Pro Pro Met Tyr Ser
                245                 250                 255
Ser Ile Asn Leu Gln Gly Met Asn Ser Ser Ser Phe Ile Gln Gln Gly
            260                 265                 270
His His Gln Asn Ser Ser Asn Ser Ala Asn Pro Phe Gly Thr Tyr His
        275                 280                 285
Ser Thr Leu Ser Pro Arg Ile Gln Asn Val Asn Leu Phe Gln Arg Thr
    290                 295                 300
Ser Ser Pro Leu Glu Pro Leu Gln Phe Pro Arg Ser Lys Ser Tyr Ile
305                 310                 315                 320
Gly Asp Phe Lys Gly Leu Gly Asp Arg Ala Ile Gly Gly Ser Phe Leu
                325                 330                 335
Asp Thr Cys Met Pro Phe Gly Ser Ser Thr Ser Leu Pro Ser Ala
        340                 345                 350
Ser Thr Asn Pro Leu Met Leu Gln Ala Asn Tyr Thr Gln Pro Leu His
    355                 360                 365
Ile Ala Ser Asp Gly Ile Gln Pro Cys Ile Glu Gly Thr Pro Ser Asn
370                 375                 380
Ser Ala Ser Pro Asn Ile Ser Phe Gln Gly Leu Ser Arg Phe Pro Gly
385                 390                 395                 400
His Ser Trp Gln Gly Asn Leu Asn Thr Thr Arg Phe Pro Pro Ser Ser
                405                 410                 415
Leu Pro Leu Asn Leu Ala Phe Leu Pro Asp Gln Val Thr Cys Ala Gly
        420                 425                 430
Asn Asn Leu Gly Asp Cys Thr Ser Leu Val Ser Ala Glu Asn Pro Gly
    435                 440                 445
Gly Glu Met Gln Cys Asp Pro Gln Leu Leu Gly Phe Met Gln Asn
450                 455                 460
Val Asn Pro Leu Gly Gly Gln Lys Trp Glu Gln Gln Asn Cys Thr Met
465                 470                 475                 480
Leu Asn Asn Pro Phe Gly Asn Ile Glu Tyr Pro Leu Pro Ala Asp Asn
                485                 490                 495
Met Val Phe Arg Asp Asn Asn Ser Thr Arg Ser Lys Gly Leu Asp Glu
        500                 505                 510
```

```
Ser Leu Met Asn Pro Ile Asp Asn Ser Gln Glu Tyr Val Gly Lys Ala
            515                 520                 525

Thr Thr Met Leu Asp Pro Glu Met Lys Ser Gly Lys Pro Glu Asn Asp
530                 535                 540

Asn Gln His Asp Val Phe Asp Ile Met Asn Glu Met Met Lys Gln
545                 550                 555                 560

Glu Glu Asn Asn Gly Met Val Pro Val Ala Thr Arg Phe Gly Phe Asp
                565                 570                 575

Ser Phe Pro Pro Pro
            580

<210> SEQ ID NO 20
<211> LENGTH: 608
<212> TYPE: PRT
<213> ORGANISM: Arabidopsis thaliana

<400> SEQUENCE: 20

Met Leu Val Gly Lys Ile Ser Gly Tyr Glu Asp Asn Thr Arg Ser Leu
1               5                   10                  15

Glu Arg Glu Thr Ser Glu Ile Thr Ser Leu Leu Ser Gln Phe Pro Gly
            20                  25                  30

Asn Thr Asn Val Leu Val Asp Thr Asn Phe Thr Thr Leu Leu Asn
        35                  40                  45

Met Lys Gln Ile Met Lys Gln Tyr Ala Tyr Gln Val Ser Ile Glu Thr
50                  55                  60

Asp Ala Glu Lys Ala Leu Ala Phe Leu Thr Ser Cys Lys His Glu Ile
65                  70                  75                  80

Asn Ile Val Ile Trp Asp Phe His Met Pro Gly Ile Asp Gly Leu Gln
                85                  90                  95

Ala Leu Lys Ser Ile Thr Ser Lys Leu Asp Leu Pro Val Ile Met
            100                 105                 110

Ser Asp Asp Asn Gln Thr Glu Ser Val Met Lys Ala Thr Phe Tyr Gly
        115                 120                 125

Ala Cys Asp Tyr Val Val Lys Pro Val Lys Glu Glu Val Met Ala Asn
130                 135                 140

Ile Trp Gln His Ile Val Arg Lys Arg Leu Ile Phe Lys Pro Asp Val
145                 150                 155                 160

Ala Pro Pro Val Gln Ser Asp Pro Ala Arg Ser Asp Arg Leu Asp Gln
                165                 170                 175

Val Lys Ala Asp Phe Lys Ile Val Glu Asp Glu Pro Ile Ile Asn Glu
            180                 185                 190

Thr Pro Leu Ile Thr Trp Thr Glu Glu Ile Gln Pro Val Gln Ser Asp
        195                 200                 205

Leu Val Gln Ala Asn Lys Phe Asp Gln Val Asn Gly Tyr Ser Pro Ile
210                 215                 220

Met Asn Gln Asp Asn Met Phe Asn Lys Ala Pro Pro Lys Pro Arg Met
225                 230                 235                 240

Thr Trp Thr Glu Val Ile Gln Pro Val Gln Ser Asn Leu Val Gln Thr
                245                 250                 255

Lys Glu Phe Gly Gln Leu Asn Asp Tyr Ser Gln Ile Met Asn Gln Asp
            260                 265                 270

Ser Met Tyr Asn Lys Ala Ala Thr Lys Pro Gln Leu Thr Trp Thr Glu
        275                 280                 285

Glu Ile Gln Pro Val Gln Ser Gly Leu Val Gln Ala Asn Glu Phe Ser
290                 295                 300
```

Lys Val Asn Gly Tyr Ser Gln Ser Met Asn Gln Asp Ser Met Phe Asn
305                 310                 315                 320

Lys Ser Ala Thr Asn Pro Arg Leu Thr Trp Asn Glu Leu Leu Gln Pro
                325                 330                 335

Val Gln Ser Asp Leu Val Gln Ser Asn Glu Phe Ser Gln Phe Ser Asp
            340                 345                 350

Tyr Ser Gln Ile Met Asn Glu Asp Asn Met Phe Asn Lys Ala Ala Lys
        355                 360                 365

Lys Pro Arg Met Thr Trp Ser Glu Val Phe Gln Pro Val Gln Ser His
370                 375                 380

Leu Val Pro Thr Asp Gly Leu Asp Arg Asp His Phe Asp Ser Ile Thr
385                 390                 395                 400

Ile Asn Gly Gly Asn Gly Ile Gln Asn Met Glu Lys Lys Gln Gly Lys
                405                 410                 415

Lys Pro Arg Lys Pro Arg Met Thr Trp Thr Glu Glu Leu His Gln Lys
                420                 425                 430

Phe Leu Glu Ala Ile Glu Ile Ile Gly Ala Asn Pro Lys Val Leu Val
            435                 440                 445

Glu Cys Leu Gln Glu Met Arg Ile Glu Gly Ile Thr Arg Ser Asn Val
        450                 455                 460

Ala Ser His Leu Gln Lys His Arg Ile Asn Leu Glu Glu Asn Gln Ile
465                 470                 475                 480

Pro Gln Gln Thr Gln Gly Asn Gly Trp Ala Thr Ala Tyr Gly Thr Leu
                485                 490                 495

Ala Pro Ser Leu Gln Gly Ser Asp Asn Val Asn Thr Thr Ile Pro Ser
            500                 505                 510

Tyr Leu Met Asn Gly Pro Ala Thr Leu Asn Gln Ile Gln Gln Asn Gln
        515                 520                 525

Tyr Gln Asn Gly Phe Leu Thr Met Asn Asn Gln Ile Ile Thr Asn
    530                 535                 540

Pro Pro Pro Leu Pro Tyr Leu Asp His His Gln Gln Gln His
545                 550                 555                 560

Gln Ser Ser Pro Gln Phe Asn Tyr Leu Met Asn Glu Glu Leu Leu
                565                 570                 575

Gln Ala Ser Gly Leu Ser Ala Thr Asp Leu Glu Leu Thr Tyr Pro Ser
            580                 585                 590

Leu Pro Tyr Asp Pro Gln Glu Tyr Leu Ile Asn Gly Tyr Asn Tyr Asn
        595                 600                 605

<210> SEQ ID NO 21
<211> LENGTH: 426
<212> TYPE: PRT
<213> ORGANISM: Arabidopsis thaliana

<400> SEQUENCE: 21

Met Ser Val Phe Ser Asn Ile Leu Asp Glu Asn Ser Arg Asn Leu Arg
1               5                   10                  15

Asn Glu Ile Pro Cys Asp Asp Gly Ile Ala Ser Pro Ile Asn Asp Asp
                20                  25                  30

Asp Glu Glu Phe Leu Thr Lys Ser Asn Arg Val Leu Leu Val Gly Ala
            35                  40                  45

Asp Ser Asn Ser Ser Leu Lys Asn Leu Met Thr Gln Tyr Ser Tyr Gln
        50                  55                  60

Val Thr Lys Tyr Glu Ser Gly Glu Glu Ala Met Ala Phe Leu Met Lys

```
            65                  70                  75                  80
        Asn Lys His Glu Ile Asp Leu Val Ile Trp Asp Phe His Met Pro Asp
                        85                  90                  95

Ile Asn Gly Leu Asp Ala Leu Asn Ile Ile Gly Lys Gln Met Asp Leu
                        100                 105                 110

Pro Val Val Ile Met Ser His Glu Tyr Lys Lys Glu Thr Val Met Glu
                        115                 120                 125

Ser Ile Lys Tyr Gly Ala Cys Asp Phe Leu Val Lys Pro Val Ser Lys
        130                 135                 140

Glu Val Ile Ala Val Leu Trp Arg His Val Tyr Arg Lys Arg Met Ser
        145                 150                 155                 160

Lys Ser Gly Leu Asp Lys Pro Gly Glu Ser Gly Thr Val Glu Ser Asp
                        165                 170                 175

Pro Asp Glu Tyr Asp Asp Leu Glu Gln Asp Asn Leu Tyr Glu Ser Asn
                        180                 185                 190

Glu Glu Gly Ser Lys Asn Thr Cys Asp His Lys Glu Glu Lys Ser Pro
                        195                 200                 205

Thr Lys Lys Pro Arg Met Gln Trp Thr Pro Glu Leu His His Lys Phe
        210                 215                 220

Glu Val Ala Val Glu Lys Met Gly Ser Leu Glu Lys Ala Phe Pro Lys
        225                 230                 235                 240

Thr Ile Leu Lys Tyr Met Gln Glu Glu Leu Asn Val Gln Gly Leu Thr
                        245                 250                 255

Arg Asn Asn Val Ala Ser His Leu Gln Lys Tyr Arg Gln Ser Ser Lys
                        260                 265                 270

Lys Thr Cys Thr Pro Gln Glu Pro Gln Glu Asp Phe Val Trp Gly Asn
                        275                 280                 285

Ala Gly Pro Asp Val Thr Leu Ala Ala Ser Lys Thr Leu Leu Ser Ser
        290                 295                 300

His Ala Thr Pro Ser Tyr Leu Ile Asn Asn Gln Ala Ala Pro Arg Gly
        305                 310                 315                 320

Ser Tyr Phe Met Asn Asn Ile Pro Tyr Pro Ser Thr Ser Cys Leu Pro
                        325                 330                 335

Val Asn Asn Asn Asn Cys Phe Met Thr Asn Pro Ser Thr Tyr Ile Asp
                        340                 345                 350

Gln Phe Gln His Gln Leu Gln Gln Gln Gln His Gln Gln Tyr Gln
                        355                 360                 365

Ser Thr Leu Asn Ser Ile Ser Ala Met Leu Thr Lys Gln Glu Ser Arg
        370                 375                 380

His Val Pro Ser Ser Ala Met Glu Asn Ser Glu Pro Leu Met Ile Tyr
        385                 390                 395                 400

Asn Ser Asn Leu Pro Phe Gly Ile Asp Glu Cys Phe Pro Pro Ala Gly
                        405                 410                 415

Phe Asn Ile Phe Asp Gln Ile Gly His Asn
                        420                 425

<210> SEQ ID NO 22
<211> LENGTH: 621
<212> TYPE: PRT
<213> ORGANISM: Arabidopsis thaliana

<400> SEQUENCE: 22

Met Ala Ser Ala Gln Ser Phe Tyr Asn Gln Ser Ser Val Leu Lys Ile
1               5                   10                  15
```

```
Asn Val Met Val Val Asp Asp His Val Phe Leu Asp Ile Met Ser
             20                  25                  30
Arg Met Leu Gln His Ser Lys Tyr Arg Asp Pro Ser Val Met Glu Ile
         35                  40                  45
Ala Val Ile Ala Val Asp Asp Pro Lys Lys Ala Leu Ser Thr Leu Lys
     50                  55                  60
Ile Gln Arg Asp Asn Ile Asp Leu Ile Ile Thr Asp Tyr Tyr Met Pro
65                  70                  75                  80
Gly Met Asn Gly Leu Gln Leu Lys Lys Gln Ile Thr Gln Glu Phe Gly
                 85                  90                  95
Asn Leu Pro Val Leu Val Met Ser Ser Asp Thr Asn Lys Glu Glu Glu
             100                 105                 110
Ser Leu Ser Cys Gly Ala Met Gly Phe Ile Pro Lys Pro Ile His Pro
         115                 120                 125
Thr Asp Leu Thr Lys Ile Tyr Gln Phe Ala Leu Ser Asn Lys Arg Asn
     130                 135                 140
Gly Lys Ser Thr Leu Ser Thr Glu Gln Asn His Lys Asp Ala Asp Val
145                 150                 155                 160
Ser Val Pro Gln Gln Ile Thr Leu Val Pro Glu Gln Ala Asp Val Leu
                 165                 170                 175
Lys Thr Lys Arg Lys Asn Cys Ser Phe Lys Ser Asp Ser Arg Thr Val
             180                 185                 190
Asn Ser Thr Asn Gly Ser Cys Val Ser Thr Asp Gly Ser Arg Lys Asn
         195                 200                 205
Arg Lys Arg Lys Pro Asn Gly Gly Pro Ser Asp Asp Gly Glu Ser Met
     210                 215                 220
Ser Gln Pro Ala Lys Lys Lys Ile Gln Trp Thr Asp Ser Leu His
225                 230                 235                 240
Asp Leu Phe Leu Gln Ala Ile Arg His Ile Gly Leu Asp Lys Ala Val
                 245                 250                 255
Pro Lys Lys Ile Leu Ala Phe Met Ser Val Pro Tyr Leu Thr Arg Glu
             260                 265                 270
Asn Val Ala Ser His Leu Gln Lys Tyr Arg Ile Phe Leu Arg Arg Val
         275                 280                 285
Ala Glu Gln Gly Leu Tyr Ser Met Leu Ser Asp Arg Gly Ile Asp Ser
     290                 295                 300
Met Phe Arg Gln Thr His Ile Lys Glu Pro Tyr Phe Asn Tyr Tyr Thr
305                 310                 315                 320
Pro Ser Thr Ser Trp Tyr Asp Thr Arg Leu Asn Asn Arg Ser Phe Tyr
                 325                 330                 335
Ser Lys Pro Val His Gly Phe Gly Gln Ser Lys Leu Leu Ser Thr Thr
             340                 345                 350
Arg Glu Pro Val Cys Phe Asn Gln Met Pro Tyr Asn Tyr Met Asn Arg
         355                 360                 365
Ser Ser Thr Tyr Glu Pro His Arg Ile Gly Ser Gly Ser Asn Leu Thr
     370                 375                 380
Leu Pro Ile Gln Ser Asn Leu Ser Phe Pro Asn Gln Pro Ser Gln Asn
385                 390                 395                 400
Glu Glu Arg Arg Ser Phe Glu Pro Pro Val Met Ala Asn Lys Ile
                 405                 410                 415
Ala Gln Thr Ser Gln Val Leu Gly Phe Gln Leu Gly Pro Ser Ala
             420                 425                 430
Ile Ser Gly His Asn Phe Asn Asn Asn Met Thr Ser Arg Tyr Gly Ser
```

```
            435                 440                 445
Leu Ile Pro Ser Gln Pro Gly Pro Ser His Phe Ser Tyr Gly Met Gln
    450                 455                 460

Ser Phe Leu Asn Asn Glu Asn Val Thr Tyr Asn Pro Gln Pro Pro Ala
465                 470                 475                 480

Asn Ala Thr Thr Gln Pro Asn Leu Asp Glu Leu Pro Gln Leu Glu Asn
                485                 490                 495

Leu Asn Leu Tyr Asn Asp Phe Gly Asn Thr Ser Glu Leu Pro Tyr Asn
            500                 505                 510

Ile Ser Asn Phe Gln Phe Asp Asp Asn Lys His Gln Gln Gly Glu Ala
        515                 520                 525

Asp Pro Thr Lys Phe Glu Leu Pro Ala Ala Lys Phe Ser Thr Glu Leu
    530                 535                 540

Asn His Glu Asp Asp Gly Asp Trp Thr Phe Val Asn Ile Asn Gln Gly
545                 550                 555                 560

Gln Ser Asn Gly Glu Thr Ser Asn Thr Ile Ala Ser Pro Glu Thr Asn
                565                 570                 575

Thr Pro Ile Leu Asn Ile Asn His Asn Gln Asn Gln Gly Gln Asp Val
            580                 585                 590

Pro Glu Phe Asn Asp Trp Ser Phe Leu Asp Pro Gln Glu Leu Val Asp
        595                 600                 605

Asp Phe Met Asn Ser Leu Phe Asn Asn Asp Met Asn
    610                 615                 620

<210> SEQ ID NO 23
<211> LENGTH: 341
<212> TYPE: PRT
<213> ORGANISM: Oryza sativa

<400> SEQUENCE: 23

Met Asp His Arg Glu Leu Trp Pro Tyr Gly Leu Arg Val Leu Val Ile
1               5                   10                  15

Asp Asp Asp Cys Ser Tyr Leu Ser Val Met Glu Asp Leu Leu Leu Lys
            20                  25                  30

Cys Ser Tyr Lys Val Thr Thr Tyr Lys Asn Val Arg Glu Ala Val Pro
        35                  40                  45

Phe Ile Leu Asp Asn Pro Gln Ile Val Asp Leu Val Ile Ser Asp Ala
    50                  55                  60

Phe Phe Pro Thr Glu Asp Gly Leu Leu Ile Leu Gln Glu Val Thr Ser
65                  70                  75                  80

Lys Phe Gly Ile Pro Thr Val Ile Met Ala Ser Ser Gly Asp Thr Asn
                85                  90                  95

Thr Val Met Lys Tyr Val Ala Asn Gly Ala Ser Asp Phe Leu Leu Lys
            100                 105                 110

Pro Val Arg Ile Glu Glu Leu Ser Asn Ile Trp Gln His Ile Phe Arg
        115                 120                 125

Lys Gln Met Gln Asp His Lys Asn Asn Asn Met Val Gly Asn Leu Glu
    130                 135                 140

Lys Pro Gly His Pro Ser Ile Leu Ala Met Ala Arg Ala Thr Pro
145                 150                 155                 160

Ala Thr Thr Lys Ser Thr Ala Thr Glu Ala Leu Leu Ala Pro Leu Glu
                165                 170                 175

Asn Glu Val Arg Asp Asp Met Val Asn Tyr Asn Gly Glu Ile Thr Asp
            180                 185                 190
```

```
Ile Arg Asp Leu Arg Lys Ser Arg Leu Thr Trp Thr Thr Gln Leu His
        195                 200                 205

Arg Gln Phe Ile Ala Ala Val Asn His Leu Gly Glu Asp Lys Ala Val
    210                 215                 220

Pro Lys Lys Ile Leu Gly Ile Met Lys Val Lys His Leu Thr Arg Glu
225                 230                 235                 240

Gln Val Ala Ser His Leu Gln Lys Tyr Arg Met Gln Leu Lys Lys Ser
                245                 250                 255

Ile Pro Thr Thr Ser Lys His Gly Ala Thr Leu Ser Ser Thr Ala Leu
                260                 265                 270

Asp Lys Thr Gln Asp His Pro Ser Arg Ser Gln Tyr Phe Asn Gln Asp
            275                 280                 285

Gly Cys Met Glu Ile Met Asp Tyr Ser Leu Pro Arg Asp Asp Leu Ser
        290                 295                 300

Ser Gly Ser Glu Cys Met Leu Glu Glu Gln Asn Asp Tyr Ser Ser Glu
305                 310                 315                 320

Gly Phe Gln Asp Phe Arg Trp Asp Ser Asp Lys Gln Glu Tyr Gly Pro
                325                 330                 335

Cys Phe Trp Asn Phe
                340

<210> SEQ ID NO 24
<211> LENGTH: 691
<212> TYPE: PRT
<213> ORGANISM: Oryza sativa

<400> SEQUENCE: 24

Met Ala Pro Val Glu Asp Gly Gly Val Glu Phe Pro Val Gly Met
1               5                   10                  15

Lys Val Leu Val Asp Asp Pro Thr Cys Leu Ala Val Leu Lys
                20                  25                  30

Arg Met Leu Leu Glu Cys Arg Tyr Asp Ala Thr Thr Cys Ser Gln Ala
            35                  40                  45

Thr Arg Ala Leu Thr Met Leu Arg Glu Asn Arg Arg Gly Phe Asp Val
        50                  55                  60

Ile Ile Ser Asp Val His Met Pro Asp Met Asp Gly Phe Arg Leu Leu
65                  70                  75                  80

Glu Leu Val Gly Leu Glu Met Asp Leu Pro Val Ile Met Met Ser Ala
                85                  90                  95

Asp Ser Arg Thr Asp Ile Val Met Lys Gly Ile Lys His Gly Ala Cys
            100                 105                 110

Asp Tyr Leu Ile Lys Pro Val Arg Met Glu Glu Leu Lys Asn Ile Trp
        115                 120                 125

Gln His Val Ile Arg Lys Lys Phe Asn Glu Asn Lys Glu His Glu His
    130                 135                 140

Ser Gly Ser Leu Asp Asp Thr Asp Arg Thr Arg Pro Thr Asn Asn Asp
145                 150                 155                 160

Asn Glu Tyr Ala Ser Ser Ala Asn Asp Gly Ala Glu Gly Ser Trp Lys
                165                 170                 175

Ser Gln Lys Lys Lys Arg Asp Lys Asp Asp Asp Gly Glu Leu Glu
            180                 185                 190

Ser Gly Asp Pro Ser Ser Thr Ser Lys Lys Pro Arg Val Val Trp Ser
        195                 200                 205

Val Glu Leu His Gln Gln Phe Val Asn Ala Val Asn His Leu Gly Ile
    210                 215                 220
```

```
Asp Lys Ala Val Pro Lys Lys Ile Leu Glu Leu Met Asn Val Pro Gly
225                 230                 235                 240

Leu Thr Arg Glu Asn Val Ala Ser His Leu Gln Lys Phe Arg Leu Tyr
            245                 250                 255

Leu Lys Arg Ile Ala Gln His His Ala Gly Ile Ala Asn Pro Phe Cys
            260                 265                 270

Pro Pro Ala Ser Ser Gly Lys Val Gly Ser Leu Gly Gly Leu Asp Phe
        275                 280                 285

Gln Ala Leu Ala Ala Ser Gly Gln Ile Pro Pro Gln Ala Leu Ala Ala
        290                 295                 300

Leu Gln Asp Glu Leu Leu Gly Arg Pro Thr Asn Ser Leu Val Leu Pro
305                 310                 315                 320

Gly Arg Asp Gln Ser Ser Leu Arg Leu Ala Ala Val Lys Gly Asn Lys
                325                 330                 335

Pro His Gly Glu Arg Glu Ile Ala Phe Gly Gln Pro Ile Tyr Lys Cys
            340                 345                 350

Gln Asn Asn Ala Tyr Gly Ala Phe Pro Gln Ser Ser Pro Ala Val Gly
        355                 360                 365

Gly Met Pro Ser Phe Ser Ala Trp Pro Asn Asn Lys Leu Gly Met Ala
370                 375                 380

Asp Ser Thr Gly Thr Leu Gly Gly Met Ser Asn Ser Gln Asn Ser Asn
385                 390                 395                 400

Ile Val Leu His Glu Leu Gln Gln Pro Asp Ala Met Leu Ser Gly
                405                 410                 415

Thr Leu His Ser Leu Asp Val Lys Pro Ser Gly Ile Val Met Pro Ser
            420                 425                 430

Gln Ser Leu Asn Thr Phe Ser Ala Ser Glu Gly Leu Ser Pro Asn Gln
        435                 440                 445

Asn Thr Leu Met Ile Pro Ala Gln Ser Ser Gly Phe Leu Ala Ala Met
        450                 455                 460

Pro Pro Ser Met Lys His Glu Pro Val Leu Ala Thr Ser Gln Pro Ser
465                 470                 475                 480

Ser Ser Leu Leu Gly Gly Ile Asp Leu Val Asn Gln Ala Ser Thr Ser
                485                 490                 495

Gln Pro Leu Ile Ser Ala His Gly Gly Gly Asn Leu Ser Gly Leu Val
            500                 505                 510

Asn Arg Asn Pro Asn Val Val Pro Ser Gln Gly Ile Ser Thr Phe His
        515                 520                 525

Thr Pro Asn Asn Pro Tyr Leu Val Ser Pro Asn Ser Met Gly Met Gly
        530                 535                 540

Ser Lys Gln Pro Pro Gly Val Leu Lys Thr Glu Asn Ser Asp Ala Leu
545                 550                 555                 560

Asn His Ser Tyr Gly Tyr Leu Gly Gly Ser Asn Pro Pro Met Asp Ser
            565                 570                 575

Gly Leu Leu Ser Ser Gln Ser Lys Asn Thr Gln Phe Gly Leu Leu Gly
        580                 585                 590

Gln Asp Asp Ile Thr Gly Ser Trp Ser Pro Leu Pro Asn Val Asp Ser
        595                 600                 605

Tyr Gly Asn Thr Val Gly Leu Ser His Pro Gly Ser Ser Ser Ser Ser
        610                 615                 620

Phe Gln Ser Ser Asn Val Ala Leu Gly Lys Leu Pro Asp Gln Gly Arg
625                 630                 635                 640
```

```
Gly Lys Asn His Gly Phe Val Gly Lys Gly Thr Cys Ile Pro Ser Arg
            645                 650                 655

Phe Ala Val Asp Glu Ile Glu Ser Pro Thr Asn Asn Leu Ser His Ser
            660                 665                 670

Ile Gly Ser Ser Gly Asp Ile Met Ser Pro Asp Ile Phe Gly Phe Ser
            675                 680                 685

Gly Gln Met
    690

<210> SEQ ID NO 25
<211> LENGTH: 696
<212> TYPE: PRT
<213> ORGANISM: Oryza sativa

<400> SEQUENCE: 25

Met Leu Leu Gly Ala Leu Arg Met Glu Glu Arg Lys Gly Leu Met Gly
1               5                   10                  15

Arg Glu Arg Asp Gln Phe Pro Val Gly Met Arg Val Leu Ala Val Asp
            20                  25                  30

Asp Asp Pro Val Cys Leu Lys Val Leu Glu Thr Leu Arg Arg Cys
            35                  40                  45

Gln Tyr His Val Thr Ser Thr Asn Gln Ala Ile Thr Ala Leu Lys Leu
    50                  55                  60

Leu Arg Glu Asn Arg Asp Met Phe Asp Leu Val Ile Ser Asp Val His
65                  70                  75                  80

Met Pro Asp Met Asp Gly Phe Lys Leu Leu Glu Leu Val Gly Leu Glu
            85                  90                  95

Met Asp Leu Pro Val Ile Met Leu Ser Val Asn Gly Glu Thr Lys Thr
            100                 105                 110

Val Met Lys Gly Ile Thr His Gly Ala Cys Asp Tyr Leu Leu Lys Pro
            115                 120                 125

Val Arg Ile Glu Glu Leu Arg Asn Ile Trp Gln His Val Val Arg Arg
            130                 135                 140

Lys Phe Gly Asn Arg Glu Arg Asn Asn Leu Asp Phe Ser Lys Glu Cys
145                 150                 155                 160

Asn Lys Pro Gln Ser Ala Asp Thr Asp His Gly Pro Tyr Gln Pro Thr
            165                 170                 175

Cys Gly Ser Ser Asp Gln Asn Gly Arg Ser Ser Arg Lys Arg Lys Glu
            180                 185                 190

Leu His Gly Glu Asp Asp Glu Gly Asp Asp Asn Asp Tyr Gln Glu
            195                 200                 205

Asn Asp Glu Pro Ser Ala Ala Lys Lys Pro Arg Val Val Trp Ser Val
            210                 215                 220

Glu Leu His Arg Lys Phe Val Ala Ala Val Asn Gln Leu Gly Ile Asp
225                 230                 235                 240

Lys Ala Val Pro Lys Arg Ile Leu Glu Leu Met Asn Val Glu Lys Leu
            245                 250                 255

Thr Arg Glu Asn Val Ala Ser His Leu Gln Lys Tyr Arg Leu Tyr Leu
            260                 265                 270

Lys Arg Leu Gly Ala Val Ala Ser Gln Gln Ala Ser Ile Val Ala Ala
            275                 280                 285

Phe Gly Gly Arg Asp Pro Ser Phe Leu His Ile Gly Ala Phe Glu Gly
            290                 295                 300

Leu Gln Ser Tyr Gln Pro Phe Ala Pro Ser Ala Ala Leu Pro Ser Phe
305                 310                 315                 320
```

Asn Pro His Gly Leu Leu Thr Arg Thr Ser Ala Ala Ala Phe Gly
            325                 330                 335

Leu Gln Glu Leu Ala Ala Pro Ser Ser Thr Ile Gln Thr Ser Thr Gly
        340                 345                 350

Asn Val Thr Val Gly His Cys Leu Glu Glu Asn Gln Gln Ala Asn Leu
            355                 360                 365

Ala Gln Gly Leu Thr Ala Ala Ile Gly Gln Pro Gln Leu Gln Gln Asn
370                 375                 380

Trp Ile His Gln Glu Gly Asn Gly Leu Ser Asp Val Phe Ser Gly Ser
385                 390                 395                 400

Ser Leu Thr Asn Thr Leu Ser Ser Thr Leu Gln Arg Val Pro Ser Ser
            405                 410                 415

Ser Leu Pro Pro Gln Glu Leu Leu Glu Cys Lys Gln Ala Lys Val Ser
            420                 425                 430

Met Pro Pro Ser Ile Arg Ile Pro Pro Ser Ser Ala Leu Leu Glu
            435                 440                 445

Arg Thr Leu Gly Val Ser Thr Asn Leu Gly Asp Ser Ser Ile Ser Gln
            450                 455                 460

Gln Gly Ala Leu Pro Ile Asp Gly Gly Phe Ser Ala Asp Arg Leu Pro
465                 470                 475                 480

Leu His Ser Ser Phe Asp Gly Ala Val Ala Thr Lys Leu Asp Thr Ser
                485                 490                 495

Leu Ala Ala Ser Gln Arg Glu Ile Gly Gln Gln Gly Lys Phe Ser Val
            500                 505                 510

Ser Met Leu Val Ser Pro Ser Asp Asn Leu Ala Leu Ala Lys Asn Ala
            515                 520                 525

Lys Thr Gly Ala Ser Ser Ser Gly Ser Thr Ile Ile Leu Pro Leu Asp
            530                 535                 540

Thr Ala Arg His Ser Asp Tyr Leu Gln Phe Gly Gly Ala Ser Asn Ser
545                 550                 555                 560

Leu Gln Lys Met Asp Gly Gln Lys Gln Asp His Ile Gln Ser Ser Asn
                565                 570                 575

Ile Ile Trp Ser Ser Met Pro Ser Thr Gln Leu Pro Ser Asp Thr Gln
            580                 585                 590

Ile His Asn Thr Gln Asn Gln Arg Leu Asp Ser Gly Ser Phe Asn His
            595                 600                 605

Asn Ile Gly Ala His Leu Ala Asp Gln Thr Asn Ala Ser Ala Ser Ile
            610                 615                 620

Leu Pro Gln Met Lys Phe Asp Thr Arg Ile Ser Glu Glu Lys Met Lys
625                 630                 635                 640

Gln Lys Asn Thr Tyr Asp Leu Gly Ser Ser Lys Leu Gln Gly Gly Phe
                645                 650                 655

Asn Ser Ser Gly Cys Asn Phe Asp Gly Leu Leu Asn Ser Ile Ile Lys
            660                 665                 670

Val Glu Lys Asp Asp Leu Pro Phe Met Asp Asn Glu Leu Gly Cys Asp
            675                 680                 685

Leu Phe Pro Leu Gly Ala Cys Ile
    690                 695

<210> SEQ ID NO 26
<211> LENGTH: 688
<212> TYPE: PRT
<213> ORGANISM: Oryza sativa

<400> SEQUENCE: 26

```
Met Arg Ala Ala Glu Glu Arg Lys Gly Val Val Pro Ala Ala Arg Arg
1               5                   10                  15

Arg Asp Gln Phe Pro Val Gly Met Arg Val Leu Ala Val Asp Asp Asp
                20                  25                  30

Pro Val Cys Leu Lys Val Leu Glu Thr Leu Leu Leu Arg Cys Gln Tyr
            35                  40                  45

His Val Thr Thr Thr Asn Gln Ala Ala Ile Ala Leu Lys Met Leu Arg
    50                  55                  60

Glu Asn Arg Asp Met Phe Asp Leu Val Ile Ser Asp Val His Met Pro
65                  70                  75                  80

Asp Met Asp Gly Phe Lys Leu Leu Glu Leu Val Gly Leu Glu Met Asp
                85                  90                  95

Leu Pro Val Ile Met Leu Ser Val Asn Gly Glu Thr Lys Thr Val Leu
            100                 105                 110

Lys Gly Ile Thr His Gly Ala Cys Asp Tyr Leu Leu Lys Pro Val Arg
        115                 120                 125

Ile Glu Glu Leu Arg Asn Ile Trp Gln His Val Ile Arg Arg Lys Phe
130                 135                 140

Ser Thr Arg Asp Arg Ala Asn Leu Asp Phe Tyr Glu Glu Cys Asn Lys
145                 150                 155                 160

Pro Pro Asn Ala Asp Ser Asp His Val His Gly His Val Thr Cys Gly
                165                 170                 175

Ser Pro Asp Gln Ser Gly Arg Pro Ser Lys Lys Arg Lys Glu Tyr Cys
            180                 185                 190

Ser Glu Glu Glu Asp Glu Gly Glu Val Asn Thr Gln Asp Ile Asp Asp
        195                 200                 205

Pro Ser Ala Pro Lys Lys Pro Arg Val Val Trp Ser Val Glu Leu His
210                 215                 220

Arg Lys Phe Val Ala Ala Val Asn Gln Leu Gly Ile Asp Lys Ala Val
225                 230                 235                 240

Pro Lys Arg Ile Leu Glu Leu Met Asn Val Glu Lys Leu Thr Arg Glu
                245                 250                 255

Asn Val Ala Ser His Leu Gln Lys Tyr Arg Leu Tyr Leu Lys Arg Leu
            260                 265                 270

Ser Ala Val Ala Ser Gln Gln Val Ser Ile Val Ala Ala Leu Gly Gly
        275                 280                 285

Arg Asp Pro Phe Leu His Met Gly Gly Phe Glu Gly Leu Gln Gly Tyr
290                 295                 300

Gln Ala Phe Thr Ser Ser Ala Ala Leu Ser Ser Phe Thr Pro His Gly
305                 310                 315                 320

Leu Leu Asn Ser Pro Arg Asn Asn Pro Ala Ala Leu Gly Thr Gln Gly
                325                 330                 335

Val Pro Ala Ser Lys Ser Ile Gln Thr Met Ser Gly Ser His Thr Leu
            340                 345                 350

Ser His Ser Ile Asn Asp Ala Asn Lys Tyr His Leu Ser Leu Pro Gly
        355                 360                 365

Asn Gln Lys Gly Asn Leu Gly Gln Gly Leu Ala Thr Ser Leu Gly Gln
370                 375                 380

Thr Gln Met Gln Gln Lys Trp Ile His Glu Glu Thr Asp Asp Leu Ser
385                 390                 395                 400

Thr Ile Leu Ser Gly Asn Gly Leu Ser Asn Gly Met Ser Gly Thr Leu
                405                 410                 415
```

```
Gln Ser Val Thr Ser Ser Pro Leu Leu Pro Gln Glu Leu Ala Glu Cys
                420                 425                 430

Thr Gln Ala Lys Ile Val Ser Gln Pro Ser Ile Arg Thr Ser Ser Val
            435                 440                 445

Ser Ser Glu His Ile Glu Gly Ala Val Gly Val Ser Ser Gly Leu Leu
        450                 455                 460

Glu Ser Arg Val Ser Gln Gln Ser Thr Ile Pro Leu Ser Gly Phe Ser
465                 470                 475                 480

Ala Asn Gly Leu Leu Ile His Gly Ser Phe Asn Asn Thr Cys Ala Asn
                485                 490                 495

Lys Leu Gly Gly Thr Ser Ser Cys Ala Pro Ala Arg Ser Ser Asn
                500                 505                 510

Asp Leu Met Val Ala Arg Asp Thr Lys Gly Gly Ala Ser Ser Phe Gly
            515                 520                 525

Gly Ala Met Leu Leu Pro Pro Asp Thr Glu Gln Lys Tyr Leu Asn Phe
        530                 535                 540

Gly Gly Gly Asn Gly Leu Lys Gln Lys Phe Asp Asp Arg Thr Ala Asp
545                 550                 555                 560

Ser Leu Phe Asp Leu Lys Phe Val Trp Ser Ser Val Pro Ser Ser Gln
                565                 570                 575

Leu Ala Ser Asn Ile Gly Ala His His Ala Met Ser Gln Arg Trp Asn
            580                 585                 590

Asn Ser Ser Ser Asn Ser Ser Asn Ile Gly Ala Arg Met Ile Gly Gln
        595                 600                 605

Ala Thr Ser Ser Gly Ser Thr Val Ile Pro Gln Met Lys Thr Asp Phe
            610                 615                 620

Leu Val Ser Gly Asp Met Ala Met Pro Lys Asn Ala Ser Asp Leu Ser
625                 630                 635                 640

Ile Pro Lys Leu Gln Ser Glu Leu Ser Ser Ser Cys Ser Phe Asp
                645                 650                 655

Gly Leu Leu Asn Ser Ile Val Lys Val Glu Lys Asp Asp Val Thr Phe
            660                 665                 670

Ser Asp Asp Leu Gly Cys Gly Asp Phe Tyr Ser Leu Gly Ala Cys Ile
        675                 680                 685

<210> SEQ ID NO 27
<211> LENGTH: 626
<212> TYPE: PRT
<213> ORGANISM: Oryza sativa

<400> SEQUENCE: 27

Met Thr Val Glu Glu Arg Gln Gly Arg Val Gly Gly His Gly Val Ser
1               5                   10                  15

Gly Gly Gly Gly Gly Arg Asp Gln Phe Pro Val Gly Met Arg Val Leu
            20                  25                  30

Ala Val Asp Asp Asp Pro Thr Cys Leu Lys Ile Leu Glu Asn Leu Leu
        35                  40                  45

Leu Arg Cys Gln Tyr His Val Thr Thr Thr Gly Gln Ala Ala Thr Ala
    50                  55                  60

Leu Lys Leu Leu Arg Glu Asn Lys Asp Gln Phe Asp Leu Val Ile Ser
65                  70                  75                  80

Asp Val His Met Pro Asp Met Asp Gly Phe Lys Leu Leu Glu Leu Val
                85                  90                  95

Gly Leu Glu Met Asp Leu Pro Val Ile Met Leu Ser Ala Asn Gly Glu
```

```
            100             105             110
Thr Gln Thr Val Met Lys Gly Ile Thr His Gly Ala Cys Asp Tyr Leu
            115             120             125

Leu Lys Pro Val Arg Leu Glu Gln Leu Arg Thr Ile Trp Gln His Val
            130             135             140

Ile Arg Arg Lys Asn Cys Asp Ala Lys Asn Arg Gly Asn Asp Asp Asp
145             150             155             160

Ala Gly Gln Lys Ala Gln Gly Met Asn Asn Glu Gly Glu Ser Ile Gly
            165             170             175

Ala Asn Arg Asn Lys Arg Gln Ser Arg Lys Ser Arg Asp Glu Asn Gly
            180             185             190

Asp Asp Gly Asp Asp Ser Asp Glu Asn Ser Asn Glu Asn Gly Asp Ser
            195             200             205

Ser Thr Gln Lys Lys Pro Arg Val Val Trp Ser Val Glu Leu His Arg
            210             215             220

Lys Phe Val Ala Ala Val Asn Gln Leu Gly Ile Glu Lys Ala Val Pro
225             230             235             240

Lys Lys Ile Leu Asp Leu Met Asn Val Glu Asn Ile Thr Arg Glu Asn
            245             250             255

Val Ala Ser His Leu Gln Lys Tyr Arg Leu Tyr Leu Lys Arg Leu Ser
            260             265             270

Thr Asp Ala Ser Arg Gln Ala Asn Leu Ala Ala Phe Gly Gly Arg
            275             280             285

Asn Pro Ala Tyr Ile Asn Met Asn Ser Phe Gly Asn Tyr Asn Ala Tyr
            290             295             300

Gly Arg Tyr Arg Thr Val Pro Thr Ala Gly His Thr Gln Ala Asn Asn
305             310             315             320

Ile Leu Thr Arg Met Asn Ser Pro Ser Ala Phe Gly Val His Gly Leu
            325             330             335

Leu His Ser Gln Pro Ile Gln Leu Gly His Ala Gln Asn Asn Leu Ser
            340             345             350

Thr Ser Leu Asn Asp Leu Gly Gly Leu Asn Asn Gly Asn Met Ile Arg
            355             360             365

Gly Ala Gln Met Ser Thr Ile Leu Thr Gly Pro Ser Gly Asn Ser Phe
            370             375             380

Pro Asn Ile Ser Asn Gly Ala Pro Leu Ala Thr Ala Asn Arg Ser Leu
385             390             395             400

Gln Pro Leu Glu Ser Ser Asn Gln Gln His Leu Ser Arg Val His Ser
            405             410             415

Ser Ser Ala Asp Pro Phe Ser Thr Leu Val Gly Glu Ser Pro Gln Phe
            420             425             430

Pro Asp Leu Gly Arg Thr Thr Asn Thr Trp Gln Thr Ala Val Pro Ser
            435             440             445

Asn Ile Gln Asp Arg Gly His Asn Asp Asn Met Ser Gln Ala Thr Leu
            450             455             460

His Met Asn Gly Pro Lys Ile Glu Pro Val Ser Ser Phe Thr Ser Ser
465             470             475             480

Asn Gln Ile Pro Leu Leu Gly Asn Glu Met Gln Gly Asn Val Ala Ser
            485             490             495

Leu Ala Ser Asn Val Pro Ile Ala Phe Asn Gln Asp Thr Ser Pro Phe
            500             505             510

Asn Tyr Gly Ser Ser Thr Asn Ser Arg Asp Met Leu Asn Asn Ser His
            515             520             525
```

```
Val Phe Ser Asn Ser Ser Ile Asn Thr Ser Leu Pro Asn Leu Ser Leu
            530                 535                 540

Asp Asn Pro Ala Val Pro Arg Gln Thr Leu Asp Arg Gly Asn Thr Gly
545                 550                 555                 560

Ile Val Ser Pro Met Gln Asp Gly Arg Ile His His Gln Ala Val Ser
                565                 570                 575

Asn Gln Leu Asn Tyr Asn Asp Asp Leu Met Arg Thr Thr Gly Leu Gln
            580                 585                 590

Arg Gly Leu Ser Gly Gly Leu Asp Asp Ile Val Val Asp Met Phe Arg
        595                 600                 605

Pro Asp Arg Glu Asp Asp Gly Val Pro Tyr Ile Asp Gly Asp Trp Glu
    610                 615                 620

Leu Val
625

<210> SEQ ID NO 28
<211> LENGTH: 694
<212> TYPE: PRT
<213> ORGANISM: Oryza sativa

<400> SEQUENCE: 28

Met Ala Ala Thr Gln Ala Thr Ala Ala Arg Lys Phe Pro Glu Gly Leu
1               5                   10                  15

Arg Val Leu Ala Val Asp Asp Ser Pro Val Cys Leu Met Leu Leu Glu
            20                  25                  30

Ala Leu Leu Arg Arg Cys Lys Tyr Gln Pro Thr Met Thr Arg Asp Ala
        35                  40                  45

Ala Thr Ala Leu Arg Met Leu Arg Glu Arg Pro Gly Asp Phe Asp Leu
    50                  55                  60

Val Ile Ser Asp Val His Met Leu Asp Met Asp Gly Phe Lys Leu Leu
65                  70                  75                  80

Glu Leu Ile Gly Leu Glu Met Asp Leu Pro Val Ile Met Gln Ser Ala
                85                  90                  95

Asn Gly Glu Leu Glu Thr Met Met Lys Gly Val Thr His Gly Ala Cys
            100                 105                 110

Asp Tyr Leu Val Lys Pro Val Ser Leu Lys Asp Ile Gln Asn Ile Trp
        115                 120                 125

Gln His Val Trp Arg Lys Arg Lys Leu Asp Ile Arg Asn His Asn Gly
    130                 135                 140

Gly Tyr Asn Asp Gly Gly Glu Leu Val Gly Ala Thr Arg Thr Lys Arg
145                 150                 155                 160

Lys Tyr Thr Arg Lys Met Arg Asn Asp Gly Asp Asn Tyr Gly Glu Asn
                165                 170                 175

Lys Glu Asn Met Asp Ser Thr Leu Lys Arg Gln Arg Val Val Trp Thr
            180                 185                 190

Pro Glu Leu His Arg Asp Phe Val Ile Ala Val His Glu Leu Gly Val
        195                 200                 205

Asp Arg Ala Val Pro Arg Lys Ile Leu Arg Met Met Lys Val Asp Tyr
    210                 215                 220

Met Thr Arg Glu Asn Ile Ala Ser His Leu Gln Lys Tyr Arg Leu Tyr
225                 230                 235                 240

Leu Lys Arg Ile Ser Thr Gln Thr Gly Met Asp Pro Asp Gln Phe Pro
                245                 250                 255

Glu Lys Trp Lys Tyr Met Asn Glu Leu Asp Ala Leu Lys Asn Tyr Cys
```

```
                        260                 265                 270
            Glu Asn Gly Arg Tyr Arg Leu Thr Pro Ala Ile Ala Ser Ser Ser Ser
                        275                 280                 285

Ser Asn Pro Phe Ala Arg Met Asn Ser Ala Ser Ala Leu Ala Thr Asn
                        290                 295                 300

Gly Phe Leu Pro Thr His Ser Val Gln Leu Lys Asn Ser Gln Arg Asn
            305                 310                 315                 320

Met Ala Met Gly Thr Val Gly His Gly Gly Ser Pro Gly Asn Asn Pro
                                325                 330                 335

Val Phe Gln Pro Leu Gln Asn Ser Ser Asn Ala Arg Lys Cys Phe Pro
                        340                 345                 350

Ser Gly Pro Ser Gly Ser Ser Phe Ala Asn Ile Ser Asn Gly Leu Val
                        355                 360                 365

Leu Asp Thr Asp Ser Gly Ser Ser Tyr Ala Gly Met Phe Cys Lys
                        370                 375                 380

Ser Met Trp Glu Thr Ser Asn Gly Ser Pro Ser Cys His Ser Gly Asn
            385                 390                 395                 400

Ser Ser Ala Asn Lys Ser Asn Asn Gly Val Ser Ala Pro Ala Asn Gln
                        405                 410                 415

Phe Gln Val Gln Ser Lys Phe Gly Phe Ser Ala Leu Ala Asn Gln Phe
                        420                 425                 430

Pro Val Gln Ser Asn Cys Gly Phe Ser Ala Pro Ala Asn Gln Tyr Gln
                        435                 440                 445

Val Gln Ser Asn Gly Gly Phe Ser Val Pro Ala Asn Gln Phe Pro Val
            450                 455                 460

Gln Ser Asn Gly Glu Phe Leu Ala Pro Thr Asn Gln Phe Pro Val Gln
            465                 470                 475                 480

Tyr Pro Glu Val Asn Asn Gln Pro Leu Val Gln Met Asn Gln Ser Ser
                        485                 490                 495

Thr Asn His Phe Ser Thr Ile Gly Asn Asp Tyr Gln Phe Pro Asp Leu
                        500                 505                 510

Ala Asn Cys Ser Lys Tyr Trp Gln Pro Thr Ala Pro Ser Met Phe Pro
                        515                 520                 525

Asp Leu Gly His Asn Asp Gly Thr Ser Phe Arg Pro Ser Gln Ala Asn
                        530                 535                 540

Ile Ala Asn Ile Asn Gln Leu Ser Ser Phe Ala Ala Ser Ser Gly Gln
            545                 550                 555                 560

Glu Pro Met Phe Gly Asp Glu Leu His Gly Gln Met Ser Pro Ile Met
                        565                 570                 575

Ser Thr Ile Ser Leu Ser Asp Phe Asp Asp Gln Met Gly Ser Phe Asn
                        580                 585                 590

Ile Gly Asn Asp Thr Ser Pro Ala Glu Met Met His Asp Asn Phe Ser
                        595                 600                 605

Leu Gly Ser Asp Ser Asn Ile Ser Ser Ser Thr Pro Thr Asp Ser Ser
                        610                 615                 620

Phe Gly Ser Thr Phe Pro Asp Phe His Leu Asp Ser Pro Glu Met Pro
            625                 630                 635                 640

Ala Gln Met Leu Asn Gly Gly Asp Glu Asp Gly Ile Leu Leu Pro Val
                        645                 650                 655

Leu Asp Asp Thr Val Asp Gln Gln Asp Leu Phe Asp Gln Leu Asp Glu
                        660                 665                 670

Asn Asn Gly Arg Glu Lys Leu Gly Ser Gly Arg Cys Val Arg Lys Gly
                        675                 680                 685
```

```
Pro Phe Glu Cys Phe Phe
    690

<210> SEQ ID NO 29
<211> LENGTH: 586
<212> TYPE: PRT
<213> ORGANISM: Oryza sativa

<400> SEQUENCE: 29

Met Asp Ala Thr Ala Phe Pro Tyr Gly Leu Arg Val Leu Val Val Asp
1               5                   10                  15

Asp Asp Pro Thr Trp Leu Lys Ile Leu Glu Lys Met Leu Arg Lys Cys
            20                  25                  30

Ser Tyr Glu Val Thr Thr Cys Gly Leu Ala Arg Val Ala Leu Asp Ile
        35                  40                  45

Leu Arg Glu Arg Lys Asn Lys Phe Asp Ile Val Ile Ser Asp Val Asn
50                  55                  60

Met Pro Asp Met Asp Gly Phe Lys Leu Leu Glu His Ile Gly Leu Glu
65                  70                  75                  80

Met Asp Leu Pro Val Ile Met Met Ser Ile Asp Gly Glu Thr Ser Arg
                85                  90                  95

Val Met Lys Gly Val Gln His Gly Ala Cys Asp Tyr Leu Leu Lys Pro
            100                 105                 110

Val Arg Met Lys Glu Leu Arg Asn Ile Trp Gln His Val Tyr Arg Lys
        115                 120                 125

Lys Met His Glu Val Lys Glu Ile Glu Gly Asn Asp Ser Cys Asp Asp
130                 135                 140

Leu Gln Ile Leu Arg Asn Ser Phe Glu Gly Leu Asp Glu Lys Ser Leu
145                 150                 155                 160

Phe Met Arg Ser Asp Ser Asp Thr Met Arg Lys Arg Lys Asp Val Asp
                165                 170                 175

Lys Asp His Ala Asp Gln Glu Ser Ser Asp Gly Asn Thr Val Lys Lys
            180                 185                 190

Ala Arg Val Val Trp Ser Val Asp Leu His Gln Lys Phe Val Asn Ala
        195                 200                 205

Val Asn Gln Ile Gly Phe Asp Ser Glu Cys Ser Pro Lys Gly Pro Lys
210                 215                 220

Lys Ile Leu Asp Leu Met Asn Val Pro Gly Leu Thr Arg Glu Asn Val
225                 230                 235                 240

Ala Ser His Leu Gln Lys Tyr Arg Leu Tyr Leu Ser Arg Leu Gln Lys
                245                 250                 255

Gln Asn Glu Glu Arg Ile Leu Gly Ala Ala Arg Gln Asp Phe Ser His
            260                 265                 270

Lys Gly Thr Ser Glu Asn Leu Asn Leu Arg Ser Ser Phe Gln Glu Gln
        275                 280                 285

Pro Ser Asn Ile Ala Asn Gly Tyr Pro His Ala Ser Gln Asn Ile Gln
290                 295                 300

Thr Gln Ala Asn Met Leu Asp Ser Gln Leu Glu Asp Thr Lys Ser Thr
305                 310                 315                 320

Val Pro Leu Pro Val Pro Asp Lys Lys Arg Thr Leu Ala Ser Asp Ala
                325                 330                 335

Ala Asp Ser Gln Asn Val Thr Ser Ala Ser Ser Leu Gly Gly Val Leu
            340                 345                 350

Ser Phe Lys Ser Met Pro Val Asn Gln Asp Arg Lys Pro Ser Glu Thr
```

```
            355                 360                 365
Met Ile Leu Glu Cys Gln Ala Trp Thr Gly Gly Ile Pro Ser Lys Gln
    370                 375                 380

Phe Met Gln Tyr Pro Lys His Asn His Glu Arg Cys Asp Leu Leu Gly
385                 390                 395                 400

Asp Tyr Ser Cys Leu Pro Lys Pro Asp Leu Glu His Pro Val Gly Pro
                405                 410                 415

Ser Asn Leu Tyr Ala Pro Pro Leu Ile Ser Met Ser Cys Gly Met
            420                 425                 430

Glu Gly Asp Ala Arg Asp Phe Ser Asp Val Lys Pro Ala Ile Met Asp
        435                 440                 445

Cys Ile Lys Ser Leu Ser Pro Ala Leu Thr Cys Thr Val Asp Ser Val
    450                 455                 460

Ser Val Gln Leu Ser Asp Ser Val Val Thr Ser Ile Asp Gly Asp Leu
465                 470                 475                 480

Lys Ser Ser Gly Val Asp Gly Leu Pro Ser Ile Lys Asp Cys Cys Leu
                485                 490                 495

Asp Gln Thr Asn Ser Gln Gly Ser Leu Arg Pro Ser Gln Glu Pro Ser
            500                 505                 510

Ile Ile Gly Ser Thr Glu Leu Ala Ser Leu Pro Glu Asp Leu Pro Ser
        515                 520                 525

Tyr Pro Leu His Gly Val Ser Leu Glu Asn Ile Gly Leu Ser Ser Ile
    530                 535                 540

Asp Leu Leu Asn Tyr Ser Asp Ala Met Ile Leu Ser Gly Leu Gln Ser
545                 550                 555                 560

Asn Trp Tyr Asp Asp Leu Glu Phe Ser Ser Glu Met Met Asp Tyr Pro
                565                 570                 575

Ser Ile Asp Glu Cys Leu Phe Ala Ser Ser
            580                 585

<210> SEQ ID NO 30
<211> LENGTH: 686
<212> TYPE: PRT
<213> ORGANISM: Zea mays

<400> SEQUENCE: 30

Met Ala Ala Ala Glu Ala Arg Gly Gly Glu Phe Pro Val Gly Met Lys
1               5                   10                  15

Val Leu Val Val Asp Asp Asp Pro Thr Cys Leu Val Val Leu Lys Arg
                20                  25                  30

Met Leu Leu Glu Cys Arg Tyr Asp Val Thr Thr Cys Pro Gln Ala Thr
            35                  40                  45

Arg Ala Leu Thr Met Leu Arg Glu Asn Arg Arg Gly Phe Asp Val Ile
    50                  55                  60

Ile Ser Asp Val His Met Pro Asp Met Asp Gly Phe Arg Leu Leu Glu
65                  70                  75                  80

Leu Val Gly Leu Glu Met Asp Leu Pro Val Ile Met Met Ser Ala Asp
                85                  90                  95

Ser Arg Thr Asp Ile Val Met Asn Gly Val Lys His Gly Ala Cys Asp
            100                 105                 110

Tyr Leu Ile Lys Pro Val Arg Met Glu Glu Leu Lys Asn Ile Trp Gln
        115                 120                 125

His Val Ile Arg Lys Lys Phe Asn Glu Asn Lys Asp His Glu His Ser
    130                 135                 140
```

```
Gly Ser Leu Asp Asp Thr Asp Arg Asn Arg Pro Thr Asn Asn Asp Asn
145                 150                 155                 160

Glu Tyr Ala Ser Ser Ala Asn Asp Gly Gly Asp Gly Ser Trp Lys Ser
            165                 170                 175

Gln Arg Lys Lys Arg Glu Lys Glu Asp Asp Glu Thr Asp Leu Glu Asn
        180                 185                 190

Gly Asp Pro Ser Ser Thr Ser Lys Lys Pro Arg Val Val Trp Ser Val
        195                 200                 205

Glu Leu His Gln Gln Phe Val Asn Ala Val Asn His Leu Gly Ile Asp
    210                 215                 220

Lys Ala Val Pro Lys Lys Ile Leu Glu Leu Met Asn Val Pro Gly Leu
225                 230                 235                 240

Thr Arg Glu Asn Val Ala Ser His Leu Gln Lys Phe Arg Leu Tyr Leu
            245                 250                 255

Lys Arg Ile Ala Gln His His Ala Gly Ile Pro His Pro Phe Val Ala
        260                 265                 270

Pro Val Ser Ser Ala Asn Val Ala Pro Leu Gly Gly Leu Glu Phe Gln
        275                 280                 285

Ala Leu Ala Ala Ser Gly Gln Ile Pro Pro Gln Ala Leu Ala Ala Leu
    290                 295                 300

Gln Asp Glu Leu Leu Gly Arg Pro Thr Ser Ser Leu Ala Leu Pro Gly
305                 310                 315                 320

Arg Asp Gln Ser Ser Leu Arg Val Ala Ala Thr Lys Gly Asn Lys His
            325                 330                 335

His Glu Glu Arg Glu Ile Ala Phe Gly Gln Pro Ile Tyr Lys Cys Gln
        340                 345                 350

Asn Asn Ala Tyr Gly Ala Phe Pro Gln Ser Ser Pro Ala Val Gly Gly
        355                 360                 365

Leu Gln Pro Phe Ala Ala Trp Pro Asn Asn Lys Val Gly Met Pro Asp
    370                 375                 380

Ser Thr Ser Thr Leu Gly Asn Val Gly Asn Ser Gln Asn Ser Asn Met
385                 390                 395                 400

Leu Leu His Glu Leu Gln Gln Gln Pro Asp Thr Leu Leu Gly Thr
            405                 410                 415

Leu His Asn Ile Asp Ala Lys Pro Ser Gly Val Val Met Ser Ser Gln
        420                 425                 430

Ser Leu Asn Thr Phe Pro Ala Ser Glu Gly Ile Ser Pro Asn Gln Asn
        435                 440                 445

Pro Leu Ile Ile Pro Ser Gln Pro Pro Ser Phe Val Ser Ser Ile Pro
    450                 455                 460

Pro Ser Met Lys His Glu Ser Leu Leu Gly Leu Pro Ser Thr Ser Thr
465                 470                 475                 480

Ser Leu Leu Gly Gly Leu Asp Met Val Asn Gln Ala Ser Thr Ser Gln
            485                 490                 495

Ala Leu Ile Ser Ser His Gly Thr Asn Leu Pro Gly Leu Met Asn Arg
        500                 505                 510

Ser Ser Asn Ala Ile Pro Ser Pro Gly Ile Ser Asn Phe Gln Ser Gly
        515                 520                 525

Asn Ile His Tyr Val Val Asn Gln Asn Ala Met Gly Val Ser Ser Arg
    530                 535                 540

Pro Pro Gly Val Leu Lys Thr Glu Ser Thr Asp Ser Leu Ser Cys Ser
545                 550                 555                 560

Tyr Gly Tyr Ile Gly Gly Ser Thr Ser Val Asp Ser Gly Leu Phe Ser
```

```
                        565                 570                 575

Ser Gln Ser Lys Asn Pro Gln Tyr Gly Leu Leu Gln Asn Gln Asn Asp
                580                 585                 590

Val Asn Gly Ser Trp Ser Pro Ser Gln Asp Phe Asp Ser Phe Gly Asn
                595                 600                 605

Ser Leu Gly Gln Gly His Pro Gly Thr Thr Ser Ser Asn Phe Gln Ser
            610                 615                 620

Ser Ala Leu Gly Lys Leu Pro Asp Gln Gly Arg Gly Arg Asn His Gly
625                 630                 635                 640

Phe Val Gly Lys Gly Thr Cys Ile Pro Ser Arg Phe Ala Val Asp Glu
                645                 650                 655

Val Glu Ser Pro Thr Asn Asn Leu Ser His Ser Ile Gly Asn Ser Gly
                660                 665                 670

Asp Ile Val Asn Pro Asp Ile Phe Gly Phe Ser Gly His Met
                675                 680                 685

<210> SEQ ID NO 31
<211> LENGTH: 684
<212> TYPE: PRT
<213> ORGANISM: Zea mays

<400> SEQUENCE: 31

Met Ala Ala Ala Glu Ala Arg Gly Ala Asp Phe Pro Val Gly Met Lys
1               5                   10                  15

Val Leu Val Val Asp Asp Pro Thr Cys Leu Val Val Leu Lys Arg
                20                  25                  30

Met Leu Leu Glu Cys Arg Tyr Asp Val Thr Thr Cys Pro Gln Ala Thr
            35                  40                  45

Arg Ala Leu Thr Met Leu Arg Glu Asn Arg Arg Gly Phe Asp Val Ile
        50                  55                  60

Ile Ser Asp Val His Met Pro Asp Met Asp Gly Phe Arg Leu Leu Glu
65                  70                  75                  80

Leu Val Gly Leu Glu Met Asp Leu Pro Val Ile Met Met Ser Ala Asp
                85                  90                  95

Ser Arg Thr Asp Ile Val Met Lys Gly Ile Lys His Gly Ala Cys Asp
                100                 105                 110

Tyr Leu Ile Lys Pro Val Arg Met Glu Glu Leu Lys Asn Ile Trp Gln
            115                 120                 125

His Val Val Arg Lys Lys Phe Asn Gly Asn Lys Asp His Glu His Ser
        130                 135                 140

Gly Ser Leu Asp Asp Thr Asp Arg Asn Arg Pro Thr Asn Asn Asp Asn
145                 150                 155                 160

Glu Tyr Ala Ser Ser Ala Asn Asp Gly Gly Asp Gly Ser Trp Lys Ser
                165                 170                 175

Gln Lys Lys Lys Arg Glu Lys Glu Asp Asp Glu Thr Asp Leu Glu Ser
                180                 185                 190

Gly Asp Pro Ser Thr Ser Lys Lys Pro Arg Val Val Trp Ser Val Glu
            195                 200                 205

Leu His Gln Gln Phe Val Asn Ala Val Asn His Leu Gly Ile Asp Lys
        210                 215                 220

Ala Val Pro Lys Lys Ile Leu Glu Leu Met Asn Val Pro Gly Leu Thr
225                 230                 235                 240

Arg Glu Asn Val Ala Ser His Leu Gln Lys Phe Arg Leu Tyr Leu Lys
                245                 250                 255
```

```
Arg Ile Ala Gln His His Ala Gly Ile Pro His Pro Phe Val Ala Ser
            260                 265                 270

Ala Ser Ser Ala Lys Val Ala Pro Leu Gly Gly Leu Glu Phe Gln Ala
        275                 280                 285

Leu Ala Ala Ser Gly Gln Ile Pro Pro Gln Ala Leu Ala Ala Leu Gln
    290                 295                 300

Asp Glu Leu Leu Gly Arg Pro Thr Ser Ser Leu Ala Leu Pro Gly Arg
305                 310                 315                 320

Asp Gln Ser Ser Leu Arg Leu Ala Ala Ile Lys Gly Asn Lys Pro His
                325                 330                 335

Gly Glu Arg Glu Ile Ala Phe Gly Gln Pro Ile Tyr Lys Cys Gln Asn
            340                 345                 350

Asn Thr Tyr Gly Ala Phe Ser Gln Ser Ser Pro Ala Val Gly Gly Leu
        355                 360                 365

Pro Ser Phe Ala Ala Trp Pro Asn Asn Lys Leu Gly Met Thr Asp Ser
    370                 375                 380

Ser Asn Thr Leu Gly Asn Val Gly Asn Ser Gln Asn Ser Asn Met Leu
385                 390                 395                 400

Leu His Glu Leu Gln Gln Gln Pro Asp Thr Leu Leu Ser Gly Thr Leu
                405                 410                 415

His Asn Ile Asp Val Lys Pro Ser Gly Val Val Met Pro Ser Gln Ser
            420                 425                 430

Leu Asn Val Phe Pro Ala Ser Glu Gly Ile Ser His Asn Gln Asn Pro
        435                 440                 445

Leu Val Ile Pro Ser Gln Ser Pro Ser Phe Leu Ala Ser Val Pro Pro
    450                 455                 460

Ser Met Lys His Glu Ser Leu Leu Gly Ser Pro Ser Pro Ser Thr Ser
465                 470                 475                 480

Leu Leu Gly Gly Leu Asp Met Val Asn Gln Ala Ser Thr Ser Gln Pro
                485                 490                 495

Leu Ile Ser Ser His Gly Ala Asn Leu Pro Gly Leu Met Asn Arg Ser
            500                 505                 510

Ser Asn Ala Met Pro Ser Pro Gly Ile Ser Asn Phe Gln Ser Gly Asn
        515                 520                 525

Ile Pro Tyr Val Val Asn Gln Asn Ala Met Gly Val Ser Ser Arg Pro
    530                 535                 540

Pro Gly Val Leu Lys Thr Glu Cys Thr Glu Ser Leu Thr His Ser Tyr
545                 550                 555                 560

Gly Tyr Ile Gly Gly Ser Thr Ser Val Asp Ser Ser Leu Leu Ser Ser
                565                 570                 575

Gln Ala Lys Asn Pro Gln Tyr Gly Leu Leu Gln Ser Gln Asn Asp Val
            580                 585                 590

Ser Ser Ser Trp Leu Ser Ser Gln Asp Phe Asp Ser Phe Gly Asn Ser
        595                 600                 605

Leu Gly Gln Gly His Pro Gly Ser Thr Ser Ser Asn Phe Gln Ser Ser
    610                 615                 620

Ala Leu Gly Lys Leu Pro Asp Gln Gly Arg Gly Arg Asn His Gly Phe
625                 630                 635                 640

Val Gly Lys Gly Thr Cys Ile Pro Ser Arg Phe Ala Val Asp Glu Val
                645                 650                 655

Glu Ser Pro Thr Asn Leu Ser His Asn Ile Val Asn Ser Gly Asp Ile
            660                 665                 670

Val Asn Pro Asp Ile Phe Gly Phe Ser Gly Gln Met
```

<210> SEQ ID NO 32
<211> LENGTH: 631
<212> TYPE: PRT
<213> ORGANISM: Zea mays

<400> SEQUENCE: 32

```
Met Thr Val Asp Glu Leu Lys Leu Gln Ala Arg Ala Ser Gly Gly His
1               5                   10                  15
Gly Ala Lys Asp Gln Phe Pro Val Gly Met Arg Val Leu Ala Val Asp
            20                  25                  30
Asp Asp Pro Thr Cys Leu Lys Ile Leu Glu Asn Leu Leu Leu Arg Cys
        35                  40                  45
Gln Tyr His Val Thr Thr Thr Gly Gln Ala Ala Thr Ala Leu Lys Leu
    50                  55                  60
Leu Arg Glu Lys Lys Asp Gln Phe Asp Leu Val Ile Ser Asp Val His
65                  70                  75                  80
Met Pro Asp Met Asp Gly Phe Lys Leu Leu Glu Leu Val Gly Leu Glu
                85                  90                  95
Met Asp Leu Pro Val Ile Met Leu Ser Ala Asn Gly Glu Thr Gln Thr
            100                 105                 110
Val Met Lys Gly Ile Thr His Gly Ala Cys Asp Tyr Leu Leu Lys Pro
        115                 120                 125
Val Arg Ile Glu Gln Leu Arg Thr Ile Trp Gln His Val Val Arg Arg
    130                 135                 140
Arg Ser Cys Asp Ala Lys Asn Ser Gly Asn Asp Asn Asp Ser Gly
145                 150                 155                 160
Lys Lys Leu Gln Val Val Ser Val Glu Gly Asp Asn Gly Val Asn
                165                 170                 175
Arg Asn Lys Arg Ile Ser Arg Lys Gly Arg Asp Asp Asn Gly Asp Asp
            180                 185                 190
Gly Asp Asp Ser Asp Asp Asn Ser Asn Glu Asn Gly Asp Ser Ser Ser
        195                 200                 205
Gln Lys Lys Pro Arg Val Val Trp Ser Val Glu Leu His Arg Lys Phe
    210                 215                 220
Val Ala Ala Val Asn Gln Leu Gly Ile Asp Lys Ala Val Pro Lys Lys
225                 230                 235                 240
Ile Leu Asp Leu Met Asn Val Glu Asn Ile Thr Arg Glu Asn Val Ala
                245                 250                 255
Ser His Leu Gln Lys Tyr Arg Leu Tyr Leu Lys Arg Leu Ser Ala Asp
            260                 265                 270
Ala Ser Arg Gln Ala Asn Leu Thr Ala Ala Phe Gly Gly Arg Asn Pro
        275                 280                 285
Ala Tyr Val Asn Met Gly Leu Asp Ala Phe Arg Gln Tyr Asn Ala Tyr
    290                 295                 300
Gly Arg Tyr Arg Pro Val Pro Thr Thr Asn His Ser Gln Pro Asn Asn
305                 310                 315                 320
Leu Leu Ala Arg Met Asn Ser Pro Ala Phe Gly Met His Gly Leu Leu
                325                 330                 335
Pro Ser Gln Pro Leu Gln Ile Gly His Asn Gln Asn Leu Asn Thr
            340                 345                 350
Ser Leu Gly Asn Val Gly Gly Met Asn Asn Gly Asn Leu Ile Arg Gly
        355                 360                 365
```

```
Ala His Met Pro Leu Gln Asp Thr Ser Lys Cys Phe Pro Thr Gly Pro
    370                 375                 380

Ser Gly Asn Ser Phe Ala Asn Ile Ser Asn Ser Thr Gln Leu Val Thr
385                 390                 395                 400

Thr Asn Asn Leu Pro Leu Gln Ser Leu Glu Pro Ser Asn Gln Gln His
                405                 410                 415

Leu Gly Arg Leu His Ser Ser Ala Asp Pro Phe Asn Ser Phe Val Gly
            420                 425                 430

Glu Pro Pro Gln Phe Ala Asp Leu Gly Arg Cys Asn Thr Thr Trp Pro
        435                 440                 445

Thr Ala Val Ser Ser Asn Val Gln Glu Ile Gly Gln Lys Asp Arg
    450                 455                 460

Ile Val Asn Arg Pro Lys Leu Glu Pro Leu Ser Ser Phe Thr Glu Ala
465                 470                 475                 480

Ser Ser Gln Ile Pro Leu Leu Gly Asn Glu Met Gln Ser His Gln Val
                485                 490                 495

Ala Ser Leu Ala Ser Asn Gly Leu Pro Met Pro Phe Thr Gln Glu Ala
            500                 505                 510

Val Pro Phe Ala Tyr Gly Ser Ser Thr Asn Ser Arg Glu Met Leu Asn
        515                 520                 525

Asn Asn Leu Ala Leu Ser Asn Ser Gly Val Asn Ser Thr Leu Pro Asn
    530                 535                 540

Leu Arg Ile Asp Gly Ser Val Val Pro Gly Gln Thr Leu Gly Gly Ser
545                 550                 555                 560

Asn Ser Gly Gly Cys Val Val Pro Pro Leu Gln Asp Gly Arg Ile Asp
                565                 570                 575

His Gln Ala Val Ser Ser His Leu Asn Tyr Ser Asn Glu Leu Met Gly
            580                 585                 590

Thr Ser Arg Leu Gln Arg Gly Leu Ser Gly Gly Leu Asp Asp Ile Val
        595                 600                 605

Val Asp Met Phe Arg Pro Asp Arg Ala Asp Gly Val Pro Phe Ile
    610                 615                 620

Asp Gly Asp Trp Glu Leu Val
625                 630

<210> SEQ ID NO 33
<211> LENGTH: 643
<212> TYPE: PRT
<213> ORGANISM: Catharanthus roseus

<400> SEQUENCE: 33

Met Asn Leu Gly Gly Gly Gln Leu Val Lys Ser Met Ala Val Pro Ser
1               5                   10                  15

Ser Ser Ala Ser Trp Lys Ser Gly Gly Asp Gly Val Ser Asp Gln Phe
            20                  25                  30

Pro Ala Gly Leu Arg Val Leu Val Asp Asp Pro Thr Cys Leu
        35                  40                  45

Arg Ile Leu Glu Lys Met Leu Lys Asn Cys Leu Tyr Glu Val Thr Lys
    50                  55                  60

Cys Asn Arg Ala Glu Ile Ala Leu Lys Leu Leu Arg Asp Asn Arg Asn
65                  70                  75                  80

Gly Tyr Asp Ile Val Ile Ser Asp Val His Met Pro Asp Met Asp Gly
                85                  90                  95

Phe Lys Leu Leu Glu Gln Val Gly Leu Glu Met Asp Leu Pro Val Ile
            100                 105                 110
```

```
Met Met Ser Ala Asp Asp Ser Lys Asn Val Val Met Lys Gly Val Thr
        115                 120                 125
His Gly Ala Cys Asp Tyr Leu Ile Lys Pro Val Arg Ile Glu Ala Leu
    130                 135                 140
Lys Asn Ile Trp Gln His Val Arg Lys Gly Lys His Glu Trp Lys
145                 150                 155                 160
Glu Lys Asp Tyr Glu Gln Ser Gly Ser Val Glu Asp Gly Glu Arg Gln
                165                 170                 175
Gln Lys Pro Asn Glu Asp Val Asp Tyr Ser Ser Ala Asn Glu Gly
            180                 185                 190
Asn Trp Lys Asn Ser Lys Lys Arg Lys Asp Asp Glu Asp Gln Glu
        195                 200                 205
Glu Lys Asp Asp Ser Ser Thr Leu Lys Lys Pro Arg Val Val Trp Ser
    210                 215                 220
Val Glu Leu His Gln Gln Phe Val Ala Val Asn Gln Leu Gly Ile
225                 230                 235                 240
Asp Lys Ala Val Pro Lys Lys Ile Leu Glu Leu Met Asn Val Pro Gly
            245                 250                 255
Leu Thr Arg Glu Asn Val Ala Ser His Leu Gln Lys Tyr Arg Leu Tyr
        260                 265                 270
Leu Arg Arg Val Ser Gly Val Ser Gln His Gln Asn Gly Leu Asn Asn
    275                 280                 285
Ser Phe Met Gly Thr Pro Asp Ala Thr Phe Gly Met Ser Ser Ile
        290                 295                 300
Asn Gly Leu Asp Phe Gln Ala Leu Ala Ala Thr Gly Gln Ile Pro Ala
305                 310                 315                 320
Gln Ser Leu Ala Ser Leu Gln Ala Ala Ile Gly Arg Pro Thr Ser
            325                 330                 335
Lys Pro Thr Ile Ser Met Pro Val Val Asp Gln Arg Asn Leu Phe Ser
        340                 345                 350
Phe Glu Pro His Lys Leu Arg Phe Gly Glu Gly Gln Gln Leu Asn
    355                 360                 365
Gly Ser Thr Lys Gln Ile Ser Leu Leu His Gly Ile Pro Thr Asn Met
        370                 375                 380
Glu Pro Lys Gln Leu Ala Ser Leu Asn Gln Ser Ala Gln Thr Phe Gly
385                 390                 395                 400
Gly Ile Asn Met Gln Val Ser Ser Gln Ala Ser Gln Gly Asn Thr Leu
                405                 410                 415
Leu Met Gln Met Thr Gln Pro Met Ser Arg Ala Pro Met Leu Asn Glu
            420                 425                 430
Asn Asn Ala Ser Gln Ile Ser Arg Leu Pro Ser Ser Val Gly Gln Ala
        435                 440                 445
Ile Leu Ser Asn Gly Ile Pro Ser Gly Val Leu Gly Arg Asn Gly Ile
    450                 455                 460
Val Asp Ser Val Arg Gly Pro Val Tyr Thr Pro Val Ser Gln Thr Ser
465                 470                 475                 480
Ser Leu Val Asp Phe Ser Val Ser Asn Ser Ala Glu Leu Pro Gly Ser
            485                 490                 495
Thr Phe Pro His Ala Ser Asn Ser Gly Ile Ser Ser Leu Thr Pro Lys
        500                 505                 510
Gly Met Met Gln Glu Glu Val Asn Ser Glu Gly Lys Gly Ser Arg Gly
            515                 520                 525
```

```
Phe Pro Ser Ser Tyr Asp Ile Phe Ser Glu Leu Gln Gln His Lys Thr
    530                 535                 540

Gln Asp Trp Gly Leu Gln Asn Val Gly Ser Thr Phe Asp Gly Thr Gln
545                 550                 555                 560

His Ser Ser Ile Gln Gly Ser Leu Glu Gly Gly Arg Asn Asn Pro Pro
                565                 570                 575

Asn Phe Gly Gln Gln Phe Ser Ser Tyr Met Val Asp Asn Ser Leu Arg
            580                 585                 590

Ile Lys Ser Glu Arg His Pro Asp Ala Asn Cys Gln Thr Asn Leu Phe
        595                 600                 605

Pro Gln Leu Phe Gly Gln Asp Asp Leu Met Ser Ala Leu Leu Lys Gln
    610                 615                 620

Glu Gly Ile Gly Ser Val Glu Ser Asp Phe Gly Phe Asp Gly Tyr Ala
625                 630                 635                 640

Leu Asp Leu

<210> SEQ ID NO 34
<211> LENGTH: 370
<212> TYPE: PRT
<213> ORGANISM: Medicago truncatula

<400> SEQUENCE: 34

Ser Ile Ser Thr Val Thr Ser Thr Ala Thr Thr Met Lys Ser Gly Glu
1               5                   10                  15

Gly Ser Asp Gln Phe Pro Ala Gly Leu Arg Val Leu Val Asp Asp
            20                  25                  30

Asp Pro Thr Cys Leu Met Ile Leu Glu Lys Met Leu Arg Thr Cys Leu
            35                  40                  45

Tyr Glu Val Thr Lys Cys Asn Arg Ala Glu Thr Ala Leu Ser Leu Leu
    50                  55                  60

Arg Glu Asn Lys Asn Gly Phe Asp Ile Val Ile Ser Asp Val His Met
65                  70                  75                  80

Pro Asp Met Asp Gly Phe Lys Leu Leu Glu Leu Asp Trp Lys Trp Thr
                85                  90                  95

Phe Gln Leu Leu Glu Ser Thr Thr Val Asp Val Ile Val Leu Glu Val
            100                 105                 110

Ser Gln Thr Val Asp Gly Phe Lys Leu Leu Glu His Ile Gly Leu Glu
        115                 120                 125

Met Asp Leu Pro Val Ile Met Met Ser Ala Asp Gly Lys Ser Val
    130                 135                 140

Val Met Lys Gly Val Thr His Gly Ala Cys Asp Tyr Leu Ile Lys Pro
145                 150                 155                 160

Val Arg Ile Glu Ala Leu Lys Asn Ile Trp Gln His Val Arg Lys
                165                 170                 175

Lys Lys Asn Glu Trp Lys Asp Thr Glu Gln Ser Gly Ser Ala Asp Glu
            180                 185                 190

Gly Asp Arg His Pro Lys Ala Ser Asp Ala Asp Tyr Ser Ser Ser
        195                 200                 205

Ala Asn Glu Gly Asn Trp Arg Asn Ser Arg Lys Arg Arg Asp Glu
    210                 215                 220

Glu Glu Gly Asp Asp Arg Asp Asp Ser Ser Thr Leu Lys Lys Pro Arg
225                 230                 235                 240

Val Val Trp Ser Val Glu Leu His Gln Gln Phe Val Ala Ala Val Asp
                245                 250                 255
```

Gln Leu Gly Ile Asp Lys Ala Val Pro Lys Lys Ile Leu Glu Leu Met
                260                 265                 270

Asn Val Pro Gly Leu Thr Arg Glu Asn Val Ala Ser His Leu Gln Lys
            275                 280                 285

Tyr Arg Leu Tyr Leu Arg Arg Leu Ser Gly Val Ser Gln His Gln Asn
        290                 295                 300

Asn Ser Phe Leu Ser Pro Gln Glu Ala Ser Phe Gly Thr Ile Ser Ser
305                 310                 315                 320

Met Asn Gly Leu Asp Leu Gln Thr Leu Ala Ala Gly Gln Leu Pro
                325                 330                 335

Ala Gln Ser Leu Ala Thr Leu Gln Ala Ala Gly Leu Gly Arg Ser Thr
                340                 345                 350

Val Lys Ser Gly Leu Pro Met Pro Leu Met Glu Ser Arg Leu Phe Ser
                355                 360                 365

Phe Glu
    370

<210> SEQ ID NO 35
<211> LENGTH: 226
<212> TYPE: PRT
<213> ORGANISM: Poncirus trifoliata

<400> SEQUENCE: 35

Val Ser Asp Gln Phe Pro Ala Gly Leu Arg Val Leu Val Asp Asp
1               5                   10                  15

Asp Pro Thr Cys Leu Arg Ile Leu Glu Lys Met Leu Gly Thr Cys Leu
                20                  25                  30

Tyr Glu Val Thr Lys Cys Asn Arg Ala Glu Ile Ala Leu Asp Met Leu
            35                  40                  45

Arg Thr Asn Lys Asn Gly Tyr Asp Ile Val Ile Ser Glu Val His Met
50                  55                  60

Pro Asp Met Asp Gly Phe Lys Leu Leu Glu Gln Val Gly Leu Glu Met
65                  70                  75                  80

Asp Leu Pro Val Ile Met Met Ser Ala Asp Asp Ser Lys Gln Val Val
                85                  90                  95

Met Lys Gly Val Thr His Gly Ala Cys Asn Tyr Leu Lys Pro Val Arg
                100                 105                 110

Ile Glu Ala Leu Lys Lys Ile Trp Gln His Val Val Arg Lys Arg Lys
            115                 120                 125

Asn Glu Trp Lys Asp Leu Glu Gln Ser Arg Ser Val Glu Glu Gly Asp
130                 135                 140

Arg Gln Pro Lys Pro Ser Glu Glu Ala Asp Tyr Ser Ser Ser Ala Asn
145                 150                 155                 160

Glu Gly Asn Trp Arg Thr Ser Lys Arg Arg Lys Asp Glu Glu Glu
                165                 170                 175

Met Glu Glu Arg Asp Asp Thr Ser Thr Leu Lys Lys Pro Arg Val Val
                180                 185                 190

Trp Ser Val Glu Leu His Gln Gln Phe Val Ser Ala Val Asn Gln Leu
            195                 200                 205

Gly Ile Asp Lys Ala Val Pro Lys Lys Ile Leu Glu Leu Met Asn Val
        210                 215                 220

Pro Gly
225

<210> SEQ ID NO 36

```
<211> LENGTH: 216
<212> TYPE: PRT
<213> ORGANISM: Vitis vinifera

<400> SEQUENCE: 36

Ala Ser Ser Ser Gly Ala Arg Lys Ala Gly Asp Val Val Pro Asp Gln
1               5                   10                  15

Phe Pro Ala Gly Leu Arg Val Leu Val Val Asp Asp Pro Thr Cys
            20                  25                  30

Leu Met Ile Leu Glu Lys Met Leu Arg Thr Cys Leu Tyr Glu Val Thr
        35                  40                  45

Lys Cys Asn Arg Ala Glu Thr Ala Leu Ser Leu Leu Arg Gly Asn Lys
    50                  55                  60

Ser Gly Phe Asp Ile Val Ile Ser Asp Val His Met Pro Asp Met Asp
65                  70                  75                  80

Gly Phe Lys Leu Leu Glu His Ile Gly Leu Glu Met Asp Leu Pro Val
                85                  90                  95

Ile Met Met Ser Ala Asp Asp Gly Lys His Val Val Met Lys Gly Val
            100                 105                 110

Thr His Gly Ala Cys Asp Tyr Leu Ile Lys Pro Val Arg Ile Glu Ala
        115                 120                 125

Leu Lys Asn Ile Trp Gln His Val Val Arg Lys Arg Lys Asn Glu Trp
    130                 135                 140

Lys Asp Leu Glu Gln Ser Gly Ser Val Glu Asp Gly Asp Arg Gln Gln
145                 150                 155                 160

Lys Pro Ser Glu Asp Val Asp Tyr Ser Ser Ala Asn Glu Gly Asn
                165                 170                 175

Trp Lys Asn Ser Lys Arg Arg Lys Asp Glu Glu Asp Ala Glu Glu
            180                 185                 190

Arg Asp Asp Thr Ser Thr Leu Lys Lys Pro Arg Val Val Trp Ser Val
        195                 200                 205

Glu Leu His Gln Gln Phe Val Ala
    210                 215

<210> SEQ ID NO 37
<211> LENGTH: 288
<212> TYPE: PRT
<213> ORGANISM: Medicago truncatula

<400> SEQUENCE: 37

Leu Lys Ser Arg Glu Arg Lys Met Val Asp Ser Gly Asp Arg Phe Pro
1               5                   10                  15

Ile Gly Met Arg Val Leu Ala Val Asp Asp Asp Pro Thr Cys Leu Leu
            20                  25                  30

Val Leu Glu Thr Leu Leu Arg Arg Cys Gln Tyr His Val Thr Thr Thr
        35                  40                  45

Ser Gln Ala Ile Thr Ala Leu Thr Met Leu Arg Glu Asn Lys Asp Lys
    50                  55                  60

Phe Asp Leu Val Ile Ser Asp Val His Met Pro Asp Met Asp Gly Phe
65                  70                  75                  80

Lys Leu Leu Glu Leu Val Gly Leu Glu Met Asp Leu Pro Val Ile Met
                85                  90                  95

Leu Ser Ala Tyr Gly Asp Thr Lys Leu Val Met Lys Gly Ile Ser His
            100                 105                 110

Gly Ala Cys Asp Tyr Leu Leu Lys Pro Val Arg Leu Glu Glu Leu Lys
        115                 120                 125
```

```
Asn Ile Trp Gln His Val Ile Arg Lys Lys Ser Asp Pro Lys Glu
        130                 135                 140

Lys Asn Lys Thr Ser Lys Pro Asp Lys Thr Thr Ser Asp Ser Gly Ser
145                 150                 155                 160

Gly Leu Arg Ser Ala Gly Ala Glu Asn Ser Asp Glu Asn Gly Lys Leu
                165                 170                 175

Thr Lys Lys Arg Lys Asp Gln Asp Glu Asp Glu Asp Glu Asp Lys Glu
                180                 185                 190

Asn Gly Asn Asp Asn Glu Asp Pro Ser Ala Gln Lys Lys Pro Arg Val
                195                 200                 205

Val Trp Ser Val Glu Leu His Arg Lys Phe Val Ala Ala Val Asn Gln
        210                 215                 220

Leu Gly Ile Asp Lys Ala Val Pro Lys Lys Ile Leu Asp Met Met Asn
225                 230                 235                 240

Val Glu Asn Ile Thr Arg Glu Asn Val Ala Ser His Leu Gln Lys Tyr
                245                 250                 255

Arg Leu Tyr Leu Lys Arg Ile Ser Cys Val Ala Asn Gln Gln Ala Ser
                260                 265                 270

Met Val Ala Ala Leu Gly Ser Ala Asp Gln Ser Tyr Leu Arg Met Gly
                275                 280                 285
```

<210> SEQ ID NO 38
<211> LENGTH: 206
<212> TYPE: PRT
<213> ORGANISM: Brassica rapa

<400> SEQUENCE: 38

```
Asn Ile Trp Gln His Val Val Arg Lys Arg Arg Ser Glu Trp Ser Val
1               5                   10                  15

Pro Glu His Ser Gly Ser Ile Glu Glu Thr Gly Gln Gln His His Gln
                20                  25                  30

Gln Arg Gly Pro Ala Val Ser Glu Asp Ala Ala Asp Asn Ala Ser
                35                  40                  45

Ser Val Asn Asn Glu Gly Asn Asn Trp Arg Ser Ser Asn Asn Ser
    50                  55                  60

Arg Lys Arg Lys Glu Glu Glu Gly Asp Glu Gln Gly Asp Glu Asp Ala
65                  70                  75                  80

Ser Asn Leu Lys Lys Pro Arg Val Val Trp Ser Val Glu Leu His Gln
                85                  90                  95

Gln Phe Val Ala Ala Val Asn Gln Leu Gly Val Glu Lys Ala Val Pro
                100                 105                 110

Lys Lys Ile Leu Glu Leu Met Asn Val Pro Gly Leu Thr Arg Glu Asn
                115                 120                 125

Val Ala Ser His Leu Gln Lys Tyr Arg Ile Tyr Leu Arg Arg Leu Gly
        130                 135                 140

Gly Val Ser Gln His Gln Gly Asn Leu Asn Ser Phe Met Thr Gly
145                 150                 155                 160

Gln Asp Ala Ser Phe Gly Pro Leu Ser Ser Leu Asn Gly Phe Asp Leu
                165                 170                 175

Gln Ala Leu Ala Val Thr Gly Gln Leu Pro Ala Gln Ser Leu Ala Gln
                180                 185                 190

Leu Gln Ala Ala Gly Leu Gly Arg Ala Met Val Ser Lys Ser
        195                 200                 205
```

-continued

```
<210> SEQ ID NO 39
<211> LENGTH: 206
<212> TYPE: PRT
<213> ORGANISM: Brassica rapa

<400> SEQUENCE: 39

Asn Ile Trp Gln His Val Val Arg Lys Arg Arg Ser Glu Trp Ser Val
1               5                   10                  15

Pro Glu His Ser Gly Ser Ile Glu Glu Thr Gly Gln Gln His His Gln
            20                  25                  30

Gln Arg Gly Pro Ala Val Ser Glu Asp Ala Ala Asp Asn Ala Ser
        35                  40                  45

Ser Val Asn Asn Glu Gly Asn Asn Trp Arg Ser Ser Asn Asn Ser
50                  55                  60

Arg Lys Arg Lys Glu Glu Gly Asp Glu Gln Gly Asp Glu Asp Ala
65                  70                  75                  80

Ser Asn Leu Lys Lys Pro Arg Val Val Trp Ser Val Glu Leu His Gln
                85                  90                  95

Gln Phe Val Ala Ala Val Asn Gln Leu Gly Val Glu Lys Ala Val Pro
            100                 105                 110

Lys Lys Ile Leu Glu Leu Met Asn Val Pro Gly Leu Thr Arg Glu Asn
        115                 120                 125

Val Ala Ser His Leu Gln Lys Tyr Arg Ile Tyr Leu Arg Arg Leu Gly
130                 135                 140

Gly Val Ser Gln His Gln Gly Asn Leu Asn Asn Ser Phe Met Thr Gly
145                 150                 155                 160

Gln Asp Ala Ser Phe Gly Pro Leu Ser Ser Leu Asn Gly Phe Asp Leu
                165                 170                 175

Gln Ala Leu Ala Val Thr Gly Gln Leu Pro Ala Gln Ser Leu Ala Gln
            180                 185                 190

Leu Gln Ala Ala Gly Leu Gly Arg Ala Met Val Ser Lys Ser
        195                 200                 205

<210> SEQ ID NO 40
<211> LENGTH: 348
<212> TYPE: PRT
<213> ORGANISM: vitis shuttleworthii

<400> SEQUENCE: 40

Ser Asp Val His Met Pro Asp Met Asp Gly Tyr Lys Leu Leu Glu His
1               5                   10                  15

Val Gly Leu Glu Met Asp Leu Pro Val Ile Met Met Ser Ala Asp Gly
            20                  25                  30

Arg Thr Ser Ala Val Met Arg Gly Ile Arg His Gly Ala Cys Asp Tyr
        35                  40                  45

Leu Ile Lys Pro Ile Arg Glu Glu Glu Leu Lys Asn Ile Trp Gln His
    50                  55                  60

Val Val Arg Lys Lys Trp Asn Glu Asn Lys Glu His Glu His Ser Gly
65                  70                  75                  80

Ser Leu Glu Asp Asn Asp Arg His Lys Arg Gly Gly Glu Asp Ala Glu
                85                  90                  95

Tyr Ala Ser Ser Val Asn Glu Gly Ala Glu Gly Ile Leu Lys Gly Gln
            100                 105                 110

Lys Lys Arg Arg Asp Ser Lys Asp Glu Asp Asp Gly Glu Leu Glu Asn
        115                 120                 125

Glu Asp Pro Ser Thr Ser Lys Lys Pro Arg Val Val Trp Ser Val Glu
```

```
                130                 135                 140
Leu His Gln Gln Phe Val Ser Ala Val Asn Gln Leu Gly Ile Asp Lys
145                 150                 155                 160

Ala Val Pro Lys Arg Ile Leu Glu Leu Met Asn Val Pro Gly Leu Thr
                165                 170                 175

Arg Glu Asn Val Ala Ser His Leu Gln Lys Phe Arg Leu Tyr Leu Lys
                180                 185                 190

Arg Leu Ser Gly Val Ala Gln Gln Gly Gly Ile Pro Asn Ser Phe
                195                 200                 205

Cys Gly Pro Val Glu Pro Asn Val Lys Leu Gly Ser Leu Gly Arg Phe
            210                 215                 220

Asp Ile Gln Ala Leu Ala Ala Ser Gly Gln Ile Pro Pro Gln Thr Leu
225                 230                 235                 240

Ala Ala Leu Gln Ala Glu Leu Leu Gly Arg Pro Thr Ser Asn Leu Val
                245                 250                 255

Leu Pro Ala Met Asp Gln Pro Ala Leu Leu Gln Ala Ser Leu Gln Gly
                260                 265                 270

Pro Lys Cys Ile Pro Val Glu His Gly Val Ala Phe Gly Gln Pro Leu
            275                 280                 285

Val Lys Cys Gln Thr Asn Ile Ser Lys His Phe Pro Pro Thr Val Val
            290                 295                 300

Ser Thr Glu Asp Val Pro Ser Gly Phe Gly Ala Trp Pro Ser Asn Ser
305                 310                 315                 320

Leu Gly Thr Val Gly Thr Ser Gly Ser Leu Gly Arg Leu Ser Ala Gln
                325                 330                 335

Asn Asn Asn Ile Leu Met Asp Met Leu His Gln Gln
                340                 345

<210> SEQ ID NO 41
<211> LENGTH: 228
<212> TYPE: PRT
<213> ORGANISM: Allium cepa
<220> FEATURE:
<221> NAME/KEY: misc_feature
<222> LOCATION: (214)..(214)
<223> OTHER INFORMATION: Xaa can be any naturally occurring amino acid

<400> SEQUENCE: 41

Phe Pro Ile Gly Leu Arg Val Leu Val Asp Asp Val Thr Cys
1               5                   10                  15

Leu Lys Ile Leu Asp Gln Met Leu Gln Lys Cys Lys Tyr Arg Val Thr
                20                  25                  30

Thr Cys Ser Gln Ala Thr Val Ala Leu Ser Leu Leu Arg Glu Arg Arg
            35                  40                  45

Asp Ser Phe Asp Val Val Ile Ser Asp Val His Met Pro Asp Met Asn
50                  55                  60

Gly Phe Lys Leu Leu Glu Leu Val Gly Leu Glu Met Asp Leu Pro Val
65                  70                  75                  80

Ile Met Met Ser Ala Asp Gly Gly Thr Gln Thr Val Met Arg Gly Ile
                85                  90                  95

Lys His Gly Ala Cys Asp Tyr Leu Ile Lys Pro Val Arg Met Glu Glu
            100                 105                 110

Leu Lys Asn Ile Trp Gln His Val Ile Arg Lys Cys Asn Gly His
                115                 120                 125

Arg Asn Met Glu His Ser Gly Ser Met Asp Asp Ser Asp Arg Ser Arg
130                 135                 140
```

```
Arg Val Ala Asp Asp Ala Asp Ala Ala Ser Leu Val Asn Asp Gly Asn
145                 150                 155                 160

Asp Gly Ser Trp Lys Ser Arg Asn Lys Arg Lys Glu Ser Lys Glu Asp
            165                 170                 175

Glu Asp Asp Gly Glu Leu Asp His Glu Asp His Ser Ser Lys Lys Pro
            180                 185                 190

Arg Val Val Trp Ser Val Glu Leu His Gln Gln Phe Val Ser Ala Val
            195                 200                 205

Ser Gln Leu Gly Ile Xaa Lys Ala Val Pro Lys Arg Ile Glu Leu Met
            210                 215                 220

Asn Val Pro Gly
225

<210> SEQ ID NO 42
<211> LENGTH: 310
<212> TYPE: PRT
<213> ORGANISM: Phaseolus vulgaris

<400> SEQUENCE: 42

Arg Asp Asp Thr Ser Thr Leu Lys Lys Pro Arg Val Val Trp Ser Val
1               5                   10                  15

Glu Leu His Gln Gln Phe Val Ala Ala Val Asp Gln Leu Gly Ile Asp
            20                  25                  30

Lys Ala Val Pro Lys Lys Ile Leu Glu Leu Met Asn Val Pro Gly Leu
            35                  40                  45

Thr Arg Glu Asn Val Ala Ser His Leu Gln Lys Tyr Arg Leu Tyr Leu
50                  55                  60

Arg Arg Leu Ser Gly Val Ser Gln His Gln Asn Asn Leu Asn Asn Ser
65                  70                  75                  80

Phe Leu Gly Ser Gln Glu Ala Thr Phe Gly Thr Ile Ser Ser Ile Asn
            85                  90                  95

Gly Ile Asp Leu Gln Thr Leu Ala Val Thr Gly Gln Leu Pro Ala Gln
            100                 105                 110

Ser Leu Ala Thr Leu Gln Ala Ala Gly Leu Gly Arg Ser Thr Ala Lys
            115                 120                 125

Thr Gly Val Pro Met Pro Leu Met Asp Gln Arg Asn Leu Phe Ser Phe
130                 135                 140

Glu Asn Pro Arg Val Arg Phe Gly Glu Gly Gln Gln His Leu Ser
145                 150                 155                 160

Ser Ser Lys Pro Met Asn Leu Leu Leu Gly Ile Pro Thr Asn Met Glu
            165                 170                 175

Pro Lys Gln Leu Ala Asn Leu His Gln Ser Thr Gln Ser Ile Ala Ser
            180                 185                 190

Leu Asn Met Arg Val Asn Ala Ser Ala Thr Gln Gly Asn Pro Leu Met
            195                 200                 205

Met Gln Met Pro Gln Ser Gln Pro Arg Gly Gln Met Leu Ser Glu Asn
            210                 215                 220

Thr Gly Pro Arg Val Pro Arg Leu Pro Ser Ser Leu Gly Gln Pro Thr
225                 230                 235                 240

Val Ser Asn Gly Ile Ser Asn Gly Phe Leu Gly Arg Asn Gly Ile Ala
            245                 250                 255

Gly Asn Asn Arg Gly Pro Ala Tyr Asn Pro Val Pro Pro Asn Ser Ser
            260                 265                 270

Leu Leu Ser Phe Pro Met Asn Gln Ser Ser Glu Val Ser Val Asn Asn
```

```
                275                 280                 285
Ser Leu Pro Leu Gly Ser Ser Pro Gly Ile Ser Ser Ile Thr Thr Lys
    290                 295                 300

Ser Ser Phe Pro Glu Glu
305             310

<210> SEQ ID NO 43
<211> LENGTH: 217
<212> TYPE: PRT
<213> ORGANISM: citrus clementina
<220> FEATURE:
<221> NAME/KEY: misc_feature
<222> LOCATION: (18)..(18)
<223> OTHER INFORMATION: Xaa can be any naturally occurring amino acid

<400> SEQUENCE: 43

Gln Phe Pro Ala Gly Leu Arg Val Leu Val Asp Asp Ile Thr
1               5                   10                  15

Val Xaa Arg Ile Leu Glu Gln Met Leu Arg Arg Cys Leu Tyr Asn Val
        20                  25                  30

Thr Thr Cys Ser Gln Ala Ala Val Ala Leu Asn Ile Leu Arg Glu Arg
    35                  40                  45

Lys Gly Cys Phe Asp Val Val Leu Ser Asp Val His Met Pro Asp Met
50                  55                  60

Asp Gly Phe Lys Leu Leu Glu His Ile Gly Leu Glu Met Asp Leu Pro
65                  70                  75                  80

Val Ile Met Met Ser Ala Asp Gly Arg Val Ser Ala Val Met Arg Gly
                85                  90                  95

Ile Arg His Gly Ala Cys Asp Tyr Leu Ile Lys Pro Ile Arg Glu Glu
            100                 105                 110

Glu Leu Lys Asn Ile Trp Gln His Val Val Arg Lys Arg Trp Asn Glu
        115                 120                 125

Asn Lys Glu His Glu Asn Ser Gly Ser Leu Glu Glu Thr Asp His His
    130                 135                 140

Lys Arg Gly Ser Asp Glu Ile Glu Tyr Ala Ser Ser Val Asn Glu Gly
145                 150                 155                 160

Thr Glu Gly Thr Phe Lys Ala Gln Arg Lys Arg Ile Ser Ala Lys Glu
                165                 170                 175

Glu Asp Asp Gly Glu Leu Glu Ser Asp Asp Pro Ser Thr Thr Lys Lys
            180                 185                 190

Pro Arg Val Val Trp Ser Val Glu Leu His Gln Gln Phe Val Ser Ala
        195                 200                 205

Val Asn Gln Leu Gly Ile Asp Lys Ala
    210                 215

<210> SEQ ID NO 44
<211> LENGTH: 296
<212> TYPE: PRT
<213> ORGANISM: Solanum tuberosum

<400> SEQUENCE: 44

Ser Val Glu Asp Gly Asp Gln Gln Gln Lys Pro Pro Glu Asp Val Asp
1               5                   10                  15

Tyr Ser Ser Ser Ala Asn Glu Gly Asn Trp Lys Ser Ser Lys Arg Arg
                20                  25                  30

Lys Glu Glu Glu Asp Glu Thr Glu Glu Arg Asp Asp Leu Ser Thr Ser
            35                  40                  45
```

```
Lys Lys Pro Arg Val Val Trp Ser Val Glu Leu His Gln Gln Phe Val
    50                  55                  60
Gln Ala Val Asn Gln Leu Gly Ile Asp Lys Ala Val Pro Lys Lys Ile
65                  70                  75                  80
Leu Glu Leu Met Asn Val Pro Gly Leu Thr Arg Glu Asn Val Ala Ser
                85                  90                  95
His Leu Gln Lys Tyr Arg Leu Tyr Leu Arg Arg Leu Ser Gly Val Ser
                100                 105                 110
Gln His Gln Asn Gly Leu Asn Ser Phe Met Gly His Pro Glu Ala
                115                 120                 125
Thr Tyr Gly Ser Met Thr Ser Phe Asn Gly Leu Glu Leu Gln Ala Leu
    130                 135                 140
Ala Ala Thr Gly Gln Leu Pro Ala Gln Ser Leu Ala Thr Leu Gln Ala
145                 150                 155                 160
Ala Ala Leu Gly Arg Ser Ala Thr Lys Ser Ala Ile Ser Met Pro Leu
                165                 170                 175
Val Asp Gln Arg Asn Leu Phe Ser Phe Glu Asn Pro Lys Leu Arg Phe
                180                 185                 190
Ser Glu Gly Gln Gln Gln Leu Asn Asn Ser Asn Lys Gln Ile Asn Leu
    195                 200                 205
Leu His Gly Ile Pro Thr Thr Met Glu Pro Lys Gln Leu Ala Asp Leu
    210                 215                 220
His Gln Ser Ser Gln Ser Phe Val Ala Met Asn Met Gln Gly Asn Ala
225                 230                 235                 240
Arg Met Gln Gln Asn Asn Ala Leu Leu Met His Met Ser Gln Gln Gln
                245                 250                 255
Gln Gln Ser Ser Arg Ala His Met Leu Asn Glu Thr Asn Asn Gly Gln
            260                 265                 270
Val Ser Arg Pro Pro Leu Ser Met Ser Gln Pro Ala Ala Val Leu Ser
        275                 280                 285
Arg Asn Ser Ile Val Asp Asn Val
        290                 295

<210> SEQ ID NO 45
<211> LENGTH: 227
<212> TYPE: PRT
<213> ORGANISM: Sorghum bicolor

<400> SEQUENCE: 45

Asp Ala Thr Ala Phe Pro Tyr Gly Leu Arg Val Leu Val Val Asp Asp
1               5                   10                  15
Asp Pro Thr Trp Leu Lys Ile Leu Glu Lys Met Leu Arg Lys Cys Ser
                20                  25                  30
Tyr Glu Val Thr Thr Cys Gly Leu Ala Ser Val Ala Leu Gln Ile Leu
                35                  40                  45
Arg Glu Arg Gly Asn Lys Phe Asp Ile Val Ile Ser Asp Val Asn Met
    50                  55                  60
Pro Asp Met Asp Gly Phe Lys Leu Leu Glu Leu Ile Gly Leu Glu Met
65                  70                  75                  80
Asp Leu Pro Val Ile Met Met Ser Ile Asp Gly Glu Thr Ser Arg Val
                85                  90                  95
Met Lys Gly Val Gln His Gly Ala Cys Asp Tyr Leu Leu Lys Pro Val
                100                 105                 110
Arg Met Lys Glu Leu Arg Asn Ile Trp Gln His Val Tyr Arg Lys Lys
                115                 120                 125
```

```
Met His Glu Val Lys Glu Ile Glu Gly Asn Asp Ser Cys Asp Asp Leu
            130                 135                 140

Gln Ile Phe Arg Asn Gly Val Glu Gly Phe Asp Glu Arg Gly Leu Phe
145                 150                 155                 160

Met Arg Ala Asp Ser Asp Thr Met Arg Lys Arg Lys Asp Met Asp Lys
            165                 170                 175

Asp His Ala Asp Gln Asp Ser Ser Asp Gly Ala Thr Val Lys Lys Ala
            180                 185                 190

Arg Val Val Trp Ser Val Asp Leu His Gln Lys Phe Val Asn Ala Val
            195                 200                 205

Asn Gln Ile Gly Phe Asp Lys Val Gly Pro Lys Lys Ile Leu Asp Leu
            210                 215                 220

Met Ser Val
225

<210> SEQ ID NO 46
<211> LENGTH: 439
<212> TYPE: PRT
<213> ORGANISM: Medicago truncatula

<400> SEQUENCE: 46

Glu Ala Val Pro Lys Lys Ile Leu Glu Leu Met Asn Val Pro Gly Leu
1               5                   10                  15

Thr Arg Glu Asn Val Ala Ser His Leu Gln Lys Tyr Arg Leu Tyr Leu
            20                  25                  30

Arg Arg Leu Ser Gly Val Ser Gln His Gln Asn Asn Ser Phe Leu Ser
            35                  40                  45

Pro Gln Glu Ala Ser Phe Gly Thr Ile Ser Ser Met Asn Gly Leu Asp
50                  55                  60

Leu Gln Thr Leu Ala Ala Gly Gln Leu Pro Ala Gln Ser Leu Ala
65                  70                  75                  80

Thr Leu Gln Ala Ala Gly Leu Gly Arg Ser Thr Val Lys Ser Gly Leu
            85                  90                  95

Pro Met Pro Leu Met Asp Gln Arg Asn Leu Phe Ser Phe Glu Asn Pro
            100                 105                 110

Arg Leu Arg Phe Gly Glu Gly Gln Gln Gln Leu Leu Asn Gly Ser Asn
            115                 120                 125

Asn Lys Pro Thr Asn Leu Leu His Gly Val Pro Thr Met Glu Pro Lys
            130                 135                 140

Gln Leu Ala Asn Leu His Gln Ser Ala Ala Gln Ser Leu Gly Asn Met
145                 150                 155                 160

Asn Met Arg Val Pro Ala Ser Ala Thr Gln Gly Asn Pro Leu Leu Met
            165                 170                 175

Gln Met Ala Gln Ser Gln Pro Arg Gly Pro Met Leu Ser Glu Trp Phe
            180                 185                 190

Ser Cys Ser Lys Ile Thr Glu Pro Leu Gln Ser Thr Val Ser Asn Gly
            195                 200                 205

Ile Ser Asp Gly Leu Met Gly Arg Asn Asn Met Ala Ser Ser Ser Arg
            210                 215                 220

Ala Pro Ser Phe Asn Pro Val Pro Gln Ser Ser Phe Leu Asn Phe
225                 230                 235                 240

Pro Met Asn Gln Ser Thr Glu Met Ser Val Ser Asn Phe Pro Leu Gly
            245                 250                 255

Ser Thr Pro Gly Ile Ser Ser Ile Thr Thr Lys Gly Ser Phe Gln Ala
```

```
             260                 265                 270
Glu Val Asn Ser Gly Ile Lys Gly Ser Ala Gly Phe Pro Ser Tyr Asp
            275                 280                 285

Ile Phe Asn Glu Leu Asn His Gln Lys Ser Arg Asp Trp Gly Met Thr
290                 295                 300

Asn Gln Gly Leu Met Tyr Asp Ser Ser His Ala Asn Pro Leu His
305                 310                 315                 320

Gly Asn Ile Asp Val Ser Pro Ser Val Leu Val His Gln Gly Phe Ser
                325                 330                 335

Ser Ala Gln Gln Thr Gly His Ser Arg Asp Ala Ser Leu Leu Gly Lys
            340                 345                 350

Ser Pro Phe Ser Leu Gly Glu Gly Leu Glu Gln Gly Asn Leu Gln Asn
        355                 360                 365

Gly Ala Gly Gln His Phe Asn Pro Leu Tyr Val Glu Asn Leu Thr Arg
    370                 375                 380

Val Lys Ala Glu Arg Val Pro Asp Ala Ser Ser His Thr Asp Leu Phe
385                 390                 395                 400

Pro Asp His Phe Gly Gln Asp Leu Met Ser Ala Arg Leu Lys Gln
                405                 410                 415

Gln Glu Gly Ile Gly Gln Ser Glu Asn Glu Phe Asp Phe Asp Gly Tyr
            420                 425                 430

Ser Leu Asp Asn Ile Pro Val
            435

<210> SEQ ID NO 47
<211> LENGTH: 199
<212> TYPE: PRT
<213> ORGANISM: Pinus taeda

<400> SEQUENCE: 47

Pro Ile Gly Leu Lys Val Leu Val Asp Asp Pro Leu Cys Leu
1               5                   10                  15

Leu Val Leu Glu Arg Met Pro Arg Gln Cys Asn Tyr Asn Val Thr Thr
            20                  25                  30

Cys Ser Arg Val Thr Gln Ala Ile Ser Met Val Lys Glu Asn Arg Asp
        35                  40                  45

Arg Phe Asp Leu Ile Met Ser Glu Val Tyr Leu Pro Asp Glu Asp Gly
    50                  55                  60

Phe Arg Leu Leu Glu Ile Val Gly Leu Gly Leu Asp Leu Pro Val Ile
65                  70                  75                  80

Met Met Ser Thr Asn Gly Asp Thr Ser Val Val Met Lys Gly Ile Thr
                85                  90                  95

His Gly Ala Cys Asp Tyr Phe Ile Lys Pro Ile Arg Ile Glu Glu Leu
            100                 105                 110

Arg Asn Ile Trp Gln His Val Met Arg Arg Gly Arg Glu Ser Leu
        115                 120                 125

Lys Asp Asp Leu Gly Glu Cys Glu Asp Arg Glu Val Ser Asp Ser Pro
    130                 135                 140

Asp Thr Ser Ser Lys Lys Arg Lys Asp Thr Ser Ser Gly Asp Tyr Ser
145                 150                 155                 160

Asp Glu Val Ile Asp Asp Ile Ser Ser Leu Lys Arg Ala Arg Val His
                165                 170                 175

Trp Thr Val Gln Leu His Gln Gln Phe Val Ile Ala Val Asn Gln Leu
            180                 185                 190
```

Gly Ile Glu Lys Ala Val Pro
            195

<210> SEQ ID NO 48
<211> LENGTH: 274
<212> TYPE: PRT
<213> ORGANISM: Pinus taeda

<400> SEQUENCE: 48

Arg Ile Glu Ala Leu Lys Asn Ile Trp Gln His Val Ile Arg Lys Lys
1               5                   10                  15

Arg Asn Glu Ser Lys Glu Leu Glu His Ser Gly Ser Val Asp Asp Ser
            20                  25                  30

Asp Arg His Lys Lys Gly Ser Asp Asp Val Glu Tyr Ala Ser Ser Val
        35                  40                  45

Asn Glu Gly Asn Asn Gly Met Trp Lys Pro Ser Lys Lys Arg Lys Glu
    50                  55                  60

Ala Arg Glu Glu Glu Asp Asp Gly Glu Gln Asp Asn Asp Asp Ser Ser
65                  70                  75                  80

Asn Leu Lys Lys Pro Arg Val Val Trp Ser Val Glu Leu His Gln Gln
                85                  90                  95

Phe Val Cys Ala Val Asn Gln Leu Gly Ile Asp Lys Ala Val Pro Lys
            100                 105                 110

Arg Ile Leu Glu Leu Met Asn Val Gln Gly Leu Thr Arg Glu Asn Val
        115                 120                 125

Ala Ser His Leu Gln Lys Tyr Arg Leu Tyr Leu Arg Arg Leu Ser Gly
    130                 135                 140

Val Gly Gln Pro Gln Ser Gly Phe Asn Ser Ser Phe Gly Gly Ser Met
145                 150                 155                 160

Glu Ala Ser Phe Gly Ser Ile Ser Ser Leu Asp Arg Ser Asp Leu Gln
                165                 170                 175

Ala Leu Ala Ala Ser Gly Gln Ile Ser Arg Gln Thr Leu Ala Ala Phe
            180                 185                 190

Gln Gly Gly Leu Leu Gly Arg Val Asn Gly Asn Asp Val Gly Met Ser
        195                 200                 205

Gly Val Asp Pro Thr Phe Leu Leu Gln Pro Asp Leu Gln Gly Leu Asn
    210                 215                 220

Cys Ser Leu Thr Asp Arg Ala Arg Phe Gly Gln Pro Leu Leu Asn Ser
225                 230                 235                 240

Gln Arg Asn Leu Leu Gln Gly Leu Pro Thr Gly Leu Glu Leu Lys Gln
                245                 250                 255

Leu Ala Gln Ser His Gln His Met Pro Ser Phe Gly Asn Leu Gly Met
            260                 265                 270

Ser Met

<210> SEQ ID NO 49
<211> LENGTH: 231
<212> TYPE: PRT
<213> ORGANISM: Pinus taeda

<400> SEQUENCE: 49

Pro Ile Gly Leu His Val Leu Val Asp Asn Asp Thr His Phe Leu
1               5                   10                  15

Ala Gly Leu Glu Gly Ile Leu Arg Lys Cys Gln Tyr Asn Val Thr Thr
            20                  25                  30

Ser Thr Ser Val Ser Gln Ala Ile Ser Leu Ala Met Glu Asn Lys Arg

```
                35                  40                  45
Ser Phe Asp Ile Val Met Ser Glu Val Tyr Phe Val Gly Glu Asp Gly
 50                  55                  60

Phe Lys Ile Leu Asp Val Val Gly Val Gly Leu Pro Val Ile
 65                  70                  75                  80

Met Met Ser Val Ser Gly Glu Thr Asn Val Met Arg Gly Ile Lys
                 85                  90                  95

Gly Gly Ala Cys Asn Tyr Leu Ile Lys Pro Ile Arg Met Glu Glu Val
                100                 105                 110

Arg Thr Leu Trp Gln His Val Arg Thr Arg Gly Arg Gln Tyr His
            115                 120                 125

His Val Val Lys Leu Lys Asp Ser His Gly Asp Ser Ser Glu Asn Gly
            130                 135                 140

Arg Val Ala Asp Ser Ser Glu Ser Thr Thr Cys Lys Asn Gly Lys Gln
145                 150                 155                 160

Gly Ser Gln Ile Ile Lys Asp Ile Arg Gly Leu Lys Glu Thr Arg Val
                165                 170                 175

Asn Trp Thr Leu Glu Leu His Gln Gln Phe Leu Asn Ala Val Asn Gln
                180                 185                 190

Leu Gly Val His Lys Val Val Pro Lys Ile Ile Leu Glu Ile Met Asp
                195                 200                 205

Val Pro Gly Leu Thr Arg Asp Asn Val Ala Ser His Leu Gln Lys Tyr
            210                 215                 220

Arg Leu Tyr Leu Lys Arg Leu
225                 230

<210> SEQ ID NO 50
<211> LENGTH: 149
<212> TYPE: PRT
<213> ORGANISM: Populus deltoides

<400> SEQUENCE: 50

Gln Phe Pro Ala Gly Leu Arg Val Leu Val Val Asp Asp Asp Ile Thr
 1                   5                  10                  15

Cys Leu Arg Leu Leu Glu Lys Met Leu Arg Arg Cys Leu Tyr His Val
                 20                  25                  30

Thr Thr Cys Ser Gln Ala Thr Ala Ala Leu Lys Leu Leu Arg Glu Arg
             35                  40                  45

Lys Gly Cys Phe Asp Val Val Leu Ser Asp Val His Met Pro Asp Met
 50                  55                  60

Asp Gly Phe Lys Leu Leu Glu Leu Val Gly Leu Glu Met Asp Leu Pro
 65                  70                  75                  80

Val Ile Met Met Ser Ala Asp Gly Arg Thr Ser Ala Val Met Arg Gly
                 85                  90                  95

Ile Ser His Gly Ala Cys Asp Tyr Leu Ile Lys Pro Ile Arg Glu Glu
                100                 105                 110

Glu Leu Lys Asn Ile Trp Gln His Val Ile Arg Lys Lys Trp Asn Glu
            115                 120                 125

Asn Lys Glu Gln Glu His Ser Gly Ser Phe Glu Asp Asn Asp Arg His
            130                 135                 140

Lys Arg Gly Asn Asp
145

<210> SEQ ID NO 51
<211> LENGTH: 6
```

```
<212> TYPE: PRT
<213> ORGANISM: Artificial
<220> FEATURE:
<223> OTHER INFORMATION: Synthetic-consensus sequence of the EAR motif

<400> SEQUENCE: 51

Asp Leu Glu Leu Arg Leu
1               5

<210> SEQ ID NO 52
<211> LENGTH: 12
<212> TYPE: PRT
<213> ORGANISM: Artificial
<220> FEATURE:
<223> OTHER INFORMATION: Synthetic-SRDX motif

<400> SEQUENCE: 52

Leu Asp Leu Asp Leu Glu Leu Arg Leu Gly Phe Ala
1               5                   10

<210> SEQ ID NO 53
<211> LENGTH: 7
<212> TYPE: PRT
<213> ORGANISM: Unknown
<220> FEATURE:
<223> OTHER INFORMATION: nuclear localization signal

<400> SEQUENCE: 53

Pro Lys Lys Lys Arg Lys Val
1               5

<210> SEQ ID NO 54
<211> LENGTH: 5
<212> TYPE: PRT
<213> ORGANISM: Unknown
<220> FEATURE:
<223> OTHER INFORMATION: Nuclear Localization Signal

<400> SEQUENCE: 54

Lys Ile Pro Ile Lys
1               5

<210> SEQ ID NO 55
<211> LENGTH: 29
<212> TYPE: PRT
<213> ORGANISM: Unknown
<220> FEATURE:
<223> OTHER INFORMATION: nuclear localization signal

<400> SEQUENCE: 55

Ser Pro Pro Lys Ala Val Lys Arg Pro Ala Ala Thr Lys Lys Ala Gly
1               5                   10                  15

Gln Ala Lys Lys Lys Lys Leu Asp Lys Glu Asp Glu Ser
            20                  25

<210> SEQ ID NO 56
<211> LENGTH: 36
<212> TYPE: PRT
<213> ORGANISM: Zea mays

<400> SEQUENCE: 56

Met Glu Glu Ala Val Thr Met Ala Pro Ala Ala Val Ser Ser Ala Val
1               5                   10                  15

Val Gly Asp Pro Met Glu Tyr Asn Ala Ile Leu Arg Arg Lys Leu Glu
            20                  25                  30
```

```
Glu Asp Leu Glu
        35

<210> SEQ ID NO 57
<211> LENGTH: 21
<212> TYPE: PRT
<213> ORGANISM: Nicotiana sp.

<400> SEQUENCE: 57

Lys Lys Arg Ala Arg Leu Val Arg Asn Arg Glu Ser Ala Gln Leu Ser
1               5                   10                  15

Arg Gln Arg Lys Lys
            20

<210> SEQ ID NO 58
<211> LENGTH: 16
<212> TYPE: DNA
<213> ORGANISM: Artificial
<220> FEATURE:
<223> OTHER INFORMATION: Synthetic-Primer 1 to generate SRDX specific
      probe

<400> SEQUENCE: 58
atgagcgcac tcgatc                                                       16

<210> SEQ ID NO 59
<211> LENGTH: 16
<212> TYPE: DNA
<213> ORGANISM: Artificial
<220> FEATURE:
<223> OTHER INFORMATION: Synthetic-Primer 2 to generate SRDX specific
      probe

<400> SEQUENCE: 59
agtttgtaca agaaag                                                       16

<210> SEQ ID NO 60
<211> LENGTH: 51
<212> TYPE: PRT
<213> ORGANISM: Arabidopsis thaliana

<400> SEQUENCE: 60

Lys Val Asp Trp Thr Pro Glu Leu His Lys Lys Phe Val Gln Ala Val
1               5                   10                  15

Glu Gln Leu Gly Val Asp Gln Ala Ile Pro Ser Arg Ile Leu Glu Leu
            20                  25                  30

Met Lys Val Gly Thr Leu Thr Arg His Asn Val Ala Ser His Leu Gln
        35                  40                  45

Lys Phe Arg
    50

<210> SEQ ID NO 61
<211> LENGTH: 51
<212> TYPE: PRT
<213> ORGANISM: Arabidopsis thaliana

<400> SEQUENCE: 61

Arg Val Val Trp Asp Glu Glu Leu His Gln Asn Phe Leu Asn Ala Val
1               5                   10                  15

Asp Phe Leu Gly Leu Glu Arg Ala Val Pro Lys Lys Ile Leu Asp Val
            20                  25                  30

Met Lys Val Asp Tyr Ile Ser Arg Glu Asn Val Ala Ser His Leu Gln
        35                  40                  45
```

-continued

Val Thr Phe
    50

<210> SEQ ID NO 62
<211> LENGTH: 46
<212> TYPE: PRT
<213> ORGANISM: Arabidopsis thaliana

<400> SEQUENCE: 62

Arg Glu Arg Trp Thr Glu Glu His Asn Arg Phe Ile Glu Ala Leu
1               5                   10                  15

Arg Leu Tyr Gly Arg Ala Trp Gln Lys Ile Glu Glu His Val Ala Thr
            20                  25                  30

Lys Thr Ala Val Gln Ile Arg Ser His Ala Gln Lys Phe Phe
        35                  40                  45

<210> SEQ ID NO 63
<211> LENGTH: 535
<212> TYPE: PRT
<213> ORGANISM: Arabidopsis thaliana

<400> SEQUENCE: 63

Met Val Ile Thr Ala Asn Asp Leu Ser Lys Trp Glu Asn Phe Pro Lys
1               5                   10                  15

Gly Leu Lys Val Leu Leu Leu Asn Gly Cys Asp Ser Asp Gly Asp
            20                  25                  30

Gly Ser Ser Ala Ala Glu Thr Arg Ser Glu Leu Glu Ser Met Asp Tyr
            35                  40                  45

Ile Val Thr Thr Phe Thr Asp Glu Thr Glu Ala Leu Ser Ala Val Val
    50                  55                  60

Lys Asn Pro Glu Ser Phe His Ile Ala Ile Val Glu Val Asn Met Ser
65                  70                  75                  80

Ala Glu Ser Glu Ser Phe Lys Phe Leu Glu Ala Ala Lys Asp Val Leu
                85                  90                  95

Pro Thr Ile Met Ile Ser Thr Asp His Cys Ile Thr Thr Thr Met Lys
            100                 105                 110

Cys Ile Ala Leu Gly Ala Val Glu Phe Leu Gln Lys Pro Leu Ser Pro
        115                 120                 125

Glu Lys Leu Lys Asn Ile Trp Gln His Val Val His Lys Ala Phe Asn
    130                 135                 140

Asp Gly Gly Ser Asn Val Ser Ile Ser Leu Lys Pro Val Lys Glu Ser
145                 150                 155                 160

Val Val Ser Met Leu His Leu Glu Thr Asp Met Thr Ile Glu Glu Lys
                165                 170                 175

Asp Pro Ala Pro Ser Thr Pro Gln Leu Lys Gln Asp Ser Arg Leu Leu
            180                 185                 190

Asp Gly Asp Cys Gln Glu Asn Ile Asn Phe Ser Met Glu Asn Val Asn
        195                 200                 205

Ser Ser Thr Glu Lys Asp Asn Met Glu Asp His Gln Asp Ile Gly Glu
    210                 215                 220

Ser Lys Ser Val Asp Thr Thr Asn Arg Lys Leu Asp Asp Lys Val
225                 230                 235                 240

Val Val Lys Glu Glu Arg Gly Asp Ser Glu Lys Glu Glu Gly Glu
                245                 250                 255

Thr Gly Asp Leu Ile Ser Glu Lys Thr Asp Ser Val Asp Ile His Lys
            260                 265                 270

Lys Glu Asp Glu Thr Lys Pro Ile Asn Lys Ser Ser Gly Ile Lys Asn
                275                 280                 285

Val Ser Gly Asn Lys Thr Ser Arg Lys Lys Val Asp Trp Thr Pro Glu
            290                 295                 300

Leu His Lys Lys Phe Val Gln Ala Val Glu Gln Leu Gly Val Asp Gln
305                 310                 315                 320

Ala Ile Pro Ser Arg Ile Leu Glu Leu Met Lys Val Gly Thr Leu Thr
                325                 330                 335

Arg His Asn Val Ala Ser His Leu Gln Lys Phe Arg Gln His Arg Lys
            340                 345                 350

Asn Ile Leu Pro Lys Asp Asp His Asn His Arg Trp Ile Gln Ser Arg
                355                 360                 365

Glu Asn His Arg Pro Asn Gln Arg Asn Tyr Asn Val Phe Gln Gln Gln
370                 375                 380

His Arg Pro Val Met Ala Tyr Pro Val Trp Gly Leu Pro Gly Val Tyr
385                 390                 395                 400

Pro Pro Gly Ala Ile Pro Pro Leu Trp Pro Pro Leu Gln Ser Ile
                405                 410                 415

Gly Gln Pro Pro Pro Trp His Trp Lys Pro Pro Tyr Pro Thr Val Ser
                420                 425                 430

Gly Asn Ala Trp Gly Cys Pro Val Gly Pro Val Thr Gly Ser Tyr
            435                 440                 445

Ile Thr Pro Ser Asn Thr Thr Ala Gly Gly Phe Gln Tyr Pro Asn Gly
            450                 455                 460

Ala Glu Thr Gly Phe Lys Ile Met Pro Ala Ser Gln Pro Asp Glu Glu
465                 470                 475                 480

Met Leu Asp Gln Val Val Lys Glu Ala Ile Ser Lys Pro Trp Leu Pro
                485                 490                 495

Leu Pro Leu Gly Leu Lys Pro Pro Ser Ala Glu Ser Val Leu Ala Glu
            500                 505                 510

Leu Thr Arg Gln Gly Ile Ser Ala Val Pro Ser Ser Ser Cys Leu Ile
            515                 520                 525

Asn Gly Ser His Arg Leu Arg
            530                 535

<210> SEQ ID NO 64
<211> LENGTH: 292
<212> TYPE: PRT
<213> ORGANISM: Arabidopsis thaliana

<400> SEQUENCE: 64

Met Gln Pro Leu Asn Met Ala Glu Ile Leu Asp His Arg Gly Val Leu
1               5                   10                  15

Thr Asp Gly Asp Asp Gly Pro Phe Arg Asn Leu Thr Asn Phe Tyr Asp
            20                  25                  30

Met Phe Ser Ser Asn Phe Pro Glu Gly Leu Arg Val Leu Val Phe Asp
        35                  40                  45

Glu Asp Pro Ser Tyr Leu Leu Ile Leu Glu Arg His Leu Gln Lys Phe
50                  55                  60

Gln Tyr Gln Val Thr Ile Cys Asn Glu Val Asn Lys Ala Met His Thr
65                  70                  75                  80

Leu Arg Asn His Arg Asn Arg Phe Asp Leu Ala Met Ile Gln Val Asn
                85                  90                  95

Asn Ala Glu Gly Asp Ile Phe Arg Phe Leu Ser Glu Ile Gly Ser Glu

```
            100                 105                 110
Met Asp Leu Pro Ile Ile Ile Ser Glu Asp Asp Ser Val Lys Ser
            115                 120                 125

Val Lys Lys Trp Met Ile Asn Gly Ala Ala Asp Tyr Leu Ile Lys Pro
            130                 135                 140

Ile Arg Pro Glu Asp Leu Arg Ile Val Phe Lys His Leu Val Lys Lys
145                 150                 155                 160

Met Arg Glu Arg Arg Ser Val Val Thr Gly Glu Ala Glu Lys Ala Ala
                165                 170                 175

Gly Glu Lys Ser Ser Ser Val Gly Asp Ser Thr Ile Arg Asn Pro Asn
            180                 185                 190

Lys Ser Lys Arg Ser Ser Cys Leu Glu Ala Glu Val Asn Glu Glu Asp
            195                 200                 205

Arg His Asp His Asn Asp Arg Ala Cys Ala Ser Ser Ala Lys Lys Arg
        210                 215                 220

Arg Val Val Trp Asp Glu Glu Leu His Gln Asn Phe Leu Asn Ala Val
225                 230                 235                 240

Asp Phe Leu Gly Leu Glu Arg Ala Val Pro Lys Lys Ile Leu Asp Val
                245                 250                 255

Met Lys Val Asp Tyr Ile Ser Arg Glu Asn Val Ala Ser His Leu Gln
            260                 265                 270

Val Thr Phe Leu Ile Tyr Asn Ile Ile Val His Phe Gln Gln His Phe
            275                 280                 285

Cys Phe Tyr Ser
            290

<210> SEQ ID NO 65
<211> LENGTH: 608
<212> TYPE: PRT
<213> ORGANISM: Arabidopsis thaliana

<400> SEQUENCE: 65

Met Glu Thr Asn Ser Ser Gly Glu Asp Leu Val Ile Lys Thr Arg Lys
1               5                   10                  15

Pro Tyr Thr Ile Thr Lys Gln Arg Glu Arg Trp Thr Glu Glu His
                20                  25                  30

Asn Arg Phe Ile Glu Ala Leu Arg Leu Tyr Gly Arg Ala Trp Gln Lys
            35                  40                  45

Ile Glu Glu His Val Ala Thr Lys Thr Ala Val Gln Ile Arg Ser His
    50                  55                  60

Ala Gln Lys Phe Phe Ser Lys Val Glu Lys Glu Ala Glu Ala Lys Gly
65                  70                  75                  80

Val Ala Met Gly Gln Ala Leu Asp Ile Ala Ile Pro Pro Arg Pro
                85                  90                  95

Lys Arg Lys Pro Asn Asn Pro Tyr Pro Arg Lys Thr Gly Ser Gly Thr
            100                 105                 110

Ile Leu Met Ser Lys Thr Gly Val Asn Asp Gly Lys Glu Ser Leu Gly
            115                 120                 125

Ser Glu Lys Val Ser His Pro Glu Met Ala Asn Glu Asp Arg Gln Gln
        130                 135                 140

Ser Lys Pro Glu Glu Lys Thr Leu Gln Glu Asp Asn Cys Ser Asp Cys
145                 150                 155                 160

Phe Thr His Gln Tyr Leu Ser Ala Ala Ser Ser Met Asn Lys Ser Cys
                165                 170                 175
```

-continued

Ile Glu Thr Ser Asn Ala Ser Thr Phe Arg Glu Phe Leu Pro Ser Arg
            180                 185                 190

Glu Glu Gly Ser Gln Asn Asn Arg Val Arg Lys Glu Ser Asn Ser Asp
        195                 200                 205

Leu Asn Ala Lys Ser Leu Glu Asn Gly Asn Glu Gln Gly Pro Gln Thr
    210                 215                 220

Tyr Pro Met His Ile Pro Val Leu Val Pro Leu Gly Ser Ser Ile Thr
225                 230                 235                 240

Ser Ser Leu Ser His Pro Pro Ser Glu Pro Asp Ser His Pro His Thr
                245                 250                 255

Val Ala Gly Asp Tyr Gln Ser Phe Pro Asn His Ile Met Ser Thr Leu
            260                 265                 270

Leu Gln Thr Pro Ala Leu Tyr Thr Ala Ala Thr Phe Ala Ser Ser Phe
        275                 280                 285

Trp Pro Pro Asp Ser Ser Gly Gly Ser Pro Val Pro Gly Asn Ser Pro
    290                 295                 300

Pro Asn Leu Ala Ala Met Ala Ala Thr Val Ala Ala Ala Ser Ala
305                 310                 315                 320

Trp Trp Ala Ala Asn Gly Leu Leu Pro Leu Cys Ala Pro Leu Ser Ser
                325                 330                 335

Gly Gly Phe Thr Ser His Pro Pro Ser Thr Phe Gly Pro Ser Cys Asp
            340                 345                 350

Val Glu Tyr Thr Lys Ala Ser Thr Leu Gln His Gly Ser Val Gln Ser
        355                 360                 365

Arg Glu Gln Glu His Ser Glu Ala Ser Lys Ala Arg Ser Ser Leu Asp
    370                 375                 380

Ser Glu Asp Val Glu Asn Lys Ser Lys Pro Val Cys His Glu Gln Pro
385                 390                 395                 400

Ser Ala Thr Pro Glu Ser Asp Ala Lys Gly Ser Asp Gly Ala Gly Asp
                405                 410                 415

Arg Lys Gln Val Asp Arg Ser Ser Cys Gly Ser Asn Thr Pro Ser Ser
            420                 425                 430

Ser Asp Asp Val Glu Ala Asp Ala Ser Glu Arg Gln Glu Asp Gly Thr
        435                 440                 445

Asn Gly Glu Val Lys Glu Thr Asn Glu Asp Thr Asn Lys Pro Gln Thr
    450                 455                 460

Ser Glu Ser Asn Ala Arg Arg Ser Arg Ile Ser Ser Asn Ile Thr Asp
465                 470                 475                 480

Pro Trp Lys Ser Val Ser Asp Glu Gly Arg Ile Ala Phe Gln Ala Leu
                485                 490                 495

Phe Ser Arg Glu Val Leu Pro Gln Ser Phe Thr Tyr Arg Glu Glu His
            500                 505                 510

Arg Glu Glu Glu Gln Gln Gln Gln Glu Gln Arg Tyr Pro Met Ala Leu
        515                 520                 525

Asp Leu Asn Phe Thr Ala Gln Leu Thr Pro Val Asp Asp Gln Glu Glu
    530                 535                 540

Lys Arg Asn Thr Gly Phe Leu Gly Ile Gly Leu Asp Ala Ser Lys Leu
545                 550                 555                 560

Met Ser Arg Gly Arg Thr Gly Phe Lys Pro Tyr Lys Arg Cys Ser Met
                565                 570                 575

Glu Ala Lys Glu Ser Arg Ile Leu Asn Asn Asn Pro Ile Ile His Val
            580                 585                 590

Glu Gln Lys Asp Pro Lys Arg Met Arg Leu Glu Thr Gln Ala Ser Thr

<210> SEQ ID NO 66
<211> LENGTH: 16
<212> TYPE: PRT
<213> ORGANISM: Artificial
<220> FEATURE:
<223> OTHER INFORMATION: Synthetic-carboxy terminus of fusion protein
      ARR1-SRDX

<400> SEQUENCE: 66

Leu Met Ser Ala Leu Asp Leu Asp Leu Glu Leu Arg Leu Gly Phe Ala
1               5                   10                  15

<210> SEQ ID NO 67
<211> LENGTH: 51
<212> TYPE: DNA
<213> ORGANISM: Artificial
<220> FEATURE:
<223> OTHER INFORMATION: Synthetic-nucleotide sequence coding for
      carboxy terminus of ARR1-SRDX

<400> SEQUENCE: 67
ctcatgagcg cactcgatct ggatctagaa ctccgtttgg gtttcgcttg a            51

<210> SEQ ID NO 68
<211> LENGTH: 36
<212> TYPE: DNA
<213> ORGANISM: Artificial
<220> FEATURE:
<223> OTHER INFORMATION: Synthetic-forward primer for amplification of
      1000 bp ARR6 promoter fragment

<400> SEQUENCE: 68
gcaagcttac aatcacaaca gctcatgaac aaaatc                              36

<210> SEQ ID NO 69
<211> LENGTH: 33
<212> TYPE: DNA
<213> ORGANISM: Artificial
<220> FEATURE:
<223> OTHER INFORMATION: Synthetic-reverse primer for amplification of
      1000 bp ARR6 promoter fragment

<400> SEQUENCE: 69
gctctagaga aaccatggtg gcagtggttg ggc                                 33

<210> SEQ ID NO 70
<211> LENGTH: 56
<212> TYPE: PRT
<213> ORGANISM: Artificial Sequence
<220> FEATURE:
<223> OTHER INFORMATION: Synthetic-Consensus sequence of DNA-binding
      domain of B-type ARRs according to SEQ ID NOs: 1 to 11
<220> FEATURE:
<221> NAME/KEY: VARIANT
<222> LOCATION: (1)..(1)
<223> OTHER INFORMATION: Xaa is selected from R or K, preferably R
<220> FEATURE:
<221> NAME/KEY: VARIANT
<222> LOCATION: (2)..(2)
<223> OTHER INFORMATION: Xaa is selected from V, I or M, preferably V
<220> FEATURE:
<221> NAME/KEY: VARIANT
<222> LOCATION: (3)..(3)
<223> OTHER INFORMATION: Xaa is selected from V, L, Q, T or W,
      preferably V
<220> FEATURE:
<221> NAME/KEY: VARIANT
<222> LOCATION: (5)..(5)

```
<223> OTHER INFORMATION: Xaa is selected from S or T
<220> FEATURE:
<221> NAME/KEY: VARIANT
<222> LOCATION: (6)..(6)
<223> OTHER INFORMATION: Xaa is any amino acid, preferably V, H, I, Q,
      F, D, P, E, or N
<220> FEATURE:
<221> NAME/KEY: VARIANT
<222> LOCATION: (7)..(7)
<223> OTHER INFORMATION: Xaa is selected from E, S or P, preferably E
<220> FEATURE:
<221> NAME/KEY: VARIANT
<222> LOCATION: (9)..(9)
<223> OTHER INFORMATION: Xaa is selected from H or Q, preferably H
<220> FEATURE:
<221> NAME/KEY: VARIANT
<222> LOCATION: (10)..(26)
<223> OTHER INFORMATION: Xaa is preferably independently from each other
      selected from A, C, D, E, F, G, H, I, K, L, M, N,
      Q, R, S, V or Y
<220> FEATURE:
<221> NAME/KEY: VARIANT
<222> LOCATION: (22)..(26)
<223> OTHER INFORMATION: optionally absent
<220> FEATURE:
<221> NAME/KEY: VARIANT
<222> LOCATION: (29)..(29)
<223> OTHER INFORMATION: Xaa is selected from K, R, T or V, preferably K
<220> FEATURE:
<221> NAME/KEY: VARIANT
<222> LOCATION: (30)..(30)
<223> OTHER INFORMATION: Xaa is selected from I or L, preferably I
<220> FEATURE:
<221> NAME/KEY: VARIANT
<222> LOCATION: (31)..(31)
<223> OTHER INFORMATION: Xaa is selected from L or V, preferably L
<220> FEATURE:
<221> NAME/KEY: VARIANT
<222> LOCATION: (32)..(32)
<223> OTHER INFORMATION: Xaa is selected from D, A, E, or K, preferably
      D or E
<220> FEATURE:
<221> NAME/KEY: VARIANT
<222> LOCATION: (33)..(33)
<223> OTHER INFORMATION: Xaa is selected from L, M, F, C, I, or Y,
      preferably L
<220> FEATURE:
<221> NAME/KEY: VARIANT
<222> LOCATION: (34)..(34)
<223> OTHER INFORMATION: Xaa is selected from M or L, preferably M
<220> FEATURE:
<221> NAME/KEY: VARIANT
<222> LOCATION: (35)..(35)
<223> OTHER INFORMATION: Xaa is selected from N, Q or S, preferably N
<220> FEATURE:
<221> NAME/KEY: VARIANT
<222> LOCATION: (36)..(39)
<223> OTHER INFORMATION: Xaa is independently from each other selected
      from E, L, M, N, or R, or preferably absent
<220> FEATURE:
<221> NAME/KEY: VARIANT
<222> LOCATION: (40)..(40)
<223> OTHER INFORMATION: Xaa is selected from V or I, preferably V
<220> FEATURE:
<221> NAME/KEY: VARIANT
<222> LOCATION: (41)..(41)
<223> OTHER INFORMATION: Xaa is selected from P, D, E, or Q, preferably
      P
<220> FEATURE:
<221> NAME/KEY: VARIANT
<222> LOCATION: (42)..(42)
<223> OTHER INFORMATION: Xaa is selected from G, K, W, or Y, preferably
      G
<220> FEATURE:
<221> NAME/KEY: VARIANT
<222> LOCATION: (43)..(43)
<223> OTHER INFORMATION: Xaa is selected from L or I, preferably L
<220> FEATURE:
<221> NAME/KEY: VARIANT
```

```
<222> LOCATION: (44)..(44)
<223> OTHER INFORMATION: Xaa is selected from T or S, preferably T
<220> FEATURE:
<221> NAME/KEY: VARIANT
<222> LOCATION: (46)..(46)
<223> OTHER INFORMATION: Xaa is selected from E, N or S, preferably E
<220> FEATURE:
<221> NAME/KEY: VARIANT
<222> LOCATION: (55)..(55)
<223> OTHER INFORMATION: Xaa is selected from Y, F or H, preferably Y

<400> SEQUENCE: 70

Xaa Xaa Xaa Trp Xaa Xaa Xaa Leu Xaa Xaa Xaa Xaa Xaa Xaa Xaa Xaa
 1               5                  10                  15

Xaa Xaa Xaa Xaa Xaa Xaa Xaa Xaa Xaa Xaa Pro Lys Xaa Xaa Xaa Xaa
             20                  25                  30

Xaa Xaa Xaa Xaa Xaa Xaa Xaa Xaa Xaa Xaa Xaa Xaa Arg Xaa Asn Val
         35                  40                  45

Ala Ser His Leu Gln Lys Xaa Arg
 50                  55
```